(12) United States Patent
Berniac et al.

(10) Patent No.: US 7,935,687 B2
(45) Date of Patent: May 3, 2011

(54) METHODS FOR TREATING SPINAL MUSCULAR ATROPHY USING TETRACYCLINE COMPOUNDS

(75) Inventors: Joel Berniac, Stoneham, MA (US);
Todd Bowser, Charlton, MA (US);
Michael Draper, Plaistow, NH (US);
Stuart B. Levy, Boston, MA (US);
Mark L. Nelson, Norfolk, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 246 days.

(21) Appl. No.: 12/102,623

(22) Filed: Apr. 14, 2008

(65) Prior Publication Data

US 2009/0118269 A1    May 7, 2009

Related U.S. Application Data

(60) Provisional application No. 60/923,031, filed on Apr. 12, 2007, provisional application No. 60/930,883, filed on May 18, 2007, provisional application No. 60/946,110, filed on Jun. 25, 2007, provisional application No. 60/994,163, filed on Sep. 18, 2007, provisional application No. 60/986,192, filed on Nov. 7, 2007.

(51) Int. Cl.
*A61K 31/835* (2006.01)
*A61K 31/16* (2006.01)

(52) U.S. Cl. ............ 514/152; 514/231.5; 514/616

(58) Field of Classification Search ............ 514/152, 514/231.5, 616
See application file for complete search history.

(56) References Cited

U.S. PATENT DOCUMENTS

| | | | |
|---|---|---|---|
| 2,980,584 A | 4/1961 | Hammer | 514/153 |
| 2,990,331 A | 6/1961 | Horst et al. | 514/619 |
| 3,062,717 A | 11/1962 | Hammer | 514/154 |
| 3,165,531 A | 1/1965 | Blackwood et al. | 549/41 |
| 3,454,697 A | 7/1969 | Joyner et al. | 514/154 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 4,806,529 A | 2/1989 | Strumskis | 426/129 |
| 5,021,407 A | 6/1991 | Levy | 514/154 |
| 5,258,372 A | 11/1993 | Levy | 514/154 |
| 5,589,470 A | 12/1996 | Levy | 514/154 |
| 5,811,412 A | 9/1998 | Levy | 514/154 |
| 6,256,365 B1 | 7/2001 | Lai | 378/4 |
| 6,500,812 B2 | 12/2002 | Nelson et al. | 514/152 |
| 6,617,318 B1 | 9/2003 | Nelson et al. | 514/152 |
| 6,624,168 B2 | 9/2003 | Nelson et al. | 514/252.1 |
| 6,642,270 B2 | 11/2003 | Nelson et al. | 514/464 |
| 6,683,068 B2 | 1/2004 | Nelson et al. | 514/152 |
| 6,818,634 B2 | 11/2004 | Nelson et al. | 514/152 |
| 6,818,635 B2 | 11/2004 | Nelson et al. | 514/152 |
| 6,833,365 B2 * | 12/2004 | Levy et al. | 514/152 |
| 6,841,546 B2 | 1/2005 | Draper et al. | 514/152 |
| 6,846,939 B2 | 1/2005 | Nelson et al. | 552/205 |
| 6,849,615 B2 | 2/2005 | Nelson et al. | 514/152 |
| 7,001,918 B2 | 2/2006 | Huss et al. | 514/427 |
| 7,045,507 B2 | 5/2006 | Draper et al. | 514/31 |
| 7,056,902 B2 | 6/2006 | Nelson et al. | 514/152 |
| 7,067,681 B2 | 6/2006 | Nelson et al. | 552/206 |
| 7,094,806 B2 | 8/2006 | Nelson et al. | 514/471 |
| 7,202,235 B2 | 4/2007 | Levy et al. | 514/152 |
| 7,208,482 B2 | 4/2007 | Garcia-Luzon et al. | 514/152 |
| 7,323,492 B2 | 1/2008 | Huss et al. | 514/429 |
| 7,326,696 B2 | 2/2008 | Nelson et al. | 514/512 |
| 7,361,674 B2 | 4/2008 | Nelson et al. | 514/357 |
| 7,414,041 B2 | 8/2008 | Levy | 514/154 |
| 7,521,437 B2 | 4/2009 | Nelson et al. | 514/152 |
| 7,553,828 B2 | 6/2009 | Nelson et al. | 514/152 |
| 2003/0069721 A1 | 4/2003 | Podlegar | 703/11 |
| 2004/0138183 A1 | 7/2004 | Nelson et al. | 514/152 |
| 2004/0176334 A1 | 9/2004 | Nelson et al. | 514/152 |
| 2004/0214800 A1 | 10/2004 | Levy et al. | 514/152 |
| 2004/0214801 A1 | 10/2004 | Nelson et al. | 514/152 |
| 2004/0242548 A1 | 12/2004 | Draper et al. | 514/152 |
| 2005/0020545 A1 | 1/2005 | Draper et al. | 514/152 |
| 2005/0038002 A1 | 2/2005 | Nelson et al. | 514/152 |
| 2005/0070510 A1 | 3/2005 | Draper et al. | 514/152 |
| 2005/0143352 A1 | 6/2005 | Nelson et al. | 514/152 |
| 2005/0250744 A1 | 11/2005 | Levy et al. | 514/152 |
| 2005/0288262 A1 | 12/2005 | Bandarage et al. | 514/152 |
| 2006/0003971 A1 | 1/2006 | Nelson | 514/152 |
| 2006/0084634 A1 | 4/2006 | Huss et al. | 514/152 |

(Continued)

FOREIGN PATENT DOCUMENTS

DE    2346535    4/1974

(Continued)

OTHER PUBLICATIONS

Wirth et. al. (Expert Opinion on Drug Discovery (2007) 2:437-451).*
Summer (The Journal of the American Society for Experimental Therapeutics (2006) 3:235-245).*
Dorwald F. A. (Side reactions in organic synthesis, 2005, Wiley, VCH, Weinheim, pg. IX of Preface).*
Andreassi et. al. (Human Molecular Genetics (2001) 10:2841-2849).*
Andreassi et al., "Aclarubicin Treatment Restores SMN Levels to Cells Derived from Type 1 Spinal Muscular Atrophy Patients", *Human Molecular Genetics*, 10(24), 2841-2849 (2001).

(Continued)

*Primary Examiner* — Brandon J Fetterolf
*Assistant Examiner* — Marcos Sznaidman
(74) *Attorney, Agent, or Firm* — Mintz Levin Cohn Ferris Glovsky and Popeo, P.C.; Ivor R. Elrifi; Heidi A. Erlacher

(57) ABSTRACT

Methods for using tetracycline compounds for the treatment of spinal muscular atrophy are described.

63 Claims, 6 Drawing Sheets

U.S. PATENT DOCUMENTS

| | | | |
|---|---|---|---|
| 2006/0089336 A1 | 4/2006 | Nelson et al. | 514/152 |
| 2006/0166944 A1 | 7/2006 | Berniac et al. | 514/152 |
| 2006/0166945 A1 | 7/2006 | Abato et al. | 514/152 |
| 2006/0166946 A1 | 7/2006 | Nelson et al. | 514/152 |
| 2006/0194773 A1 | 8/2006 | Levy et al. | 514/152 |
| 2006/0281717 A1 | 12/2006 | Berniac et al. | 514/152 |
| 2006/0287283 A1 | 12/2006 | Amoo et al. | 514/152 |
| 2007/0072834 A1 | 3/2007 | Nelson et al. | 514/152 |
| 2007/0093455 A1 | 4/2007 | Abato et al. | 514/114 |
| 2007/0167415 A1 | 7/2007 | Levy et al. | 514/152 |
| 2007/0270389 A1 | 11/2007 | Garcia-Luzon et al. | 514/152 |
| 2008/0015169 A1 | 1/2008 | Nelson et al. | 514/152 |
| 2008/0070873 A1 | 3/2008 | Alekshun et al. | 514/153 |
| 2008/0118979 A1 | 5/2008 | Draper et al. | 435/375 |
| 2008/0167273 A1 | 7/2008 | Nelson et al. | 514/152 |
| 2008/0287401 A1 | 11/2008 | Johnston et al. | 514/152 |
| 2008/0300424 A1 | 12/2008 | Nelson et al. | 564/167 |
| 2008/0306032 A1 | 12/2008 | Nelson et al. | 514/152 |
| 2008/0312193 A1 | 12/2008 | Assefa et al. | 514/152 |
| 2009/0054379 A1 | 2/2009 | Huss et al. | 514/152 |
| 2009/0118269 A1 | 5/2009 | Berniac et al. | 514/231.5 |
| 2009/0124583 A1 | 5/2009 | Nelson et al. | 514/152 |
| 2009/0131696 A1 | 5/2009 | Levy | 552/203 |
| 2009/0156842 A1 | 6/2009 | Seyedi et al. | 552/204 |

FOREIGN PATENT DOCUMENTS

| | | |
|---|---|---|
| WO | WO 03/005971 A2 | 1/2003 |
| WO | WO 2004/038000 A2 | 5/2004 |

OTHER PUBLICATIONS

Berge et al., "Pharmaceutical Salts", *J. Pharm. Sci.*, 66(1):1-19 (1977).

Chang et al., "Treatment of Spinal Muscular Atrophy by Sodium Butyrate", *PNAS*, 98(17), 9808-9813 (2001).

Lim et al., "Modulation of Survival Motor Neuron Pre-mRNA Splicing by Inhibition of Alternative 3' Splice Site Pairing", *The Journal of Biological Chemistry*, 276(48), 45476-45483 (2001).

Miyajima et al., "Identification of a Cis-acting Element for the Regulation of SMN Exon 7 Splicing", The Journal of Biological Chemistry, 277(26), 23271-23277 (2002).

Nilges et al., "Identification and Characterization of a Tetracycline Semiquinone Formed during the Oxidation of Minocycline", *J. Org. Chem.*, 56:5623-5630 (1991).

Skordis et al., "Bifunctional Antisense Oligonucleotides Provide a Trans-Acting Splicing Enhancer that Stimulates SMN2 Gene Expression in Patient Fibroblasts", *PNAS*, 100(7), 4114-4119 (2003).

Sossi et al., "Premature Termination Mutations in Exon 3 of the SMN1 Gene are Associated with Exon Skipping and a Relatively Mild SMA Phenotype", European Journal of Human Genetics, 9, 113-120 (2001).

Zhang et al., "An in Vivo Reporter System for Measuring Increased Inclusion of Exon 7 in SMN2 mRNA: Potential Therapy of SMA", *Gene Therapy*, 8, 1532-1538 (2001).

Andreassi et al., "Aclarubicin treatment restores SMN levels to cells derived from type I spinal muscular atrophy patients", *Human Mol. Genetics*, 10(24):2841-2849 (2001).

"Families of spinal muscular atrophy and paratek pharmaceuticals expand drug discovery collaboration for spinal muscular atrophy", http://www.paratekpharm.com/m_press.html, XP-002492415, 2 pages (2007).

"SMA summit on drug development, session 7: identification of tetracycline compounds that correct defective SMN2 splicing", http://www.fsma.org/research/clinical/smadrugsummit/smadrugsummitslides/, (2007).

Sumner, C.J. "Therapeutics development for spinal muscular atrophy", *J. Am. Soc. Exp. NeuroTherap.*, 3(2):235-245 (2006).

\* cited by examiner

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 1
aagtgagaac tccaggtctc ctg                                             23

<210> SEQ ID NO 2
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 2
gtggtgtcat ttagtgctgc tc                                              22
```

METHODS FOR TREATING SPINAL MUSCULAR ATROPHY USING TETRACYCLINE COMPOUNDS

RELATED APPLICATIONS

This application is claims priority to U.S. Provisional Patent Application No. 60/986,192 filed on Nov. 7, 2007; U.S. Provisional Patent Application No. 60/994,163 filed on Sep. 18, 2007; U.S. Provisional Patent Application No. 60/946,110, filed on Jun. 25, 2007; U.S. Provisional Patent Application No. 60/930,883, filed on May 18, 2007; and U.S. Provisional Patent Application No. 60/923,031, filed on Apr. 12, 2007. The contents of each the aforementioned applications are hereby incorporated in their entirety.

BACKGROUND

Spinal Muscular Atrophy (SMA) is an often-fatal genetic disorder resulting from the loss of the Survival Motor Neuron (SMN) protein encoded by the Survival Motor Neuron (SMN) gene. The SMN genes, SMN1 and SMN2, are located on chromosome 5 and SMA is caused by the loss of SMN1 from both chromosomes. SMN2, while being almost identical to SMN1, is less effective at making the SMN protein. The severity of SMA is affected by the efficiency at which SMN2, of which there are several copies, produces the SMN protein.

SMA can be classified by the severity of the disorder. Infantile SMA (SMA type 1 or Werdnig-Hoffmann disease) affects infants from the ages of 0-6 months and is the most severe. It causes the affected child to be unable to maintain an independent sitting position. Intermediate SMA (SMA type 2) affects children from the ages of 7-18 months. Children with SMA type 2 are never able to stand and walk, but are able to maintain a sitting position at least some time in their life. The onset of weakness is usually recognized some time between 6 and 18 months. Juvenile SMA (SMA type 3 or Kugelberg-Welander disease) affects children generally older than 18 months. These children are able to walk at some time. Adult SMA (SMA type 4) usually causes weakness beginning in late adolescence in the tongue, hands, or feet, and it progresses to other areas of the body. The course of disease is much slower and has little or no impact on life expectancy. Typically, the earlier the onset of the disease, the shorter the lifespan of the victim. Infants with the severe form of SMA frequently succumb to respiratory disease due to weakness of the muscles that support breathing. Children with milder forms of SMA naturally live much longer although they may need extensive medical support, especially those at the more severe end of the spectrum.

Although gene replacement strategies are being tested in animals, current treatment for SMA consists of prevention and management of the secondary effect of chronic motor unit loss. Currently, there are no drug therapies available for the treatment or prevention of SMA.

SUMMARY OF THE INVENTION

The invention pertains, at least in part to a method for treating a subject for spinal muscular atrophy. The method includes administering to the subject an effective amount of a tetracycline compound, such that the spinal muscular atrophy is treated. Advantageously, the tetracycline compounds used in the methods of the invention have one or more of the following characteristics: 1) potency in modulating mRNA splicing; 2) central nervous system and/or brain penetration; 3) decreased phototoxic properties and 4) decreased antibacterial properties.

The invention also pertains, at least in part, to a method for modulating SMN2 mRNA splicing. The method includes contacting SMN2 mRNA with a tetracycline compound, such that SMN2 mRNA splicing is modulated.

The invention also pertains to a method for modulating SMN protein (SMNp) levels in a subject, by administering to the subject an effective amount of a tetracycline compound, such that SMNp levels are modulated in the subject.

In another embodiment, the invention pertains to packaged tetracycline compound, comprising an effective amount of a tetracycline compound and instructions for using the tetracycline compound for the treatment of spinal muscular atrophy.

DETAILED DESCRIPTION OF THE INVENTION

Figure 1:
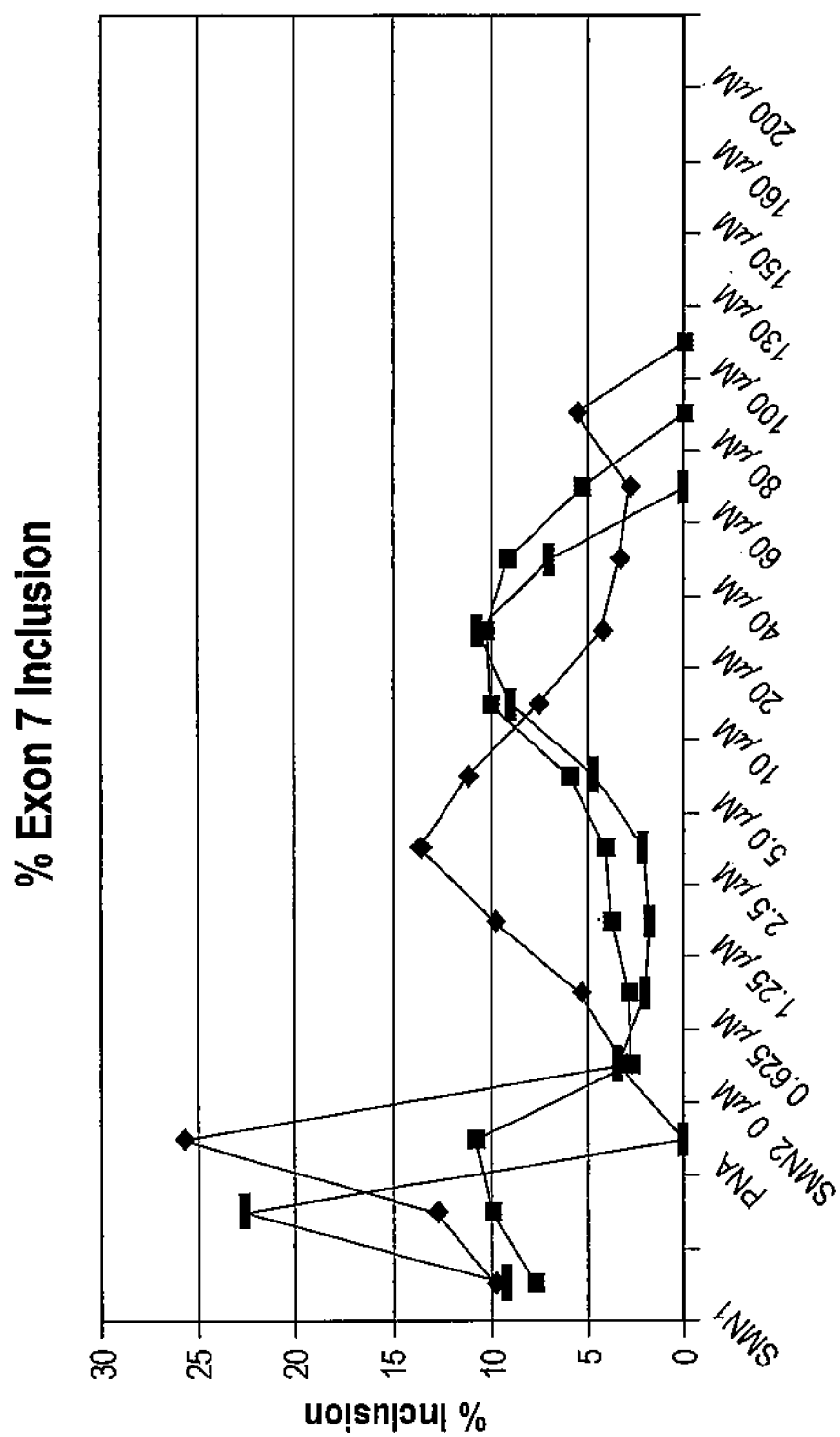
FIG. 1 is a chart illustrating the in vitro cell-free splicing assay results for compound J, expressed in percent inclusion of exon 7 in the SMN2 mRNA.

In one embodiment, the invention pertains to a method for treating a subject for spinal muscular atrophy. The method includes administering to the subject an effective amount of a tetracycline compound, such that the spinal muscular atrophy is treated.

The term "spinal muscular atrophy" or "SMA" includes infantile SMA, SMA type I or Werdnig-Hoffman disease; intermediate SMA or SMA type 2; juvenile SMA, SMA type 3 or Kugelberg-Welander disease; and Adult SMA or SMA type 4.

The term "subject" includes humans, and other animals (e.g., mammals, e.g., cats, dogs, horses, pigs, cows, sheep, rodents, rabbits, squirrels, bears, primates (e.g., chimpanzees, and gorillas) which are capable of (or are currently) suffering from spinal muscular atrophy.

The language "effective amount" of the tetracycline compound is that amount necessary or sufficient to treat or prevent spinal muscular atrophy (SMA) in a subject, e.g. prevent the various symptoms of SMA. The effective amount may vary depending on such factors as the size and weight of the subject, or the particular tetracycline compound. For example, the choice of the tetracycline compound may affect what constitutes an "effective amount." One of ordinary skill in the art would be able to study the aforementioned factors and make the determination regarding the effective amount of the tetracycline compound without undue experimentation.

The regimen of administration may affect what constitutes an effective amount. The tetracycline compound may be administered to the subject either prior to or after the onset of SMA. Further, several divided dosages, as well as staggered dosages may be administered daily or sequentially, or the dose can be continuously infused, orally administered, administered by inhalation, or can be a bolus injection. The dosages of the tetracycline compound(s) may be proportionally increased or decreased as indicated by the exigencies of the therapeutic or prophylactic situation.

The term "treated," "treating" or "treatment" includes therapeutic and/or prophylactic treatment. The treatment includes the diminishment or alleviation of at least one symptom associated with or caused by SMA. For example, treatment includes diminishment of one or several symptoms of SMA or complete eradication of a SMA.

The terms "modulate," "modulating" and "modulation" include increasing or decreasing SMN2 mRNA splicing or SMNp levels. The term "modulation of SMNp levels" includes the modulation of the expression of SMNp.

SMN2 is a highly homologous copy of SMN1, which is related to the survival of motor neurons. The SMN1 gene is present in all normal individuals, but it is absent in greater than 95% of SMA patients. Only five nucleotides distinguish SMN1 from SMN2 genes. One of the nucleotides is located in exon 7 and is believed to be responsible for the alternative splicing of exon 7 that is specific to the SMN2 transcripts. Full-length transcripts are generally produced by SMN1, and the predominant form encoded by SMN2 is lacking exon 7. The truncated transcript results in an expected protein lacking the last C-terminal 16 residues. Despite the presence of the SMN2 gene in SMA patients, SMN2 is unable to compensate for the deficit of SMN1. It is hypothesized that the development of the SMA phenotype is caused by two events: an inherited (or de novo) SMN1 gene mutation, and a constitutive defect of the SMN2 gene leading to the production of a low amount of full-length SMN protein with the predominant form being truncated and lacking exon 7 (Nicole et al. Muscle and Nerve. July, 2002, 4).

SMN protein studies in a large cohort of SMA patients have revealed a tight inverted correlation between the amount of the protein encoded by the SMN2 gene and the clinical severity of the SMA. It has been found that the full-length transcript of SMN1 and SMN2 is translated into a stable SMN protein while the truncated transcript lacking exon 7 (the predominant form encoded by SMN2) is translated into an unstable protein.

The invention also pertains, at least in part, to a method for modulating, (e.g., increasing) SMN2 mRNA splicing. The method includes contacting the SMN2 mRNA with a tetracycline compound, such that SMN2 mRNA splicing is modulated. The modulation of SMN2 mRNA splicing by the tetracycline compounds of the invention may be determined by, for example, the cell-free splicing assay (as described in Example 1), the cellular gems assay (as described in Example 2), or by Western blot (as described in Example 3). In one embodiment, the tetracycline compound for modulating SMN2 mRNA splicing is not tetracycline. In another embodiment, the tetracycline compound increases cellular SMN protein levels in a subject. In yet another embodiment, the tetracycline compound increases gems in cells of said subject. One of skill in the art would understand that an increase in gems in cells may correlate with an increase in the cellular levels of SMN protein.

In one embodiment, the tetracycline compound increases the percentage of exon 7 inclusion and/or intron 6 during mRNA splicing. In another embodiment, the percentage of exon 7 inclusion during mRNA splicing may be determined by the assay described in Example 1. In yet another embodiment, the tetracycline compound increases the percentage of exon 7 inclusion during mRNA splicing by about 4-fold or greater, about 5-fold or greater, about 6-fold or greater, about 7-fold or greater, about 8-fold or greater, about 9-fold or greater, about 10-fold or greater, about 11-fold or greater, about 12-fold or greater, about 13-fold or greater, about 14-fold or greater, about 15-fold or greater, about 16-fold or greater, about 17-fold or greater, about 18-fold or greater, about 19-fold or greater, about 20-fold or greater, about 21-fold or greater, about 22-fold or greater, about 23-fold or greater, about 24-fold or greater, or about 25-fold. In one particular embodiment, the tetracycline compound increases the percentage of exon 7 inclusion during mRNA splicing of SMN2 by about 2.6-fold. In another embodiment, the tetracycline increases exon 7 inclusion by greater than 5-fold compared to background at a concentration of 10 µM. In yet another embodiment, the tetracycline compound increases exon 7 inclusion is about 19% compared to about 3% for a background at a concentration of 10 µM.

In one embodiment, the maximum percentage exon 7 inclusion observed upon administration of a tetracycline compound (e.g., $E_{max}$ determined as described in Example 1) is at least about 5 percent or greater, at least about 10 percent or greater, at least about 15 percent or greater, at least about 20 percent or greater, at least about 25 percent or greater, at least about 30 percent or greater, at least about 35 percent or greater, at least about 40 percent or greater, at least about 45 percent or greater, at least about 50 percent or greater, at least about 55 percent or greater, at least about 60 percent or greater, at least about 65 percent or greater, at least about 70 percent or greater, at least about 75 percent or greater, at least about 80 percent or greater, at least about 85 percent or greater, at least about 90 percent or greater, at least about 95 percent or greater or at least about 100 percent. In a further embodiment, the maximum percentage exon 7 inclusion is at least about 23% or about 30%.

In another embodiment, the lowest concentration of a tetracycline compound at which maximum exon 7 inclusion is observed (e.g., $C_{max}$ determined as described in Example 1) is less than about 30 µM, less than about 29 µM, less than about 28 µM, less than about 27 µM, less than about 26 µM, less than about 25 µM, less than about 24 µM, less than about 23 µM, less than about 22 µM, less than about 21 µM, less than about 20 µM, less than about 19 µM, less than about 18 µM, less than about 17 µM, less than about 16 µM, less than about 15 µM, less than about 14 µM, less than about 13 µM, less than about 12 µM, less than about 11 µM, less than about 10 µM, less than about 9 µM, less than about 8 µM, less than about 7 µM, less than about 6 µM, less than about 5 µM, less than about 4 µM, less than about 3 µM, less than about 2 µM or less than about 1 µM.

The invention also pertains to a method of modulating (e.g., increasing) SMNp levels in a subject by administering to the subject an effective amount of a tetracycline compound to the subject. In one embodiment, the SMNp levels may be increased. In another embodiment, the SMNp levels in the subject may be increased by about 2-fold or greater, about 3-fold or greater, about 4-fold or greater, about 5-fold or greater, about 6-fold or greater, about 7-fold or greater, about 8-fold or greater, about 9-fold or greater, about 10-fold or greater, about 11-fold or greater, about 12-fold or greater, about 13-fold or greater, about 14-fold or greater, about 15-fold or greater, about 16-fold or greater, about 17-fold or greater, about 18-fold or greater, about 19-fold or greater, about 20-fold or greater, about 21-fold or greater, about 22-fold or greater, about 23-fold or greater, about 24-fold or greater, about 25-fold or greater, about 26-fold or greater, about 27-fold or greater, about 28-fold or greater, about 29-fold or greater, about 30-fold or greater, about 31-fold or greater, about 32-fold or greater, about 33-fold or greater, about 34-fold or greater, about 35-fold or greater, about 36-fold or greater, about 37-fold or greater, about 38-fold or greater, about 39-fold or greater, about 40-fold or greater, about 41-fold or greater, about 42-fold or greater, about 43-fold or greater, about 44-fold or greater, about 45-fold or greater, about 46-fold or greater, about 47-fold or greater, about 48-fold or greater, about 49-fold or greater or about 50-fold or greater.

The term "SMNp" includes the Survival Motor Neuron (SMN) protein which is encoded by the Survival Motor Neuron (SMN) gene. In another embodiment, the modulation of SMNp levels may be determined by a Western blot assay or by a gems assay (see Examples 2 and 3, respectively). In one embodiment, SMNp levels may be increased by about 40% at a concentration of 10 μM of the tetracycline compound. In another embodiment, SMNp levels may be increased by about 2.7-fold or by about 8.6-fold at a concentration of 2.5 μM of the tetracycline compound, such as compound AB.

In another embodiment, the tetracycline compound increases full-length (FL) SMN2 mRNA expression in a subject (e.g., in the brain, central nervous system, liver and/or kidney). The expression of SMN2 mRNA may be increased by about 23% in the kidney or by about 74% in the liver upon administration of a tetracycline compound, such as compound AB.

The term "tetracycline compound" includes substituted tetracycline compounds and compounds with a similar ring structure to tetracycline, including minocycline, doxycycline, tetracycline, chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

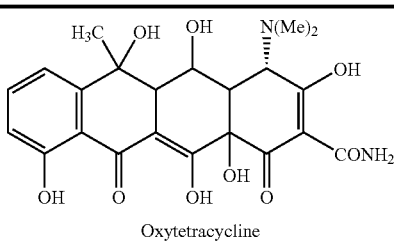

Oxytetracycline

TABLE 1-continued

Methacycline

Tetracycline

Demeclocycline

Doxycycline

Sancycline

Minocycline

TABLE 1-continued

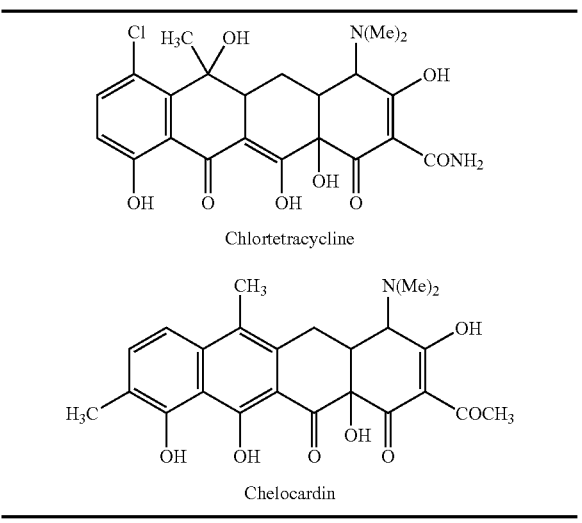

Chlortetracycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a Cl-6, 12 hemiketal tetracyclines; 11a Cl-6-methylene tetracyclines; 6, 13 diol tetracyclines; 6-benzylthiomethylene tetracyclines; 7, 11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7, 13-epithiotetracyclines; oxytetracyclines; pyrazolotetracyclines; 11a halogens of tetracyclines; 12a formyl and other esters of tetracyclines; 5, 12a esters of tetracyclines; 10, 12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The tetracycline compounds may or may not have antibacterial or antiinfective activity. In certain embodiments of the invention, the tetracycline compound has antiinfective, anti-inflammatory and/or antibacterial activity.

In one embodiment, the tetracycline compound is not a compound shown in Table 1 (for example, oxytetracycline (e.g., a compound of formula I in which X is $CR^6R^{6'}$; $R^2$, $R^{2'}$, $R^3$, $R^{4a}$, $R^{5'}$ $R^7$, $R^8$, $R^9$, $R^{11}$ and $R^{12}$ are hydrogen; $R^5$ and $R^{10}$ are hydroxyl; $R^{6'}$ is methyl; $R^4$ is $NR^{4'}R^{4''}$ and $R^{4'}$ and $R^{4''}$ are methyl), demeclocycline (e.g., a compound of formula I in which X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, $R^{12}$ are hydrogen; $R^{6'}$ and $R^{10}$ are each hydroxyl; $R^7$ is chlorine; $R^4$ is $NR^{4'}R^{4''}$ and $R^{4'}$ and $R^{4''}$ are methyl), minocycline (e.g., a compound of formula I in which X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$ and $R^{12}$ are hydrogen, $R^7$ is —$N(CH_3)_2$, $R^{10}$ is hydroxyl; $R^4$ is $NR^{4'} R^{4''}$ and $R^{4'}$ and $R^{4''}$ are methyl), methacycline (e.g., a compound of formula I in which X is $C=R^6R^{6'}$; $R^2$, $R^{2'}$, $R^3$, $R^{4a}$, $R^5$, $R^{5'}$, $R^6$, $R^{6'}$, $R^8$, $R^9$, $R^{11}$ and $R^{12}$ are hydrogen; $R^{5'}$ and $R^{10}$ are hydroxyl; $R^4$ is $NR^4R^{4''}$ and $R^{4'}$ and $R^{4''}$ are methyl), doxycycline, (e.g., a compound of formula I in which X is $CR^6R^{6'}$; $R^2$, $R^{2'}$, $R^3$, $R^{4a}$, $R^5$, $R^6$, $R^7$, $R^8$m $R^9$, $R^{11}$ and $R^{12}$ are hydrogen; $R^{5'}$ and $R^{10}$ are hydroxyl; $R^{6'}$ is methyl; $R^4$ is $NR^{4'}R^{4''}$ and $R^{4'}$ and $R^{4''}$ are methyl), chlortetracycline (e.g., a compound of formula I in which X is $CR^6R^{6'}$; $R^2$, $R^{2'}$, $R^3$, $R^{4a}$, $R^5$, $R^{5'}$, $R^8$, $R^9$, $R^{11}$ and $R^{12}$ are hydrogen; $R^{6'}$ and $R^{10}$ are hydroxyl; $R^6$ is methyl; $R^7$ is chlorine; $R^4$ is $NR^{4'}R^{4''}$ and $R^{4'}$ and $R^{4''}$ are methyl), tetracycyline (e.g., a compound of formula I in which X is $CR^6R^{6'}$; $R^2$, $R^{2'}$, $R^3$, $R^{4a}$, $R^5$, $R^{5'}$, $R^7$, $R^8$, $R^9$, $R^{11}$, $R^{12}$ are hydrogen; $R^6$ and $R^{10}$ are hydroxyl; $R^{6'}$ is methyl; $R^4$ is $NR^{4'}R^{4''}$ and $R^{4'}$ and $R^{4''}$ are methyl) or sancycline (e.g., a compound of formula I in which X is $CR^6R^{6'}$; $R^2$, $R^{2'}$, $R^3$, $R^{4a}$, $R^5$, $R^{5'}$, $R^6$, $R^{6'}$, $R^7$, $R^8$, $R^9$, $R^{11}$ and $R^{12}$ are hydrogen; $R^{10}$ is hydroxyl; $R^4$ is $NR^{4'}R^{4''}$ and $R^{4'}$ and $R^{4''}$ are methyl)).

The term "tetracycline compound" also includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function, e.g., treat spinal muscular atrophy. In one embodiment, the tetracycline compound is a substituted oxytetracycline compound (e.g., $R^4$ is $NR^{4'}R^{4''}$, $R^{4a}$ and $R^{5'}$ are each hydrogen, $R^5$ is hydroxyl, X is $CR^6R^{6'}$, $R^6$ is hydroxyl and $R^{6'}$ is methyl). In another embodiment, the tetracycline compound is a substituted minocycline compound (e.g., $R^4$ is $NR^{4'}R^{4''}$, X is $CR^6R^{6'}$, $R^{4a}$ $R^5$, $R^{5'}$, $R^6$ and $R^{6'}$ are each hydrogen and $R^7$ is $N(CH_3)_2$). In yet another embodiment, the tetracycline compound is a substituted doxycycline compound (e.g., $R^4$ is $NR^{4'}R^{4''}$, X is $CR^6R^{6'}$, $R^{4a}$ and $R^{5'}$ are each hydrogen, $R^5$ is hydroxyl, $R^6$ is methyl and $R^{6'}$ is hydrogen). In another embodiment, the tetracycline compound is a substituted tetracycline compound (e.g., $R^4$ is $NR^{4'}R^{4''}$ X is $CR^6R^{6'}$, $R^{4a}$, $R^5$ and $R^{5'}$ are each hydrogen, $R^6$ is methyl and $R^{6'}$ is hydroxyl). In one embodiment, the tetracycline compound is a substituted sancycline compound (e.g., $R^4$ is $NR^{4'}R^{4''}$, X is $CR^6R^{6'}$, $R^{4a}$, $R^5$, $R^{5'}$, $R^6$ and $R^{6'}$ are each hydrogen). In another embodiment, the tetracycline compound is a substituted demeclocycline compound (e.g., $R^4$ is $NR^{4'}R^{4''}$, X is $CR^6R^{6'}$, $R^{4a}$, $R^5$, $R^{5'}$ and $R^6$ are hydrogen, $R^{6'}$ is hydroxyl and $R^7$ is chlorine). In another embodiment, the tetracycline compound is a substituted methacycline compound (e.g., $R^4$ is $NR^{4'}R^{4''}$, X is $C=CR^6R^6$, $R^5$ is hydroxyl and $R^{4a}$, $R^{5'}$, $R^{6'}$ and $R^6$ are hydrogen). In another embodiment, the tetracycline compound is a substituted chlortetracycline compound (e.g., $R^4$ is $NR^{4'}R^{4''}$, X is $CR^6R^{6'}$. $R^{4a}$ and $R^{5'}$ are hydrogen, $R^5$ is hydroxyl, and $R^6$ is methyl, $R^{6'}$ is hydroxyl and $R^7$ is chlorine). In certain embodiments, the substituted tetracycline compound is a 7-substituted sancycline compound, a 9-substituted minocycline compound, or a 7,9-substituted sancycline compound.

The term "tetracycline compound" also includes tetracycline compounds of the formula (I):

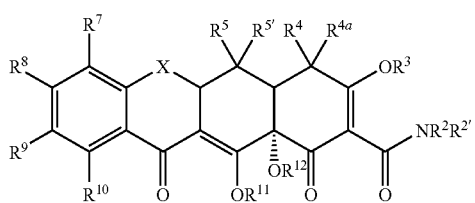

(I)

wherein

X is CHC(R$^{13}$Y'Y), CR$^{6'}$R$^6$, C=CR$^{6'}$R$^6$, S, NR$^6$, or O;

R$^2$, R$^{2'}$, R$^{4'}$, and R$^{4''}$ are each independently hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or a prodrug moiety;

R$^3$, R$^{4a}$, R$^{11}$ and R$^{12}$ are each independently hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or a prodrug moiety;

R$^4$ is NR$^{4'}$R$^{4''}$, hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or a prodrug moiety;

R$^5$ and R$^{5'}$ are each hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or a prodrug moiety;

R$^6$ and R$^{6'}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

R$^7$ is hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or —(CH$_2$)$_{0-3}$(NR$^{7c}$)$_{0-1}$C(=W')WR$^{7a}$;

R$^8$ is hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or —(CH$_2$)$_{0-3}$(NR$^{8c}$)$_{0-1}$C(=E')ER$^{8a}$;

R$^9$ is hydrogen, alkyl, alkenyl, alkynyl, acyl, hydroxyl, alkoxy, halogen, thioether, sulfinyl, sulfonyl, amino, cyano, nitro, carbonyl, aryl, heterocyclic or —(CH$_2$)$_{0-3}$(NR$^{9c}$)$_{0-1}$C(=Z')ZR$^{9a}$;

R$^{10}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

R$^{7a}$, R$^{7b}$, R$^{7c}$, R$^{7d}$, R$^{7e}$, R$^{7f}$, R$^{8a}$, R$^{8b}$, R$^{8c}$, R$^{8d}$, R$^{8e}$, R$^{8f}$, R$^{9a}$, R$^{9b}$, R$^{9c}$, R$^{9d}$, R$^{9e}$, and R$^{9f}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

R$^{13}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

E is CR$^{8d}$R$^{8e}$, S, NR$^{8b}$ or O;

E' is O, NR$^{8f}$, or S;

W is CR$^{7d}$R$^{7e}$, S, NR$^{7b}$ or O;

W' is O, NR$^{7f}$, or S;

X is CHC(R$^{13}$Y'Y), C=CR$^{13}$y, CR$^{6'}$R$^6$, S, NR$^6$ or O;

Z is CR$^{9d}$R$^{9e}$, S, NR$^{9b}$ or O;

Z' is O, S, or NR$^{9f}$;

Y' and Y are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and pharmaceutically acceptable salts, esters and enantiomers thereof.

In one embodiment, X is CR$^6$R$^{6'}$; R$^2$, R$^{2'}$, R$^3$, R$^5$, R$^6$, R$^{6'}$, R$^8$, R$^9$, R$^{11}$ and R$^{12}$ are each hydrogen, R$^4$ is NR$^{4'}$R$^{4''}$, wherein R$^{4'}$ and R$^{4''}$ are each methyl and R$^{10}$ is hydrogen or hydroxyl.

In another embodiment, R$^7$ is aryl e.g., phenyl or heteroaryl.

In a further embodiment, the aryl is substituted with one or more substituents which allow the substituted tetracycline compound to perform its intended function, e.g., treat spinal muscular atrophy. Examples of such substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

In one embodiment, the aryl is phenyl. In yet another embodiment, the phenyl is substituted with aminocarbonyl, alkylaminocarbonyl, dialkylaminocarbonyl or acylamino.

In a further embodiment, the aryl is heteroaryl (e.g., quinolinyl or pyridinyl). In another embodiment, the heteroaryl (e.g., pyridinyl) is substituted with alkoxyl.

In another embodiment, R$^7$ is aminocarbonyl (e.g., alkylaminocarbonyl).

In a further embodiment, R$^7$ is alkylcarbonyl (e.g., aminoalkylcarbonyl).

In yet another embodiment, R$^7$ is aminoalkyl.

In another embodiment, R$^7$ is heterocyclic (e.g., tetrahydropyridinyl).

In one embodiment, X is CR$^6$R$^{6'}$; R$^2$, R$^{2'}$, R$^3$, R$^5$, R$^6$, R$^{6'}$, R$^8$, R$^{10}$ R$^{11}$, and R$^{12}$ are each hydrogen; and R$^4$ is NR$^{4'}$R$^{4''}$, wherein R$^{4'}$ and R$^{4''}$ are each methyl; and R$^7$ is —N(CH$_3$)$_2$.

In another embodiment, R$^9$ is aryl e.g., phenyl or heteroaryl.

In a further embodiment, the aryl is substituted with one or more substituents which allow the substituted tetracycline compound to perform its intended function, e.g., treat spinal muscular atrophy. Examples of such substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

In one embodiment, the aryl is phenyl. In another embodiment, the phenyl is substituted with alkylaminocarbonyl.

In yet another embodiment, X is CR$^6$R$^{6'}$; R$^2$, R$^{2'}$, R$^3$, R$^4$, R$^5$, R$^6$, R$^{6'}$, R$^8$, R$^9$, R$^{11}$, and R$^{12}$ are each hydrogen, and R$^{10}$ is hydroxyl.

In another embodiment, R$^7$ is aryl (e.g., phenyl or heteroaryl).

In a further embodiment, the aryl is substituted with one or more substituents which allow the substituted tetracycline compound to perform its intended function, e.g., treat spinal muscular atrophy. Examples of such substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

In one embodiment, $R^7$ is a phenyl. In a further embodiment, the phenyl is substituted with substituted or unsubstituted aminocarbonyl (e.g., alkylaminocarbonyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is amino (e.g., dialkylamino, for example, dimethylamino); and $R^9$ is aryl, for example, of formula II:

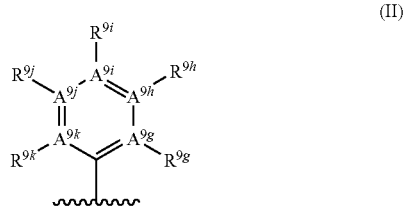

(II)

wherein $A^{9g}$, $A^{9h}$, $A^{9i}$, $A^{9j}$ and $A^{9k}$ are each independently N or C; and when $A^{9g}$, $A^{9h}$, $A^{9i}$, $A^{9j}$ and $A^{9k}$ are C, $R^{9g}$, $R^{9h}$, $R^{9i}$, $R^{9j}$ and $R^{9k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or when $A^{9g}$, $A^{9h}$, $A^{9i}$, $A^{9j}$ and $A^{9k}$ is N, $R^{9g}$, $R^{9h}$, $R^{9i}$, $R^{9j}$ and $R^{9k}$ are absent.

In one embodiment, $A^{9g}$, $A^{9h}$, $A^{9i}$, $A^{9j}$ and $A^{9k}$ are each C; $R^{9g}$, $R^{9i}$, $R^{9j}$ and $R^{9k}$ are each hydrogen and $R^{9h}$ is carbonyl, for example, of formula III:

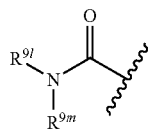

(III)

wherein $R^{9l}$ and $R^{9m}$ may each be independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or $R^{9l}$ and $R^{9m}$ are linked to form a 5- or 6-membered aryl, heterocyclic or aliphatic ring.

In one embodiment, $R^{9m}$ is hydrogen and $R^{9l}$ is alkyl, for example, of formula IV:

(IV)

wherein $D^9$ is O, N or $CR^{9'}$;

a is an integer from 0 to 10;

$R^{9'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^9$ is N or $CR^{9'}$, $R^{9n}$ and $R^{9o}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{9n}$ and $R^{9o}$ are linked to form a 5- or 6-membered aryl, heterocyclic or aliphatic ring; or when $D^9$ is O, $R^{9n}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{9o}$ is absent.

In another embodiment, $D^9$ is N; a is 2 or 3 and $R^{9n}$ and $R^{9o}$ are each alkyl (e.g., methyl). Alternatively, $D^9$ is N; a is 0; and $R^{9n}$ and $R^{9o}$ are each hydrogen.

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is amino (e.g., dialkylamino, for example, dimethylamino); and $R^9$ is aryl, for example, of formula X:

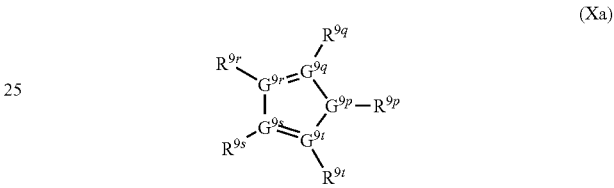

(Xa)

wherein $G^{9p}$ is N, O, S or $CR^{9u}$;

$G^{9q}$, $G^{9r}$, $G^{9s}$ and $G^{9t}$ are each independently N or C;

$R^{9u}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

$R^{9p}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^{9p}$ is N or $CR^{9u}$ or $R^{9p}$ is absent when $G^{9p}$ is O or S;

$R^{9q}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^{9q}$ is C or $R^{9q}$ is absent when $G^{9q}$ is N;

$R^{9r}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^{9r}$ is C or $R^{9r}$ is absent when $G^{9r}$ is N;

$R^{9s}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{9s}$ is covalently bonded to the 9-position of the tetracycline compound when $G^{9s}$ is C; or $R^{9s}$ is absent when $G^{9s}$ is N; and $R^{9t}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{9t}$ is covalently bonded to the 9-position of the tetracycline compound when $G^{9t}$ is C; or $R^{9t}$ is absent when $G^{9t}$ is N;

provided that one of $R^{9s}$ or $R^{9t}$ are covalently bonded to the 9-position of the tetracycline compound.

In one embodiment, $G^{9p}$ is O; $G^{9q}$, $G^{9r}$, $G^{9s}$ and $G^{9t}$ are each C; $R^{9t}$ is covalently bonded to the 9-position of the tetracycline compound; $R^{9r}$ and $R^{9s}$ are each hydrogen and $R^{9q}$ is alkyl, for example, or formula IV:

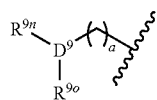

(IV)

wherein $D^9$ is O, N, $NR^{9'}$ or $CR^{9'}$;

a is an integer from 0 to 10;

$R^{9'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^9$ is N or $CR^{9'}$, $R^{9n}$ and $R^{9o}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{9n}$ and $R^{9o}$ are linked to form a 5- or 6-membered aryl, heterocyclic or aliphatic ring; or when $D^9$ is O, $R^{9n}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{9o}$ is absent.

In another embodiment, $D^9$ is N; a is 1; and $R^{9n}$ and $R^{9o}$ are linked to form a 6-membered heterocyclic ring (e.g., a piperazinyl ring, such as an N-substituted piperazinyl ring, for example, N-substituted with hydroxyalkyl (e.g., hydroxyethyl). In another embodiment, the piperazinyl ring is

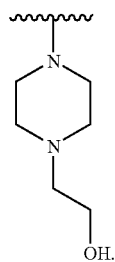

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^7$ is aryl, for example, of formula V:

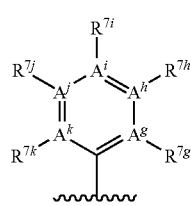

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is hydrogen.

In one embodiment, $A^g$, $A^h$, $A^i$, $A^j$ and $A^k$ are each C; $R^{7g}$, $R^{7h}$, $R^{7i}$ and $R^{7k}$ are each hydrogen and $R^{7j}$ is carbonyl, for example, of formula VI:

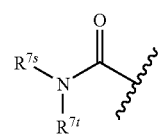

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In another embodiment, $R^{7t}$ is hydrogen and $R^{7s}$ is alkyl, for example, of formula VII:

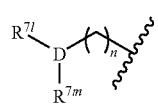

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; or when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In yet another embodiment, D is N; n is 2 and $R^{7l}$ and $R^{7m}$ are each alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

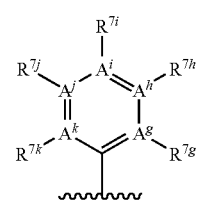

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}, R^{7h}, R^{7i}, R^{7j}$ and $R^{7k}$ are absent when $A^g, A^h, A^i, A^j$ and $A^k$ are N.

In another embodiment, $R^4$ is amino (e.g., dialkylamino, for example, dimethylamino); $A^g, A^h, A^i, A^j$ and $A^k$ are each C; $R^{7g}, R^{7h}, R^{7i}$ and $R^{7k}$ are each hydrogen and $R^{7j}$ is carbonyl, for example, of formula VI:

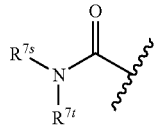

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In yet another embodiment, $R^{7s}$ and $R^{7t}$ are each hydrogen. Alternatively, $R^{7s}$ and $R^{7t}$ are each alkyl (e.g., methyl) or $R^{7s}$ and $R^{7t}$ are linked to form a 6-membered heterocyclic ring (e.g., a piperazinyl ring, such as an N-alkylated piperazinyl, for example, N-methyl piperazinyl). In another embodiment, the piperazinyl compound is

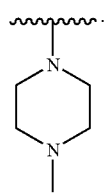

In one embodiment, X is $CR^6R^{6'}$; $R^2, R^{2'}, R^3, R^{4a}, R^5, R^{5'}, R^6, R^{6'}, R^8, R^9, R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

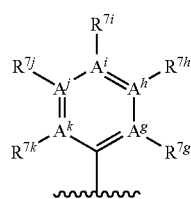

(V)

wherein $A^g, A^h, A^i, A^j$ and $A^k$ are each independently N or C; and when $A^g, A^h, A^i, A^j$ and $A^k$ are C; $R^{7g}, R^{7h}, R^{7i}, R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}, R^{7h}, R^{7i}, R^{7j}$ and $R^{7k}$ are absent when $A^g, A^h, A^i, A^j$ and $A^k$ are N.

In another embodiment, $R^4$ is amino (e.g., dialkylamino, for example, dimethylamino); $A^g, A^h, A^i, A^j$ and $A^k$ are each C; $R^{7g}, R^{7h}, R^{7i}$ and $R^{7k}$ are each hydrogen and $R^{7j}$ is carbonyl, for example, of formula VI:

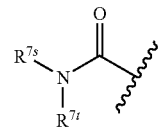

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In one embodiment, $R^{7s}$ is alkyl, for example, a moiety of formula VII:

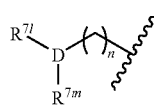

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, $R^{7t}$ is hydrogen; D is N; n is 1; $R^{7m}$ is hydrogen and $R^{7l}$ is aryl (e.g., a heteroaryl, for example, furanyl).

In a further embodiment, $R^{7t}$ is hydrogen; D is N; n is 2 and $R^{7l}$ and $R^{7m}$ are each alkyl (e.g., methyl, propyl or isopropyl). In another embodiment, $R^{7l}$ and $R^{7m}$ are each hydrogen or $R^{7l}$ is hydrogen and $R^{7m}$ is alkyl (e.g., methyl) or acyl. Alternatively, $R^{7l}$ and $R^{7m}$ are linked to form a 6-membered heterocyclic ring (e.g., piperidinyl or morpholylinyl) or a 5-membered heterocyclic ring (e.g., pyrrolidinyl).

In another embodiment, $R^{7t}$ is hydrogen; D is N; n is 3 or 4; and $R^{7l}$ and $R^{7m}$ are each alkyl (e.g., methyl).

In one embodiment, X is $CR^6R^{6'}$; $R^2, R^{2'}, R^3, R^{4a}, R^5, R^{5'}, R^6, R^{6'}, R^8, R^9, R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

(V)

wherein

Aᵍ, Aʰ, Aⁱ, Aʲ and Aᵏ are each independently N or C; and when Aᵍ, Aʰ, Aⁱ, Aʲ and Aᵏ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when Aᵍ, Aʰ, Aⁱ, Aʲ and Aᵏ are N.

In another embodiment, $R^4$ is amino (e.g., dialkylamino, for example, dimethylamino); Aᵍ, Aʰ, Aⁱ, Aʲ and Aᵏ are each C; $R^{7g}$, $R^{7h}$, $R^{7i}$ and $R^{7k}$ are each hydrogen and $R^{7j}$ is carbonyl, for example, of formula VI:

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In another embodiment, $R^{7t}$ is hydrogen; $R^{7s}$ is alkyl, for example, alkoxycarbonyl substituted alkyl (e.g., ethoxycarbonylethyl or $CH_3CH_2C(=O)CH_2CH_2—$); n-butyl; heterocyclic substituted alkyl (e.g., heterocyclic substituted alkyl such as piperidinyl substituted alkyl (e.g., piperidinyl substituted propyl or hydroxyl substituted alkyl (e.g., hydroxypropyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

(V)

wherein

Aᵍ, Aʰ, Aⁱ, Aʲ and Aᵏ are each independently N or C; and when Aᵍ, Aʰ, Aⁱ, Aʲ and Aᵏ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when Aᵍ, Aʰ, Aⁱ, Aʲ and Aᵏ are N.

In another embodiment, $R^4$ is amino (e.g., dialkylamino, for example, dimethylamino); Aᵍ, Aʰ, Aⁱ, Aʲ and Aᵏ are each C; $R^{7g}$, $R^{7h}$, $R^{7i}$ and $R^{7k}$ are each hydrogen and $R^{7j}$ is carbonyl, for example, of formula VI:

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In one embodiment, $R^{7s}$ is alkyl, for example, a moiety of formula VII:

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, $R^{7t}$ is hydrogen; D is O; n is 2 or 3 and $R^{7l}$ is alkyl (e.g., methyl) or hydrogen.

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

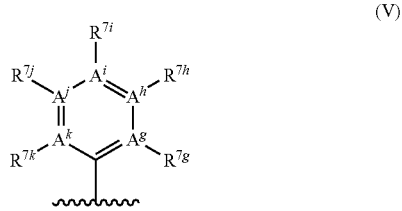

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^{7i}$ and $R^{7k}$ are each hydrogen and $R^{7j}$ is carbonyl, for example, of formula VI:

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In one embodiment, $R^{7s}$ is alkyl, for example, a moiety of formula VII:

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, $R^{7t}$ is hydrogen; D is $NR^7$; $R^{7'}$, $R^{7l}$ and $R^{7m}$ are each alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

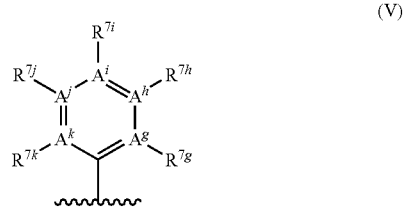

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^{7i}$ and $R^{7k}$ are each hydrogen and $R^{7j}$ is carbonyl, for example, of formula VI:

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In one embodiment, $R^{7s}$ is alkyl, for example, a moiety of formula VII:

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or CR$^{7'}$, R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m}$ are linked to form a 5- or 6-membered aryl, heterocyclic or aliphatic ring; and when D is O, R$^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

In one embodiment, R$^{7t}$ is alkyl (e.g., methyl); n is 2; D is N and R$^{7l}$ and R$^{7m}$ are each alkyl (e.g., methyl).

In one embodiment, X is CR$^{6}$R$^{6'}$; R$^{2}$, R$^{2'}$, R$^{3}$, R$^{4a}$, R$^{5}$, R$^{5'}$, R$^{6}$, R$^{6'}$, R$^{8}$, R$^{9}$, R$^{11}$, and R$^{12}$ are each hydrogen and R$^{10}$ is hydroxyl; R$^{4}$ is NR$^{4'}$R$^{4''}$ and R$^{4'}$ and R$^{4''}$ are each alkyl; R$^{7}$ is aryl, for example, of formula V:

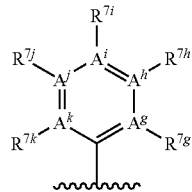

(V)

wherein

A$^{g}$, A$^{h}$, A$^{i}$, A$^{j}$ and A$^{k}$ are each independently N or C; and when A$^{g}$, A$^{h}$, A$^{i}$, A$^{j}$ and A$^{k}$ are C; R$^{7g}$, R$^{7h}$, R$^{7i}$, R$^{7j}$ and R$^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7j}$ and R$^{7i}$ are linked to form a 5- or 6-membered aryl, heterocyclic or aliphatic ring; or R$^{7g}$, R$^{7h}$, R$^{7i}$, R$^{7j}$ and R$^{7k}$ are absent when A$^{g}$, A$^{h}$, A$^{i}$, A$^{j}$ and A$^{k}$ are N.

In another embodiment, R$^{4}$ is amino (e.g., dialkylamino, for example, dimethylamino); A$^{g}$, A$^{h}$, A$^{i}$, A$^{j}$ and A$^{k}$ are each C; R$^{7g}$, R$^{7h}$ and R$^{7k}$ are each hydrogen and R$^{7i}$ and R$^{7j}$ are linked to form a 6-membered aryl ring (e.g., a benzene ring).

In one embodiment, X is CR$^{6}$R$^{6'}$; R$^{2}$, R$^{2'}$, R$^{3}$, R$^{4a}$, R$^{5}$, R$^{5'}$, R$^{6}$, R$^{6'}$, R$^{8}$, R$^{9}$, R$^{11}$, and R$^{12}$ are each hydrogen and R$^{10}$ is hydroxyl; R$^{4}$ is NR$^{4'}$R$^{4''}$ and R$^{4'}$ and R$^{4''}$ are each alkyl; R$^{7}$ is aryl, for example, of formula V:

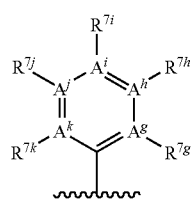

(V)

wherein

A$^{g}$, A$^{h}$, A$^{i}$, A$^{j}$ and A$^{k}$ are each independently N or C; and when A$^{g}$, A$^{h}$, A$^{i}$, A$^{j}$ and A$^{k}$ are C; R$^{7g}$, R$^{7h}$, R$^{7i}$, R$^{7j}$ and R$^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7j}$ and R$^{7i}$ are linked to form a 5- or 6-membered aryl, heterocyclic or aliphatic ring; or R$^{7g}$, R$^{7h}$, R$^{7i}$, R$^{7j}$ and R$^{7k}$ are absent when A$^{g}$, A$^{h}$, A$^{i}$, A$^{j}$ and A$^{k}$ are N.

In another embodiment, R$^{4}$ is amino (e.g., dialkylamino, for example, dimethylamino); A$^{g}$, A$^{h}$, A$^{i}$, A$^{j}$ and A$^{k}$ are each C; R$^{7g}$, R$^{7h}$, R$^{7i}$ and R$^{7k}$ are each hydrogen and R$^{7j}$ is acyl or R$^{7j}$ is carbonyl (e.g., alkoxy substituted carbonyl, for example, isopropoxycarbonyl).

In one embodiment, X is CR$^{6}$R$^{6'}$; R$^{2}$, R$^{2'}$, R$^{3}$, R$^{4a}$, R$^{5}$, R$^{5'}$, R$^{6}$, R$^{6'}$, R$^{8}$, R$^{9}$, R$^{11}$, and R$^{12}$ are each hydrogen and R$^{10}$ is hydroxyl; R$^{4}$ is NR$^{4'}$R$^{4''}$ and R$^{4'}$ and R$^{4''}$ are each alkyl; R$^{7}$ is aryl, for example, of formula V:

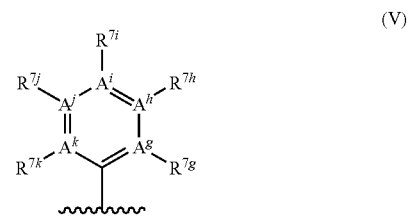

(V)

wherein

A$^{g}$, A$^{h}$, A$^{i}$, A$^{j}$ and A$^{k}$ are each independently N or C; and when A$^{g}$, A$^{h}$, A$^{i}$, A$^{j}$ and A$^{k}$ are C; R$^{7g}$, R$^{7h}$, R$^{7i}$, R$^{7j}$ and R$^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7j}$ and R$^{7i}$ are linked to form a 5- or 6-membered aryl, heterocyclic or aliphatic ring; or R$^{7g}$, R$^{7h}$, R$^{7i}$, R$^{7j}$ and R$^{7k}$ are absent when A$^{g}$, A$^{h}$, A$^{i}$, A$^{j}$ and A$^{k}$ are N.

In another embodiment, R$^{4}$ is amino (e.g., dialkylamino, for example, dimethylamino); A$^{g}$, A$^{h}$, A$^{i}$, A$^{j}$ and A$^{k}$ are each C; R$^{7g}$, R$^{7h}$, R$^{7i}$ and R$^{7k}$ are each hydrogen and R$^{7j}$ is alkenyl, for example,

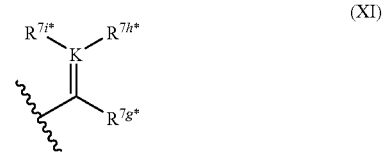

(XI)

wherein

K is C or N;

R$^{7g}$* and R$^{7h}$* are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7i}$* is hydrogen, alkyl, alkenyl, alkynyl, acyl, hydroxyl, alkoxy, thioether, sulfinyl, sulfonyl, amino, cyano, nitro, carbonyl, aryl or heterocyclic when K is C; or R$^{7i}$* is absent when K is N.

In another embodiment, K is C; R$^{7g}$* and R$^{7i}$* are each hydrogen and R$^{7h}$* is cyano.

In one embodiment, X is CR$^{6}$R$^{6'}$; R$^{2}$, R$^{2'}$, R$^{3}$, R$^{4a}$, R$^{5}$, R$^{5'}$, R$^{6}$, R$^{6'}$, R$^{8}$, R$^{9}$, R$^{11}$, and R$^{12}$ are each hydrogen and R$^{10}$ is hydroxyl; R$^{4}$ is NR$^{4'}$R$^{4''}$ and R$^{4'}$ and R$^{4''}$ are each alkyl; R$^{7}$ is aryl, for example, of formula V:

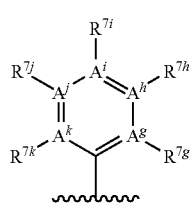

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is amino (e.g., dialkylamino, for example, dimethylamino); $A^g$, $A^h$, $A^i$, $A^j$ and $A^k$ are each C; $R^{7g}$, $R^{7h}$ and $R^{7i}$ are each hydrogen; $R^{7k}$ is halogen (e.g., fluorine); and $R^{7j}$ is carbonyl, for example, of formula VI:

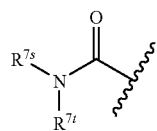

(VI)

wherein $R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In another embodiment, $R^{7t}$ is hydrogen and $R^{7s}$ is alkyl, for example, of the structure VII:

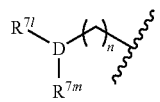

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 2; $R^{7l}$ and $R^{7m}$ are each alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

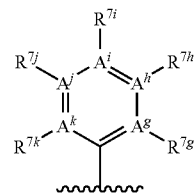

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is amino (e.g., dialkylamino, for example, dimethylamino); $A^g$, $A^h$, $A^i$, $A^j$ and $A^k$ are each C; $R^{7g}$ and $R^{7h}$ are each hydrogen; $R^{7j}$ is alkyl, for example, of the formula VII:

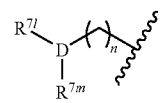

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1; $R^{7l}$ and $R^{7m}$ are each alkyl (e.g., methyl); $R^{7i}$ is hydrogen; and $R^{7k}$ is alkoxy (e.g., methoxy).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4'}$ are each alkyl; $R^7$ is aryl, for example, of formula V:

(V)

$$\begin{array}{c} R^{7i} \\ R^{7j} \diagdown A^j \diagup A^i \diagdown A^h \diagdown R^{7h} \\ \mid \qquad \mid \\ R^{7k} \diagup A^k \diagdown A^g \diagdown R^{7g} \end{array}$$

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In another embodiment, $R^4$ is amino (e.g., dialkylamino, for example, dimethylamino); $A^g$, $A^h$, $A^i$, $A^j$ and $A^k$ are each C; $R^{7g}$ and $R^{7h}$ are each hydrogen; $R^{7j}$ is alkyl, for example, of the formula VII:

(VII)

$$R^{7l} \diagdown \underset{\underset{R^{7m}}{\mid}}{D} \diagdown_n \diagdown$$

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1; $R^{7m}$ is alkyl (e.g., methyl); $R^{7l}$ is alkyl, for example, of formula VII:

(VII)

$$R^{7la} \diagdown \underset{\underset{R^{7ma}}{\mid}}{D^a} \diagdown_{n^a} \diagdown$$

wherein $D^a$ is O, N, $NR^{7a'}$ or $CR^{7a'}$;

$n^a$ is an integer from 0 to 10;

$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In another embodiment, $D^a$ is $CR^{7a'}$; $R^{7la}$ and $R^{7ma}$ are each hydrogen; $n^a$ is 0; and $R^{7a'}$ is aryl (e.g., a heteroaryl, for example, pyridinyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

(V)

$$\begin{array}{c} R^{7i} \\ R^{7j} \diagdown A^j \diagup A^i \diagdown A^h \diagdown R^{7h} \\ \mid \qquad \mid \\ R^{7k} \diagup A^k \diagdown A^g \diagdown R^{7g} \end{array}$$

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N;

In yet another embodiment, $R^4$ is amino (e.g., dialkylamino, for example, dimethylamino); $A^g$, $A^h$, $A^i$, $A^j$ and $A^k$ are each C; $R^{7g}$ and $R^{7h}$ are each hydrogen; $R^{7j}$ is alkyl, for example, of the formula VII:

(VII)

$$R^{7l} \diagdown \underset{\underset{R^{7m}}{\mid}}{D} \diagdown_n \diagdown$$

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1; $R^{7m}$ is alkyl (e.g., methyl); $R^{7l}$ is alkyl, for example, of formula VII:

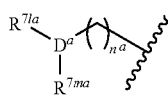
(VII)

wherein
$D^a$ is O, N, $NR^{7a'}$ or $CR^{7a'}$;
$n^a$ is an integer from 0 to 10;
$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when $D^a$ is N or $CR^{7a'}$, $R^{7la}$ and $R^{7ma}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and
when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In another embodiment, $D^a$ is $CR^{7a'}$; $R^{7la}$ and $R^{7ma}$ are each hydrogen; $n^a$ is 1 and $R^{7a'}$ is cyano.

In one embodiment, X is $CR^6R^{6'}$; $R^2, R^{2'}, R^3, R^{4a}, R^5, R^{5'}, R^6, R^{6'}, R^8, R^9, R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

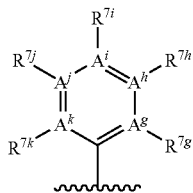
(V)

wherein
$A^g, A^h, A^i, A^j$ and $A^k$ are each independently N or C; and
when $A^g, A^h, A^i, A^j$ and $A^k$ are C; $R^{7g}, R^{7h}, R^{7i}, R^{7j}$ and $R^{7k}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or
$R^{7g}, R^{7h}, R^{7i}, R^{7j}$ and $R^{7k}$ are absent when $A^g, A^h, A^i, A^j$ and $A^k$ are N.

In yet another embodiment, $R^4$ is amino (e.g., dialkylamino, for example, dimethylamino); $A^g, A^h, A^i, A^j$ and $A^k$ are each C; $R^{7g}$ and $R^{7h}$ are each hydrogen; $R^{7j}$ is alkyl, for example, of the formula VII:

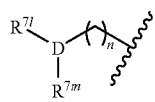
(VII)

wherein
D is O, N, $NR^{7'}$ or $CR^{7'}$;
n is an integer from 0 to 10;
$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and
when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, $D^a$ is O; $n^a$ is 2; $R^{7la}$ is alkyl (e.g., t-butyl) and $R^{7i}$ and $R^{7k}$ are each hydrogen.

In another embodiment, $R^4$ is amino (e.g., dialkylamino, for example, dimethylamino); $A^g, A^h, A^i, A^j$ and $A^k$ are each C; $R^{7g}$ and $R^{7h}$ are each hydrogen; $R^{7j}$ is alkyl, for example, of the formula VII:

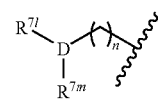
(VII)

wherein
D is O, N, $NR^{7'}$ or $CR^{7'}$;
n is an integer from 0 to 10;
$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and
when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1; $R^{7m}$ is alkyl (e.g., methyl); $R^{7l}$ is alkyl, for example, of formula VII:

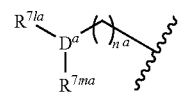
(VII)

wherein
$D^a$ is O, N, $NR^{7a'}$ or $CR^{7a'}$;
$n^a$ is an integer from 0 to 10;
$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and
when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In another embodiment, $D^a$ is $CR^{7a'}$; $R^{7a'}$ is carbonyl (e.g., aminocarbonyl); $R^{7k}$ is hydrogen and $R^{7i}$ is alkoxy (e.g., methoxy).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

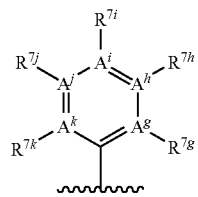

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^{7i}$ and $R^{7k}$ are each hydrogen; $R^{7j}$ is alkyl, for example, of formula VII:

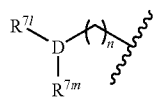

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In another embodiment, D is N; n is 1 and $R^{7l}$ is alkyl, wherein for example, of formula VII:

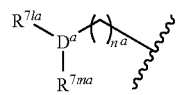

(VII)

wherein $D^a$ is O, N, $NR^{7a'}$ or $CR^{7a'}$;

$n^a$ is an integer from 0 to 10;

$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In a further embodiment, $D^a$ is N; $R^{7la}$ and $R^{7ma}$ are each alkyl (e.g., methyl); $n^a$ is 2, 3 or 4 and $R^{7m}$ is alkyl (e.g., methyl) or hydrogen.

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

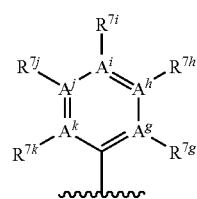

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^{7i}$ and $R^{7k}$ are each hydrogen and $R^{7j}$ is amino, for example, of formula IX:

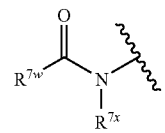

(IX)

wherein $R^{7w}$ and $R^{7x}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic.

In another embodiment, $R^{7x}$ is hydrogen and $R^{7w}$ is alkyl, for example, of formula VII:

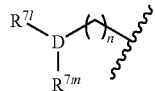

(VII)

wherein
D is O, N, $NR^{7'}$ or $CR^{7'}$;
n is an integer from 0 to 10;
$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and
when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1 or 3; $R^{7l}$ and $R^{7m}$ are each alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

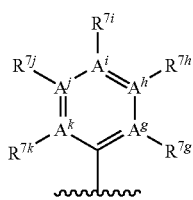

(V)

wherein
$A^g$, $A^h$, $A^i$, $A^j$ and $A^k$ are each independently N or C; and
when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or
$R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^{7i}$ and $R^{7k}$ are each hydrogen and $R^{7j}$ is amino, for example, of formula IX:

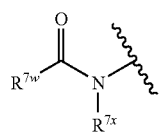

(IX)

wherein
$R^{7w}$ and $R^{7x}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic.

In another embodiment, $R^{7x}$ is hydrogen and $R^{7w}$ is alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

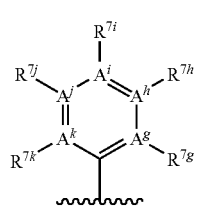

(V)

wherein
$A^g$, $A^h$, $A^i$, $A^j$ and $A^k$ are each independently N or C; and
when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or
$R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^j$ and $R^{7k}$ are each hydrogen and $R^{7i}$ is carbonyl, for example, of formula VI:

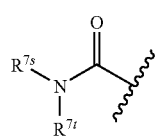

(VI)

wherein
$R^{7s}$ and $R^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s}$ and $R^{7t}$ are linked to form a 5- or 6-membered aryl, heterocyclic or aliphatic ring.

In another embodiment, $R^{7t}$ is hydrogen and $R^{7s}$ is alkyl, for example of formula VII:

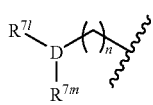

(VII)

wherein
D is O, N, $NR^{7'}$ or $CR^{7'}$;
n is an integer from 0 to 10;
$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In another embodiment, D is N; $R^{7l}$ and $R^{7m}$ are each alkyl (e.g., methyl) and n is 2 or 3.

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

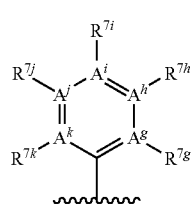

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^j$ and $R^{7k}$ are each hydrogen and $R^{7i}$ is alkyl, for example, of formula VII:

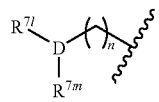

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In another embodiment, D is N; n is 1; $R^{7m}$ is hydrogen and $R^{7l}$ is alkyl, for example, of formula VII:

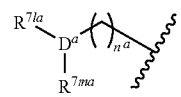

(VII)

wherein $D^a$ is O, N, $NR^{7a'}$ or $CR^{7a'}$;

$n^a$ is an integer from 0 to 10;

$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In a further embodiment, $D^a$ is $CR^{7a'}$; $n^a$ is 0; $R^{7la}$ and $R^{7ma}$ are each hydrogen and $R^{7a'}$ is aryl, for example, phenyl (e.g., p-substituted alkoxy phenyl such as methoxy phenyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

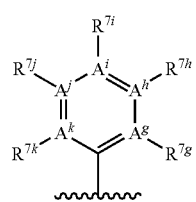

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^j$ and $R^{7k}$ are each hydrogen and $R^{7i}$ is alkyl, for example, of formula VII:

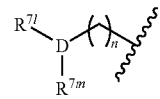

(VII)

wherein

D is O, N, $NR^{7'}$ or $CR^{7'}$;

n is an integer from 0 to 10;

$R^{7\prime}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7\prime}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In another embodiment, D is N; n is 1; $R^{7m}$ is hydrogen and $R^{7l}$ is alkyl, for example, of formula VII:

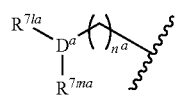

(VII)

wherein $D^a$ is O, N, $NR^{7a\prime}$ or $CR^{7a\prime}$;

$n^a$ is an integer from 0 to 10;

$R^{7a\prime}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a\prime}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In a further embodiment, $D^a$ is O; $n^a$ is 2 and $R^{7la}$ is alkyl (e.g., methyl).

In one embodiment, X is $CR^6R^{6\prime}$; $R^2$, $R^{2\prime}$, $R^3$, $R^{4a}$, $R^5$, $R^{5\prime}$, $R^6$, $R^{6\prime}$, $R^8$, $R^9$, $R^{11}$, and $R^{12}$ are each hydrogen and $R^{10}$ is hydroxyl; $R^4$ is $NR^{4\prime}R^{4\prime\prime}$ and $R^{4\prime}$ and $R^{4\prime\prime}$ are each alkyl; $R^7$ is aryl, for example, of formula V:

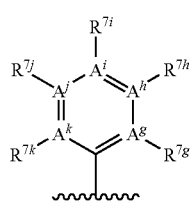

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^j$ and $R^{7k}$ are each hydrogen and $R^{7i}$ is carbonyl (e.g., alkoxycarbonyl such as methoxycarbonyl).

In one embodiment, X is $CR^6R^{6\prime}$; $R^2$, $R^{2\prime}$, $R^3$, $R^{4a}$, $R^5$, $R^{5\prime}$, $R^6$, $R^{6\prime}$, $R^8$, $R^9$, $R^{11}$, and $R^{12}$ are each hydrogen and $R^{10}$ is hydroxyl; $R^4$ is $NR^{4\prime}R^{4\prime\prime}$ and $R^{4\prime}$ and $R^{4\prime\prime}$ are each alkyl; $R^7$ is aryl, for example, of formula V:

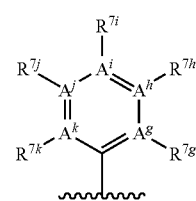

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^g$, $A^h$, $A^i$, $A^j$ and $A^k$ are each C; $R^{7g}$, $R^{7h}$, $R^j$ and $R^{7k}$ are each hydrogen and $R^{7i}$ is amino, for example, of formula IX:

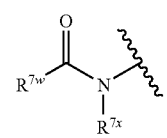

(IX)

wherein $R^{7w}$ and $R^{7x}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic.

In one embodiment, $R^{7x}$ is hydrogen and $R^{7w}$ is alkyl, for example, of formula VII:

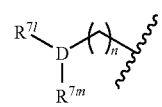

(VII)

wherein

D is O, N, $NR^{7\prime}$ or $CR^{7\prime}$;

n is an integer from 0 to 10;

$R^{7\prime}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7\prime}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1 and $R^{7l}$ and $R^{7m}$ are each alkyl (e.g., methyl). Alternatively, $R^{7m}$ is hydrogen and $R^{7l}$ is alkyl (e.g., methyl).

In one embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is aryl, for example, of formula V:

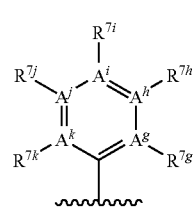

(V)

wherein $A^g$, $A^h$, $A^i$, $A^j$ and $A^k$ are each independently N or C; and when $A^g$, $A^h$, $A^i$, $A^j$ and $A^k$ are C; $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or $R^{7g}$, $R^{7h}$, $R^{7i}$, $R^{7j}$ and $R^{7k}$ are absent when $A^g$, $A^h$, $A^i$, $A^j$ and $A^k$ are N.

In yet another embodiment, $R^4$ is amino (e.g., dialkylamino, for example, dimethylamino); $A^h$ is N; $A^g$, $A^i$, $A^j$ and $A^k$ are C; $R^{7g}$, $R^{7j}$ and $R^{7k}$ are each hydrogen and $R^{7i}$ is alkoxy, for example, of formula VIII:

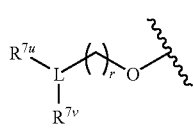

(VIII)

wherein

L is O, N, $NR^{7''}$ or $CR^{7''}$;

r is an integer from 0 to 10;

$R^{7''}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when L is N or $CR^{7''}$, $R^{7u}$ and $R^{7v}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7u}$ and $R^{7v}$ are linked to form a 5- or 6-membered aryl, heterocyclic or aliphatic ring; or when L is O, $R^{7u}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7v}$ is absent.

In one embodiment, L is N; $R^{7u}$ and $R^{7v}$ are each alkyl (e.g., methyl) and r is 3.

In another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is —C(=W')$WR^{7a}$; W' is O; W is $NR^{7b}$; $R^{7a}$ is hydrogen and $R^{7b}$ is alkyl (e.g., aminoalkyl, for example,

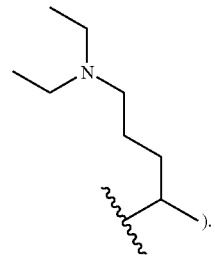

).

In another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is —C(=W')$WR^{7a}$; W' is O; W is $CR^{7d}R^{7e}$; and $R^{7d}$ and $R^{7e}$ are each hydrogen and $R^{7a}$ is alkyl, for example, of formula VII:

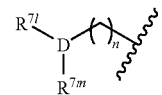

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 0; $R^{7m}$ is hydrogen and $R^{7l}$ is tetrahydrofuran or alkyl, for example, —$CH_2(CH_3)_3$; aryl substituted alkyl (e.g., a heteroaryl substituted alkyl, for example, pyridine substituted alkyl, furanyl substituted alkyl, pyrrolyl substituted alkyl, imidazolyl substituted alkyl or dihydroimidazolyl substituted alkyl, such as

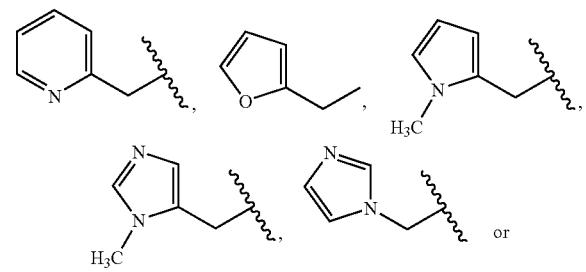

or

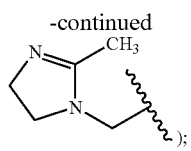

aminocarbonyl substituted alkyl (e.g., —CH$_2$(C=O)NH$_2$); halogen substituted alkyl (e.g., fluorine substituted alkyl, for example, —CH$_2$CF$_3$);

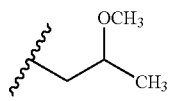

or alkoxyalkyl (e.g., methoxyethyl).

Alternatively, R$^{7l}$ is aryl (e.g., heteroaryl, for example, pyridinyl) or alkenyl, for example, of formula XI:

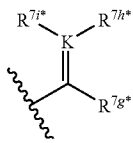

(XI)

wherein

K is C or N;

R$^{7g*}$ and R$^{7h*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7i*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when K is C; or R$^{7i*}$ is absent when K is N.

In one embodiment, K is C and R$^{7g*}$, R$^{7i*}$ and R$^{7h*}$ are each hydrogen.

In another embodiment, X is CR$^6$R$^{6'}$; R$^2$, R$^{2'}$, R$^3$, R$^{4a}$, R$^5$, R$^{5'}$, R$^6$, R$^{6'}$, R$^8$, R$^9$, R$^{11}$, and R$^{12}$ are each hydrogen and R$^{10}$ is hydroxyl; R$^4$ is NR$^{4'}$R$^{4''}$ and R$^{4'}$ and R$^{4''}$ are each alkyl; R$^7$ is —C(=W')WR$^{7a}$; W' is O; W is CR$^{7d}$R$^{7e}$; and R$^{7d}$ and R$^{7e}$ are each hydrogen and R$^{7a}$ is alkyl, for example, of formula VII:

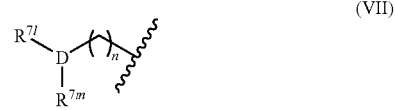

(VII)

wherein

D is O, N, NR$^{7'}$ or CR$^{7'}$;

n is an integer from 0 to 10;

R$^{7'}$ hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or CR$^{7'}$, R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m}$ are linked to form a 5- or 6-membered aryl, heterocyclic or aliphatic ring; and when D is O, R$^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

In a further embodiment, D is N; n is 0; R$^{7m}$ is alkyl (e.g., methyl) and R$^{7l}$ is alkyl (e.g., isopropyl or alkoxyalkyl, for example, methoxymethyl).

In another embodiment, X is CR$^6$R$^{6'}$; R$^2$, R$^{2'}$, R$^3$, R$^{4a}$, R$^5$, R$^{5'}$, R$^6$, R$^{6'}$, R$^8$, R$^9$, R$^{11}$, and R$^{12}$ are each hydrogen and R$^{10}$ is hydroxyl; R$^4$ is NR$^{4'}$R$^{4''}$ and R$^{4'}$ and R$^{4''}$ are each alkyl; R$^7$ is —C(=W')WR$^{7a}$; W' is O; W is CR$^{7d}$R$^{7e}$; and R$^{7d}$ and R$^{7e}$ are each hydrogen and R$^{7a}$ is alkyl, for example, of formula VII:

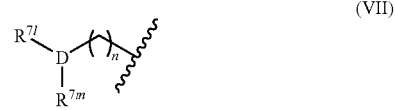

(VII)

wherein

D is O, N, NR$^{7'}$ or CR$^{7'}$;

n is an integer from 0 to 10;

R$^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or CR$^{7'}$, R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m}$ are linked to form a 5- or 6-membered aryl, heterocyclic or aliphatic ring; and when D is O, R$^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

In a further embodiment, D is N; n is O and R$^{7m}$ and R$^{7l}$ are linked to form a 6-membered heterocyclic ring, for example, piperidinyl ring (e.g.,

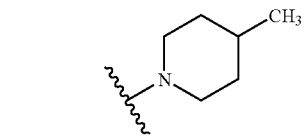

or a piperazinyl ring (e.g., an N-substituted piperazinyl ring, for example, substituted with alkyl (e.g., methyl, cyclohexyl or isopropyl), carbonyl (e.g., ethoxycarbonyl) or acyl such as

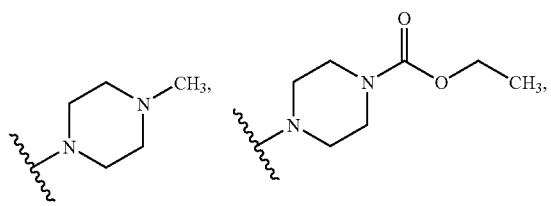

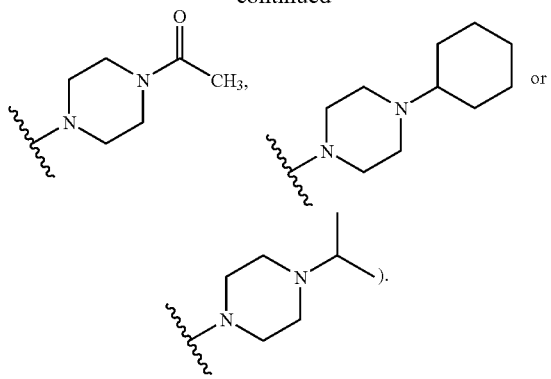

In another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is —C(=W')$WR^{7a}$; W' is O; W is $CR^{7d}R^{7e}$; and $R^{7d}$ and $R^{7e}$ are each hydrogen and $R^{7a}$ is alkyl, for example, of formula VII:

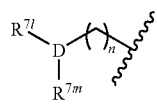

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is N; n is 1; $R^{7m}$ is hydrogen and $R^{7l}$ is acyl. Alternatively, $R^{7m}$ and $R^{7l}$ are each alkyl (e.g., methyl).

In another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; $R^7$ is —C(=W')$WR^{7a}$; W' is O; W is $CR^{7d}R^{7e}$; and $R^{7d}$ and $R^{7e}$ are each hydrogen and $R^{7a}$ is alkyl, for example, of formula VII:

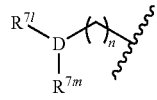

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In a further embodiment, D is O; n is O and $R^{7l}$ is alkyl (e.g., methyl).

In another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is

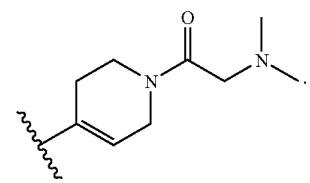

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is alkyl, for example, of formula VII:

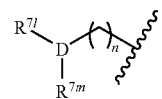

(VII)

wherein

D is O, N, $NR^{7'}$ or $CR^{7'}$;

n is an integer from 0 to 10;

$R^{7'}$ hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, D is N; n is 1 and $R^{7l}$ and $R^{7m}$ are linked to form a 6-membered heterocyclic ring, for example, a piperidinyl ring (e.g., a piperidinyl ring substituted with carbonyl, for example, is

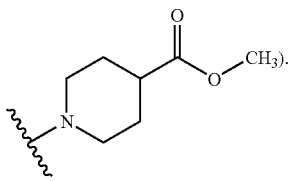

Alternatively, $R^{7m}$ is hydrogen and $R^{7l}$ is alkyl, for example, aminoalkyl such as dimethylaminobutyl).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is alkyl, for example, of formula VII:

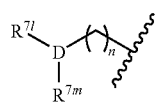
(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, D is N; n is 2 and $R^{7l}$ and $R^{7m}$ are each alkyl (e.g., methyl).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is aryl, for example, of formula X:

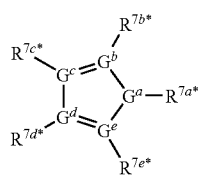
(X)

wherein $G^a$ is N, O, S or $CR^{7f*}$;

$G^b$, $G^c$, $G^d$ and $G^e$ are each independently N or $CR^{7f*}$ $R^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

$R^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^a$ is N or $CR^{7f*}$ or $R^{7a*}$ is absent when $G^a$ is O or S;

$R^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^b$ is $CR^{7f*}$ or $R^{7b*}$ is absent when $G^b$ is N;

$R^{7c*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^c$ is $CR^{7f*}$ or $R^{7c*}$ is absent when $G^c$ is N;

$R^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7d*}$ is covalently bonded to the 7-position of the tetracycline compound when $G^d$ is $CR^{7f*}$; or $R^{7d}$ is absent when $G^d$ is N; and $R^{7e*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7e*}$ is covalently bonded to the 7-position of the tetracycline compound when $G^e$ is $CR^{7f*}$ or $R^{7e*}$ is absent when $G^e$ is N;

provided that one of $R^{7d*}$ or $R^{7e*}$ are covalently bonded to the 7-position of the tetracycline compound.

In one embodiment, $G_b$, $G^c$, $G^d$ and $G^e$ are each C; $R^{7d*}$ is covalently bonded to the 7-position of the tetracycline compound; $G^a$ is O; $R^{7c*}$ and $R^{7e*}$ are each hydrogen and $R^{7d*}$ is alkyl, for example, of formula VII:

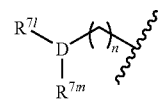
(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, n is 1; D is N and $R^{7l}$ and $R^{7m}$ are linked to form a 6-membered heterocyclic ring (e.g., a piperidinyl ring).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is aryl, for example, of formula X:

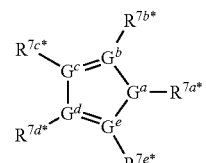
(X)

wherein

G$^a$ is N, O, S or CR$^{7f*}$;

G$^b$, G$^c$, G$^d$ and G$^e$ are each independently N or CR$^{7f*}$;

R$^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

R$^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^a$ is N or CR$^{7f*}$ or R$^{7a*}$ is absent when G$^a$ is O or S;

R$^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^b$ is CR$^{7f*}$ or R$^{7b*}$ is absent when G$^b$ is N;

R$^{7c*}$ hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^c$ is CR$^{7f*}$ or R$^{7c*}$ is absent when G$^c$ is N;

R$^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7d*}$ is covalently bonded to the 7-position of the tetracycline compound when G$^d$ is CR$^{7f*}$; or R$^{7d}$ is absent when G$^d$ is N; and R$^{7e*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7e*}$ is covalently bonded to the 7-position of the tetracycline compound when G$^e$ is CR$^{7f*}$ or R$^{7e*}$ is absent when G$^e$ is N;

provided that one of R$^{7d*}$ or R$^{7e*}$ are covalently bonded to the 7-position of the tetracycline compound.

In one embodiment, G$^b$, G$^c$, G$^d$ and G$^e$ are each C; R$^{7e*}$ is covalently bonded to the 7-position of the tetracycline compound; G$^a$ is N; R$^{7a*}$ is hydrogen; R$^{7c*}$ and R$^{7d*}$ are each hydrogen and R$^{7b*}$ is alkyl, for example, of formula VII:

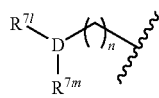

(VII)

wherein

D is O, N, NR$^{7'}$ or CR$^{7'}$;

n is an integer from 0 to 10;

R$^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or CR$^{7'}$, R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m}$ are linked to form a 5- or 6-membered aryl, heterocyclic or aliphatic ring; and when D is O, R$^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

In one embodiment, n is 1; D is N and R$^{7l}$ and R$^{7m}$ are each alkyl (e.g., methyl).

In yet another embodiment, X is CR$^6$R$^{6'}$; R$^2$, R$^{2'}$, R$^3$, R$^{4a}$, R$^5$, R$^{5'}$, R$^6$, R$^{6'}$, R$^8$, R$^9$, R$^{11}$, and R$^{12}$ are each hydrogen and R$^{10}$ is hydroxyl; R$^4$ is NR$^{4'}$R$^{4''}$ and R$^{4'}$ and R$^{4''}$ are each alkyl; and R$^7$ is aryl, for example, of formula X:

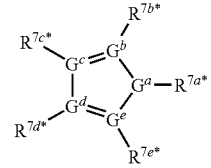

(X)

wherein

G$^a$ is N, O, S or CR$^{7f*}$;

G$^b$, G$^c$, G$^d$ and G$^e$ are each independently N or CR$^{7f*}$;

R$^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

R$^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^a$ is N or CR$^{7f*}$ or R$^{7a*}$ is absent when G$^a$ is O or S;

R$^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^b$ is CR$^{7f*}$ or R$^{7b*}$ is absent when G$^b$ is N;

R$^{7c*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^c$ is CR$^{7f*}$ or R$^{7c*}$ is absent when G$^c$ is N;

R$^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7d*}$ is covalently bonded to the 7-position of the tetracycline compound when G$^d$ is CR$^{7f*}$; or R$^{7d*}$ is absent when G$^d$ is N; and R$^{7e*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7e*}$ is covalently bonded to the 7-position of the tetracycline compound when G$^e$ is CR$^{7f*}$ or R$^{7e*}$ is absent when G$^e$ is N;

provided that one of R$^{7d*}$ or R$^{7e*}$ are covalently bonded to the 7-position of the tetracycline compound.

In one embodiment, G$^b$, G$^c$, G$^d$ and G$^e$ are each C; R$^{7e*}$ is covalently bonded to the 7-position of the tetracycline compound; G$^a$ is O; R$^{7b*}$ and R$^{7c*}$ are each hydrogen. R$^{7d*}$ is alkyl, for example, of formula VII:

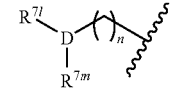

(VII)

wherein

D is O, N, NR$^{7'}$ or CR$^{7'}$;

n is an integer from 0 to 10;

R$^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or CR$^{7'}$, R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m}$ are linked to form a 5- or 6-membered aryl, heterocyclic or aliphatic ring; and when D is O, R$^{7l}$ hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

In one embodiment, n is 1; D is N; $R^{7m}$ is H; and $R^{7l}$ alkyl, for example, of formula VII:

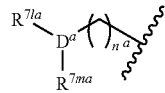

(VII)

wherein $D^a$ is O, N, $NR^{7a'}$ or $CR^{7a'}$ $n^a$ is an integer from 0 to 10;

$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In a further embodiment, $n^a$ is 2; $D^a$ is O; $R^{7la}$ is alkyl (e.g., methyl).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is aryl, for example, of formula X:

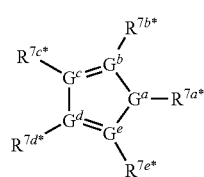

(X)

wherein $G^a$ is N, O, S or $CR^{7f*}$;

$G^b$, $G^c$, $G^d$ and $G^e$ are each independently N or $CR^{7f*}$;

$R^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

$R^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^a$ is N or $CR^{7f*}$ or $R^{7a*}$ is absent when $G^a$ is O or S;

$R^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^b$ is $CR^{7f*}$ or $R^{7b*}$ is absent when $G^b$ is N;

$R^{7c*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^c$ is $CR^{7f*}$ or $R^{7c*}$ is absent when $G^c$ is N;

$R^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7d*}$ is covalently bonded to the 7-position of the tetracycline compound when $G^d$ is $CR^{7f*}$; or $R^{7d*}$ is absent when $G^d$ is N; and $R^{7e*}$ hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7e*}$ is covalently bonded to the 7-position of the tetracycline compound when $G^e$ is $CR^{7f*}$ or $R^{7e*}$ is absent when $G^e$ is N;

provided that one of $R^{7d*}$ or $R^{7e*}$ are covalently bonded to the 7-position of the tetracycline compound.

In one embodiment, $G^b$, $G^c$, $G^d$ and $G^e$ are each C; $R^{7e*}$ is covalently bonded to the 7-position of the tetracycline compound; $G^a$ is O; $R^{7c*}$ and $R^{7d*}$ are each hydrogen and $R^{7b*}$ is alkyl, for example, of formula VII:

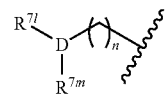

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, n is 1; D is N and $R^{7l}$ and $R^{7m}$ are linked to form a 6-membered heterocyclic ring, for example, a morpholinyl or piperazinyl ring (e.g., an N-substituted piperazinyl ring, such as N-methyl substituted piperazinyl ring, for example,

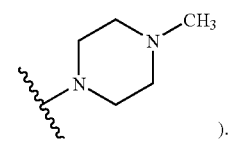

).

Alternatively, $R^{7m}$ is hydrogen and $R^{7l}$ is alkyl, for example, aryl substituted alkyl (e.g., a heteroaryl substituted alkyl, for example, pyridine substituted alkyl such as

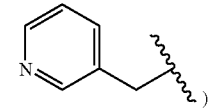

)

or $R^{7l}$ is alkyl of formula VII:

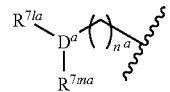

(VII)

wherein $D^a$ is O, N, $NR^{7a'}$ or $CR^{7a'}$;

$n^a$ is an integer from 0 to 10;

$R^{7a'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when $D^a$ is N or $CR^{7a'}$, $R^{7la}$ and $R^{7ma}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7la}$ and $R^{7ma}$ are linked to form a 5- or 6-membered aryl, heterocyclic or aliphatic ring; and when $D^a$ is O, $R^{7la}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7ma}$ is absent.

In one embodiment, $n^a$ is 2; D is N; $R^{7la}$ and $R^{7ma}$ is alkyl (e.g., methyl) and $R^{7l}$ is hydrogen or alkyl (e.g., methyl).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is aryl, for example, of formula X:

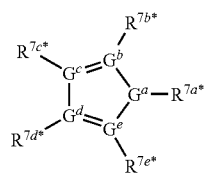

(X)

wherein $G^a$ is N, O, S or $CR^{7f*}$;

$G^b$, $G^c$, $G^d$ and $G^e$ are each independently N or $CR^{7f*}$ $R^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;

$R^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^a$ is N or $CR^{7f*}$ or $R^{7a*}$ is absent when $G^a$ is O or S;

$R^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^b$ is $CR^{7f*}$ or $R^{7b*}$ is absent when $G^b$ is N;

$R^{7c*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when $G^c$ is $CR^{7f*}$ or $R^{7c*}$ is absent when $G^c$ is N;

$R^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7d*}$ is covalently bonded to the 7-position of the tetracycline compound when $G^d$ is $CR^{7f*}$; or $R^{7d*}$ is absent when $G^d$ is N; and $R^{7e*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7e*}$ is covalently bonded to the 7-position of the tetracycline compound when $G^e$ is $CR^{7f}$ or $R^{7e*}$ is absent when $G^e$ is N;

provided that one of $R^{7d*}$ or $R^{7e*}$ are covalently bonded to the 7-position of the tetracycline compound.

In one embodiment, $G^b$, $G^c$, $G^d$ and $G^e$ are each C; $R^{7e*}$ is covalently bonded to the 7-position of the tetracycline compound; $G^a$ is O; $R^{7c*}$ and $R^{7d*}$ are each hydrogen and $R^{7b*}$ is alkenyl, for example, of formula XI:

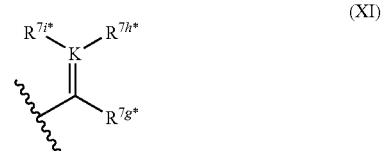

(XI)

wherein

K is C or N;

$R^{7g*}$ and $R^{7h*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and $R^{7i*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when K is C; or $R^{7i*}$ is absent when K is N.

In one embodiment, $R^{7g*}$ is hydrogen; K is N and $R^{7h*}$ is alkoxy (e.g., methoxy).

In yet another embodiment, X is $CR^6R^{6'}$; $R^2$, $R^{2'}$, $R^3$, $R^{4a}$, $R^5$, $R^{5'}$, $R^6$, $R^{6'}$, $R^8$, $R^9$, $R^{11}$, and $R^{12}$ are each hydrogen and $R^{10}$ is hydroxyl; $R^4$ is $NR^{4'}R^{4''}$ and $R^{4'}$ and $R^{4''}$ are each alkyl; and $R^7$ is

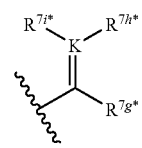

(XI)

wherein

K is C or N;

$R^{7g*}$ and $R^{7h*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and $R^{7i*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when K is C; or $R^{7i*}$ is absent when K is N.

In one embodiment, K is N; $R^{7h*}$ is alkoxy (e.g., t-butyoxy) and $R^{7g*}$ is alkyl, for example, of formula VII:

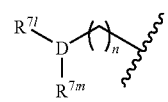

(VII)

wherein

D is O, N, $NR^{7'}$ or $CR^{7'}$;

n is an integer from 0 to 10;

$R^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and when D is N or $CR^{7'}$, $R^{7l}$ and $R^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7l}$ and $R^{7m}$ are linked to form a 5- or 6-membered aryl, heterocyclic or aliphatic ring; and when D is O, $R^{7l}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and $R^{7m}$ is absent.

In one embodiment, D is N; n is 2 and $R^{7l}$ and $R^{7m}$ are each alkyl (e.g., methyl).

In another embodiment, the tetracycline compound is of formula XII:

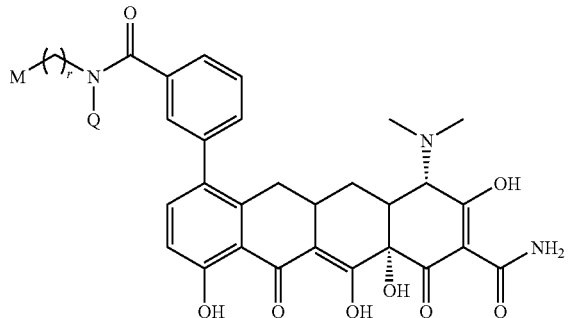

(XII)

wherein
r is an integer from 1 to 10;
M is $OR^{7o*}$ or $NR^{7p*}R^{7q*}$;
Q is hydrogen or alkyl;
$R^{7o*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7p*}$ and $R^{7q*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7p*}$ and $R^{7q*}$ are linked to form a 5- or 6-membered aryl, heterocyclic or aliphatic ring.

In yet another embodiment, the tetracycline compound is of formula XIII:

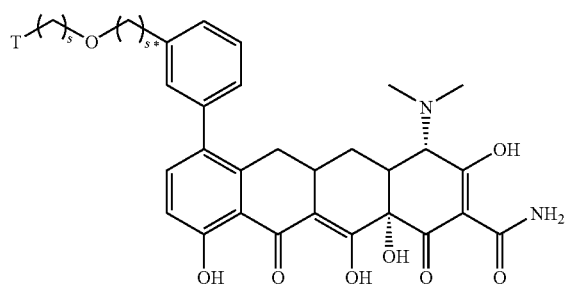

(XIII)

wherein
s and s* are each independently an integer from 1 to 10;
T is $OR^{7r*}$ or $NR^{7s*}R^{7t*}$;
$R^{7r*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7s*}$ and $R^{7t*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7s*}$ and $R^{7t*}$ are linked to form a 5- or 6-membered aryl, heterocyclic or aliphatic ring.

In one embodiment, the tetracycline compound is of formula XIV:

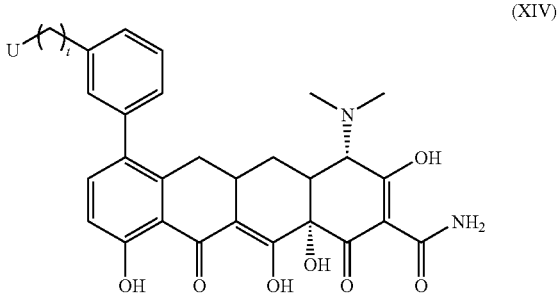

(XIV)

wherein
t is an integer from 1 to 10;
U is $OR^{7u*}$ or $NR^{7v*}R^{7w*}$;
$R^{7u*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7v*}$ and $R^{7w*}$ are each hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7v*}$ and $R^{7w*}$ are linked to form a 5- or 6-membered aryl, heterocyclic or aliphatic ring.

In another embodiment, the tetracycline compound is of formula XV:

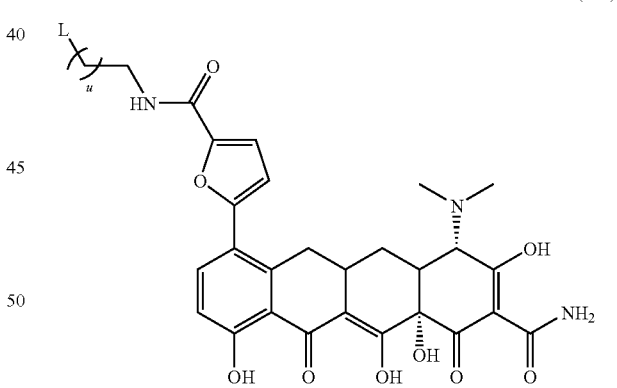

(XV)

wherein
u is an integer from 1 to 10;
L is $OR^{7x*}$ or $NR^{7y*}R^{7z*}$;
$R^{7x*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7y*}$ and $R^{7z*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7y*}$ and $R^{7z*}$ are linked to form a 5- or 6-membered aryl, heterocyclic or aliphatic ring.

In one embodiment, the tetracycline compound is of formula XVI:

(XVI)

wherein v and v* are each independently an integer from 1 to 10;

T is OR$^{7b}$ or NR$^{7c}$R$^{7d**}$;

R$^{7b}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7c}$ and R$^{7d}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7c}$ and R$^{7d**}$ are linked to form a 5- or 6-membered aryl, heterocyclic or aliphatic ring.

In another embodiment, the tetracycline compound is of formula XVII:

(XVII)

wherein x and x* are each independently an integer from 1 to 10;

A* is OR$^{7e}$ or NR$^{7f}$ R$^{7g**}$

D* is NH, NCH$_3$, O, CH$_2$;

R$^{7e}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7f}$ and R$^{7g}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; or R$^{7f}$ and R$^{7g**}$ are linked to form a 5- or 6-membered aryl, heterocyclic or aliphatic ring.

In a further embodiment, the tetracycline compound is of XVIII:

(XVIII)

wherein u is an integer from 1 to 10;

G* is OR$^{7h}$ or NR$^{7i}$R$^{7i**}$;

E* is NH, NCH$_3$, O, CH$_2$;

R$^{7h}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7i}$ and R$^{7j}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7i}$ and R$^{7j**}$ are linked to form a 5- or 6-membered aryl, heterocyclic or aliphatic ring.

In yet another embodiment, the tetracycline compound is of formula XIX:

(XIX)

wherein y is an integer from 1 to 10;

K* is OR$^{7k*}$ or NR$^{7l}$R$^{7m**}$;

J* is NH, NCH$_3$, O, CH$_2$;

R$^{7k}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and R$^{7l}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7l}$ and R$^{7m**}$ are linked to form a 5- or 6-membered aryl, heterocyclic or aliphatic ring.

In another embodiment, the tetracycline compound is of formula (XX)

wherein W" is $CR^{7d''}R^{7e''}$, S, $NR^{7b''}$ or O; and $R^{7a''}$, $R^{7b''}$, $R^{7c''}$, $R^{7d''}$ and $R^{7e''}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7a''}$ and $R^{7c''}$ are linked together to form a 5- or 6-membered aryl, heterocyclic or aliphatic ring; and pharmaceutically acceptable salts thereof.

Examples of tetracycline compounds include:

A

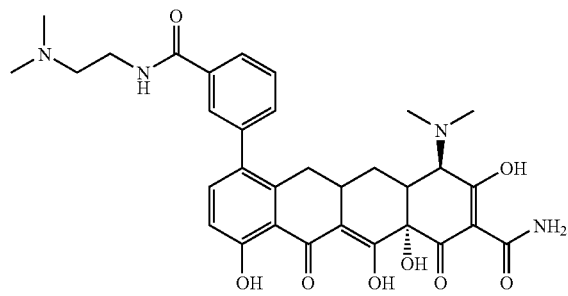

B

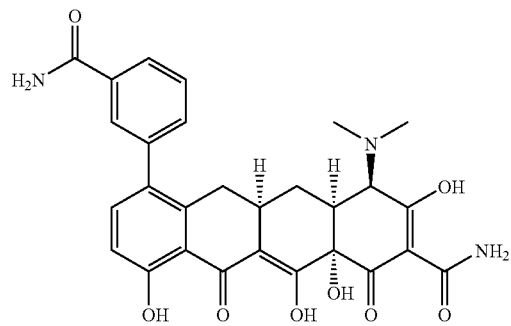

C

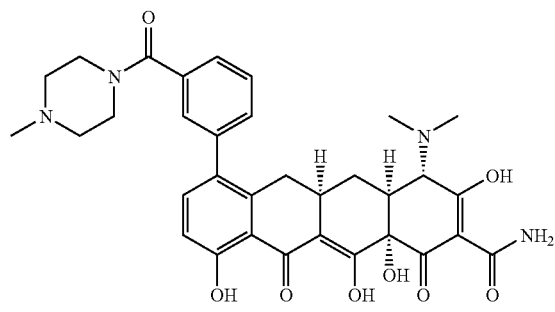

D

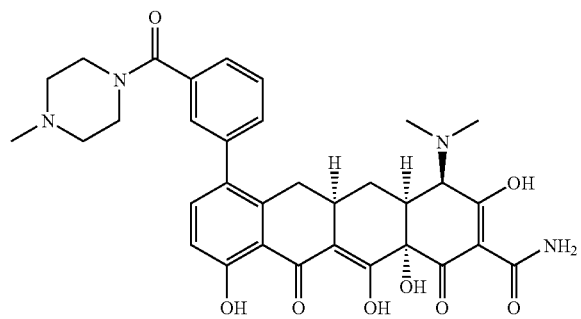

E

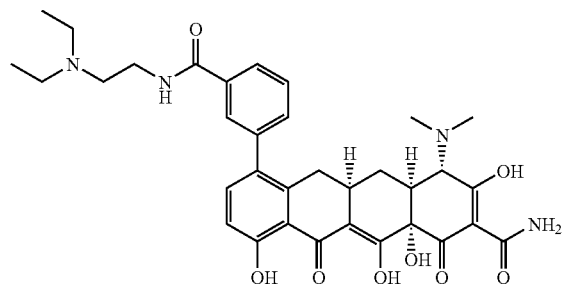

F

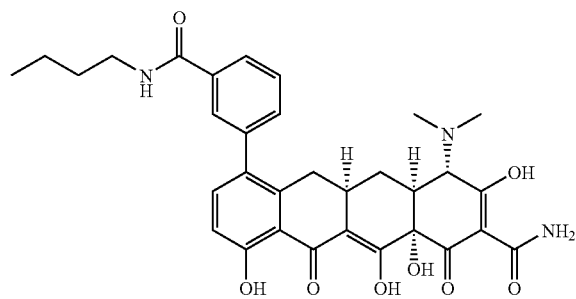

G

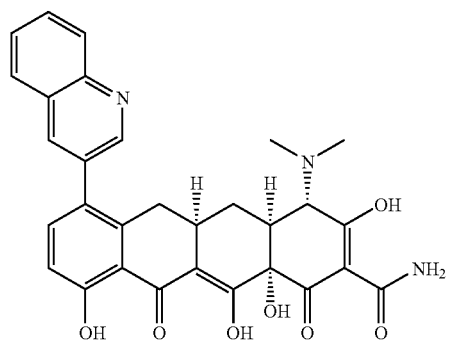

H

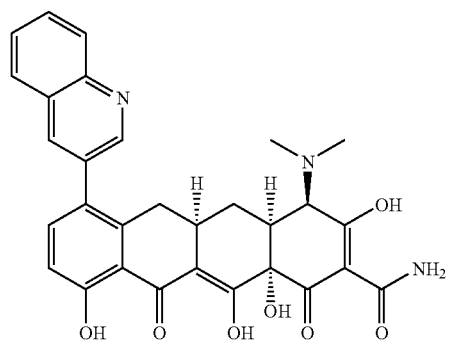

-continued
I
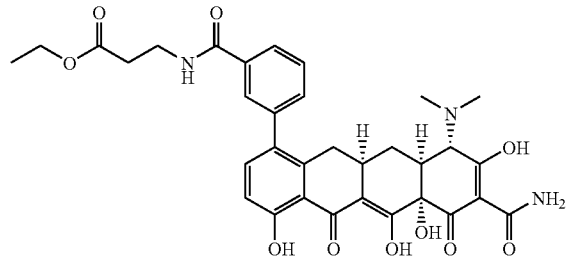
J
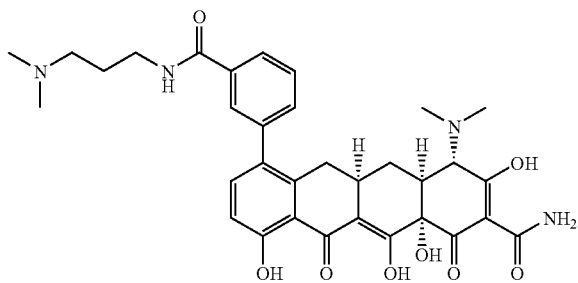
K
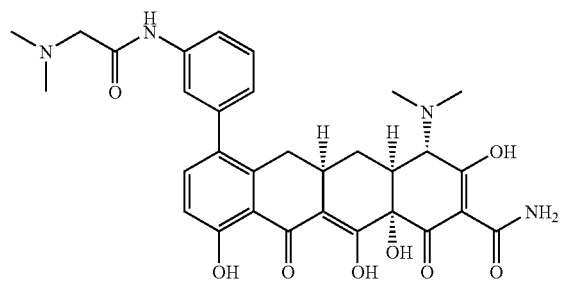
L
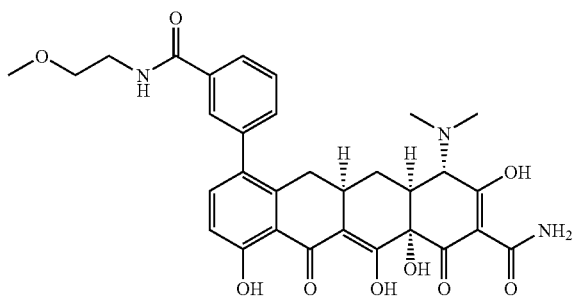
M
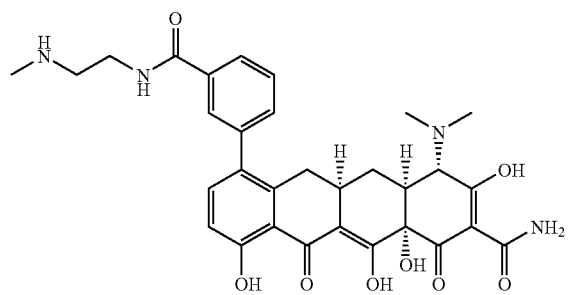
N
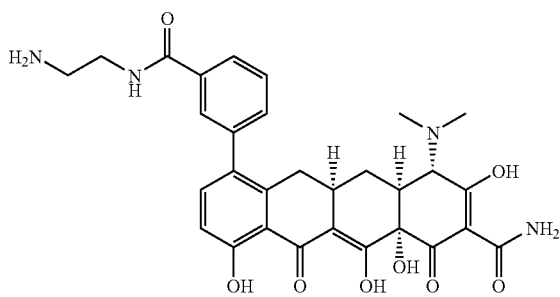
O
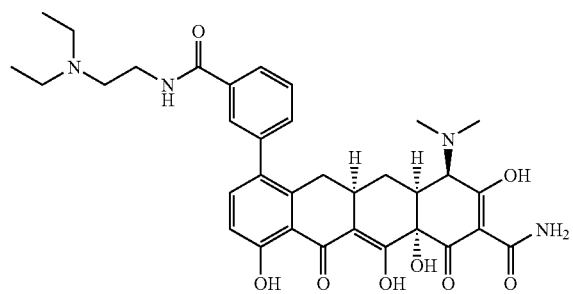
P
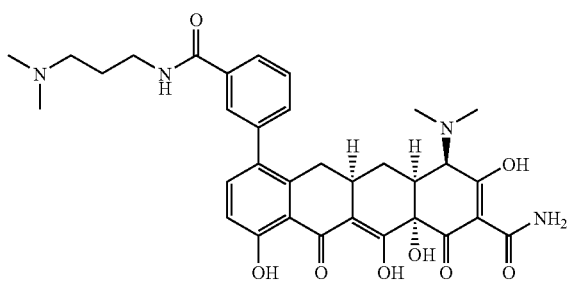
Q
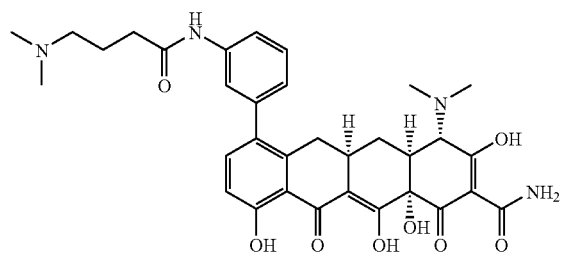
R
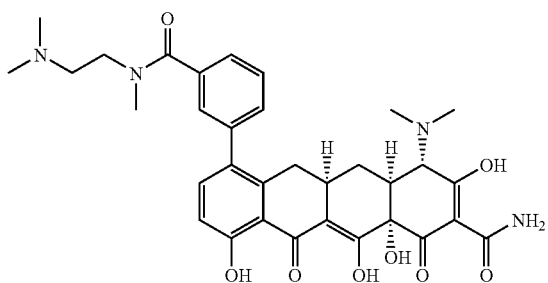

-continued
S
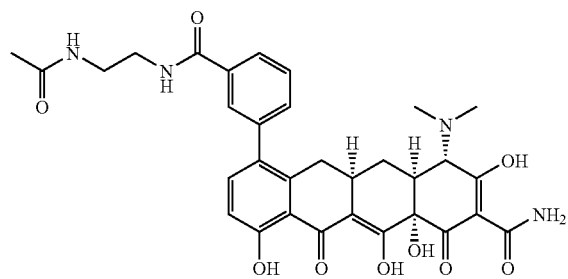
T
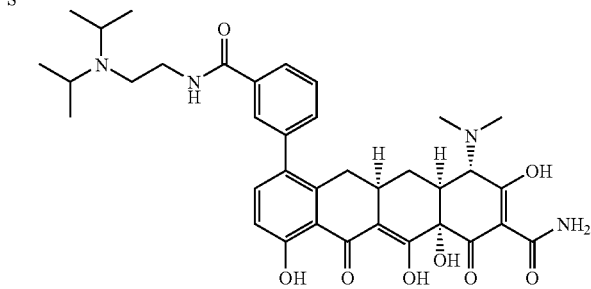
U
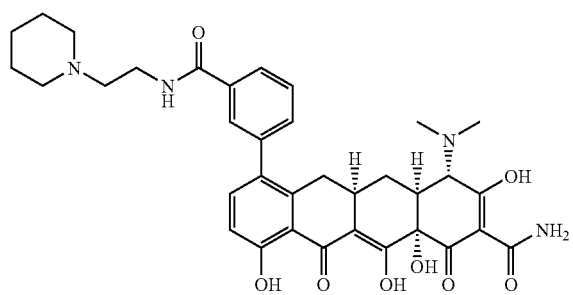
V
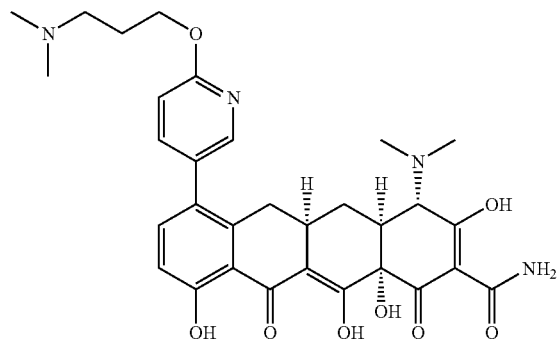
W
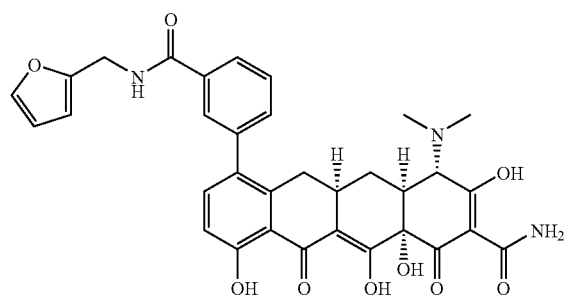
X
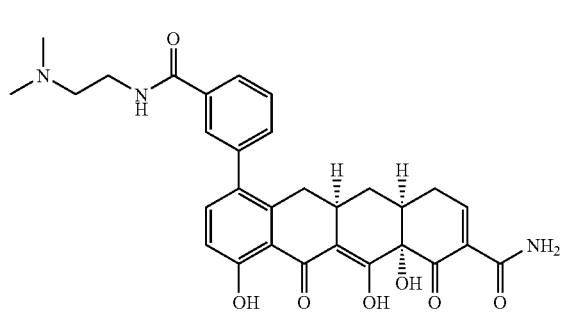
Y
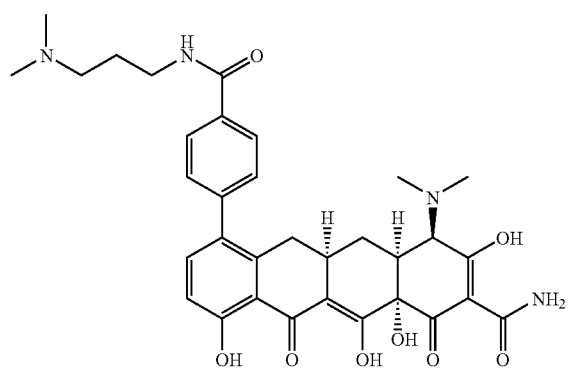
Z
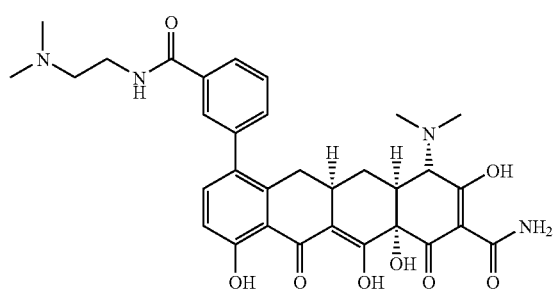
AA
AB -continued
AC
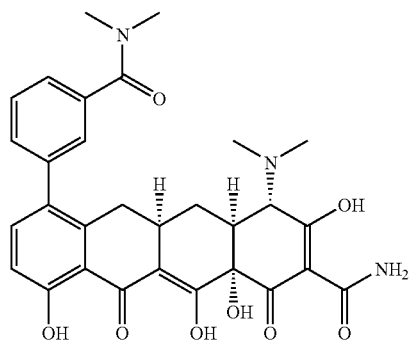
AD
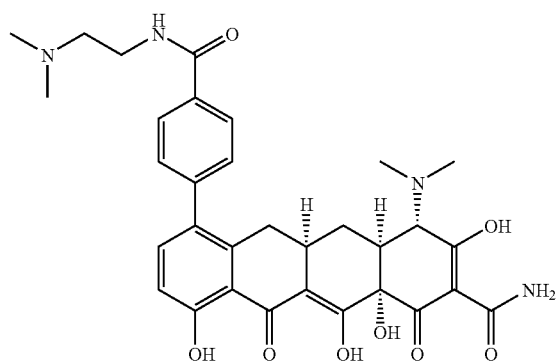
AE
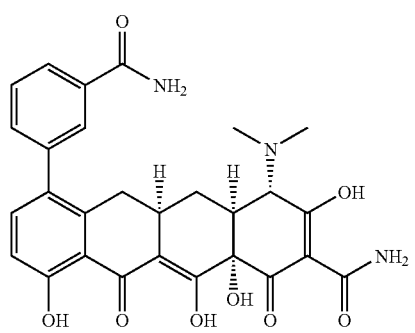
AF
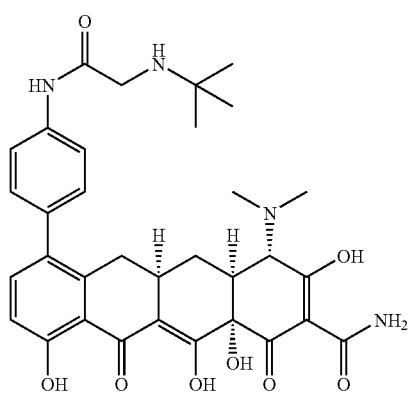
AG
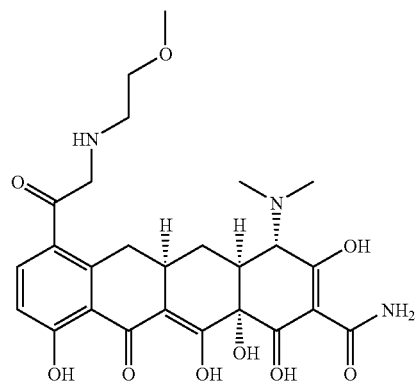
AH
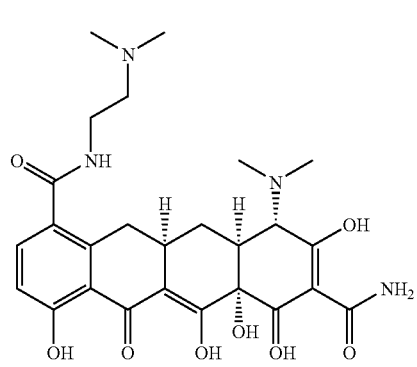
AI
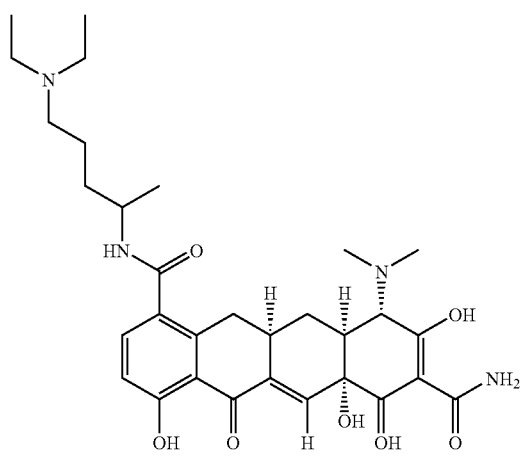
AJ
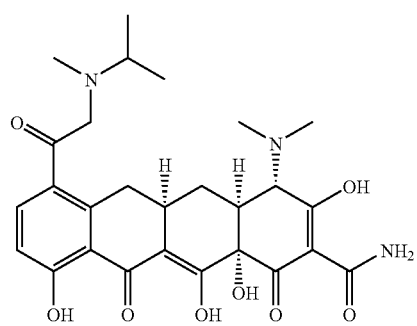

-continued
AK
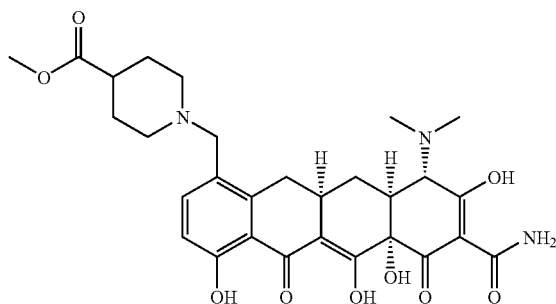
AL
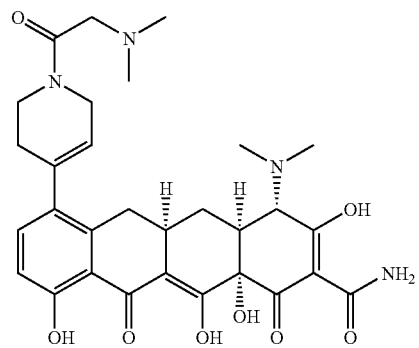
AM
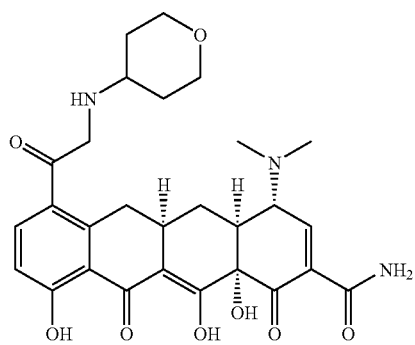
AO
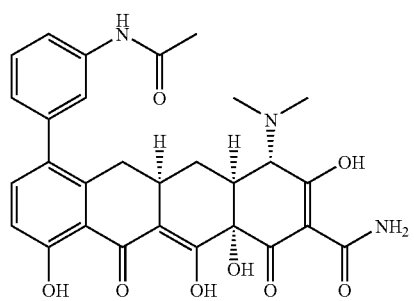
AP
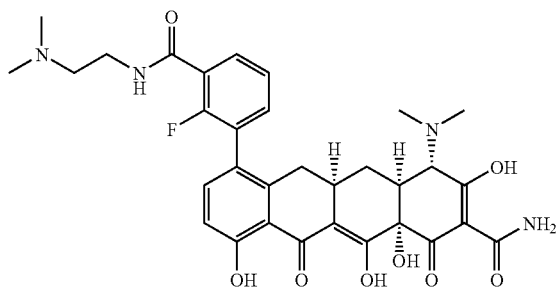
AQ
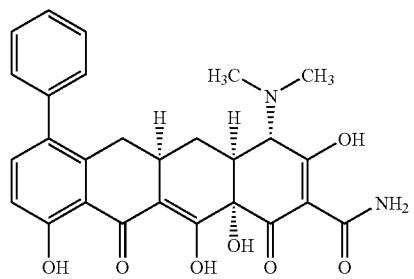
AR
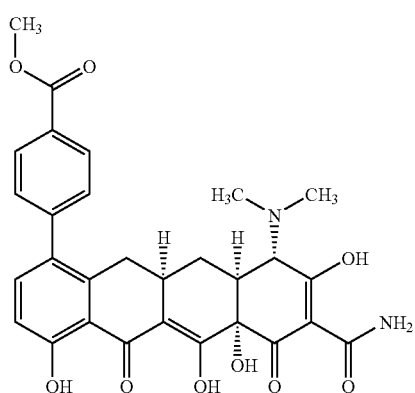
AS
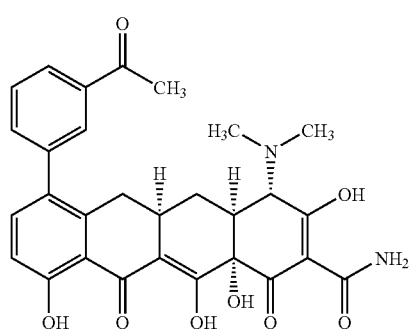

-continued
AT 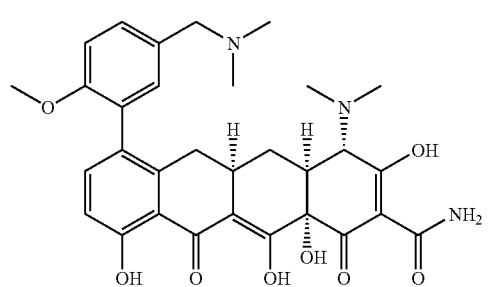
AU 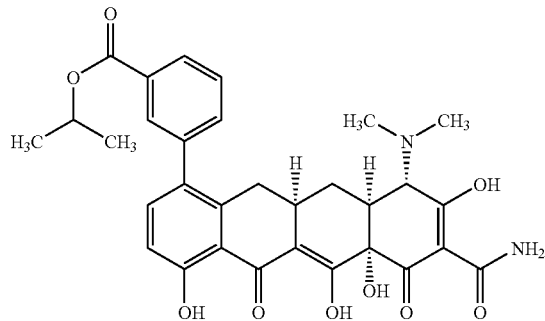
AV 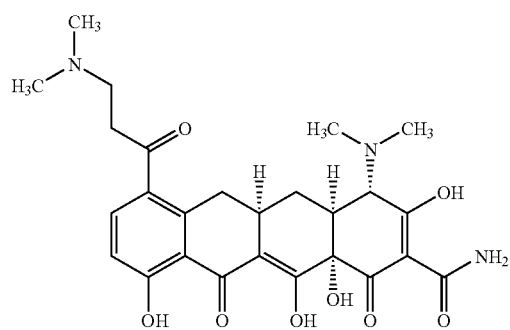
AW 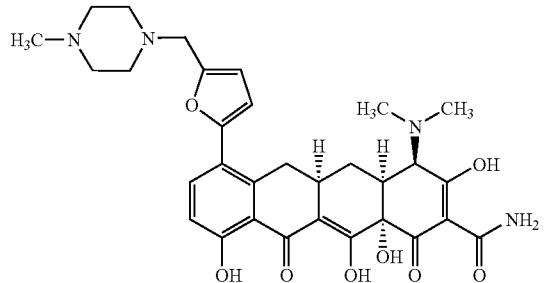
AX 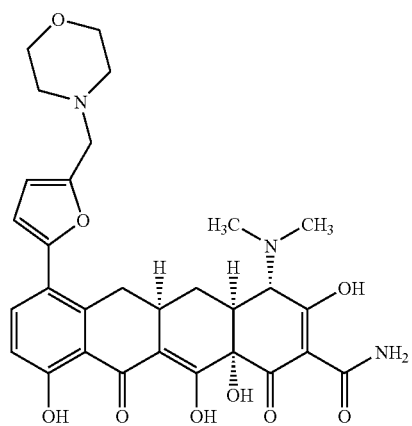
AY 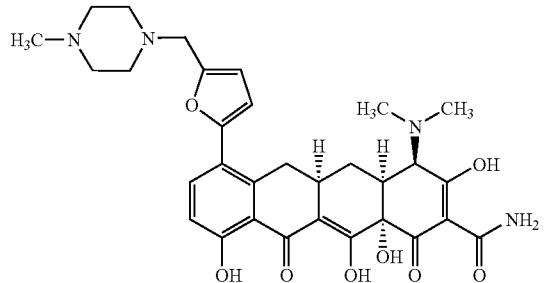
AZ 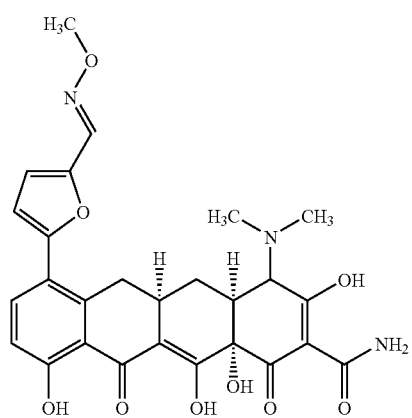

-continued
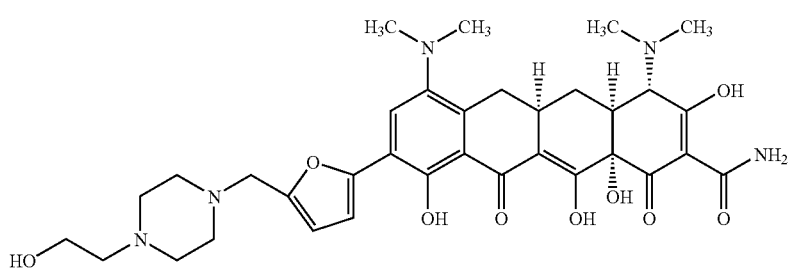
BA
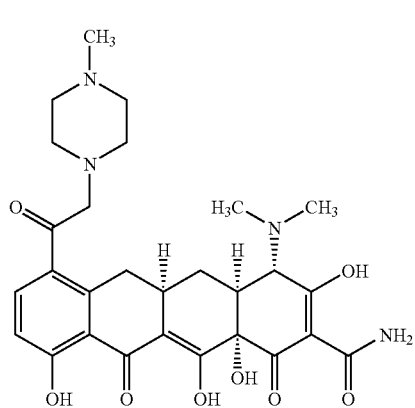
BB
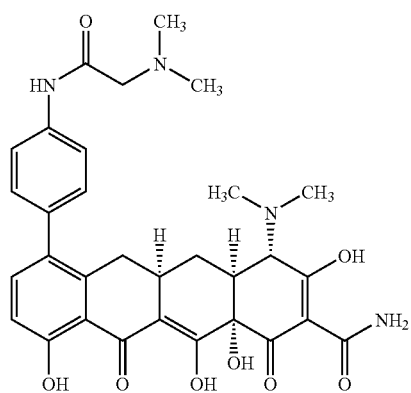
BC
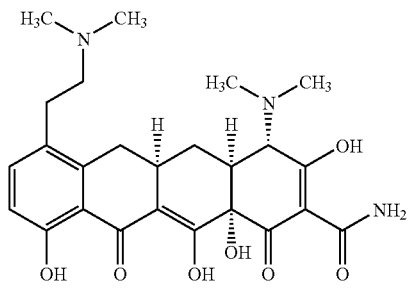
BD
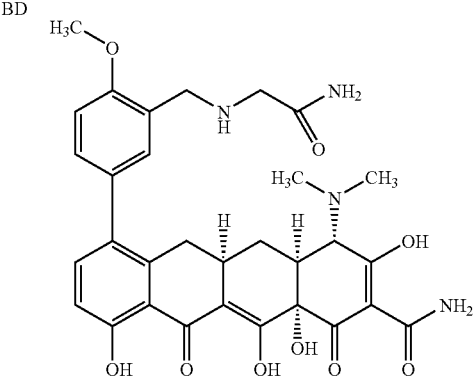
BE
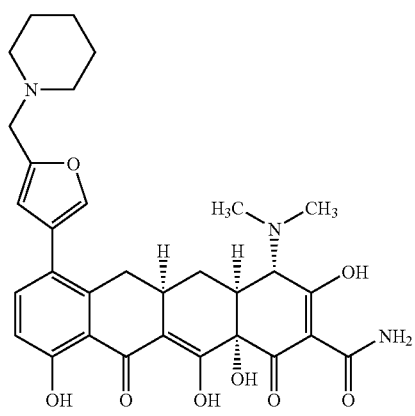
BF
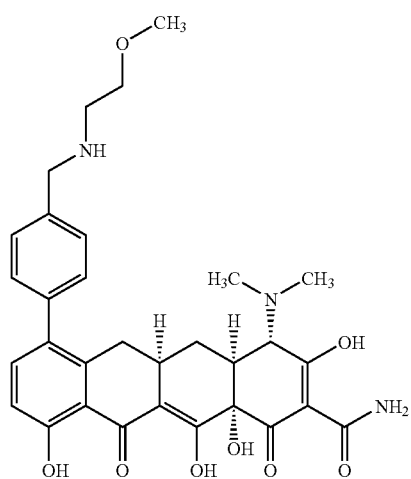
BG BH
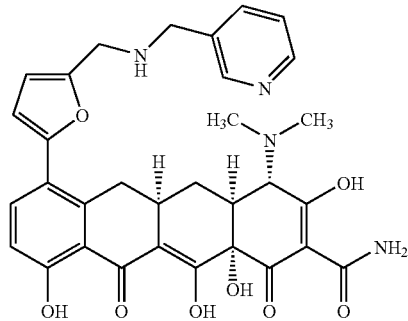
BI
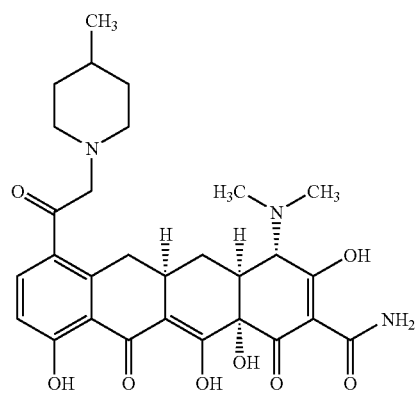
BJ
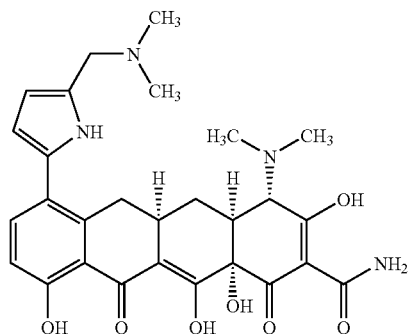
BK
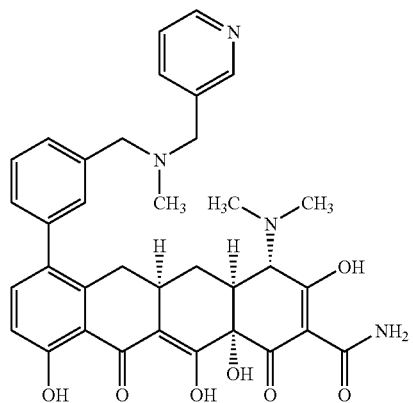
BL
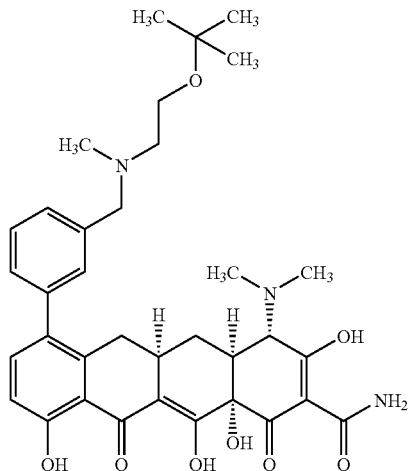
BM
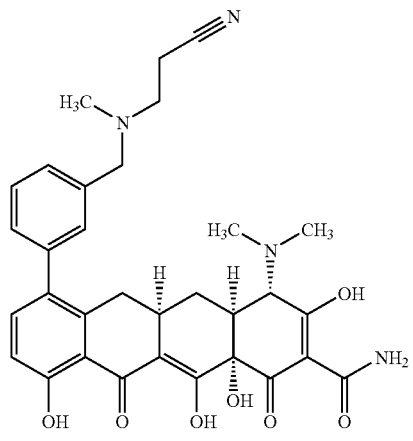

-continued
BN
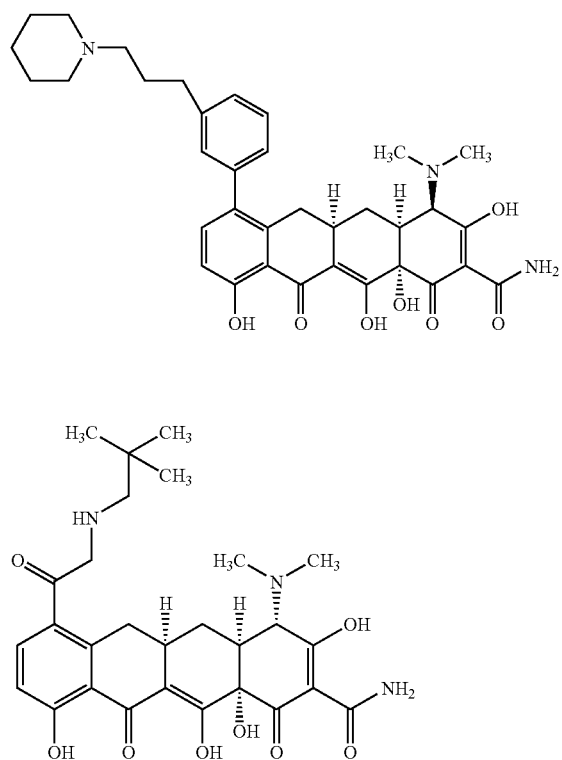
BO
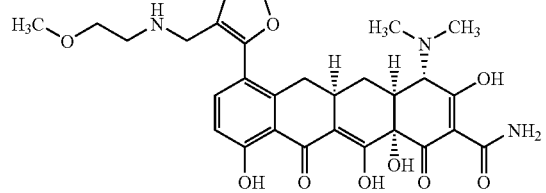
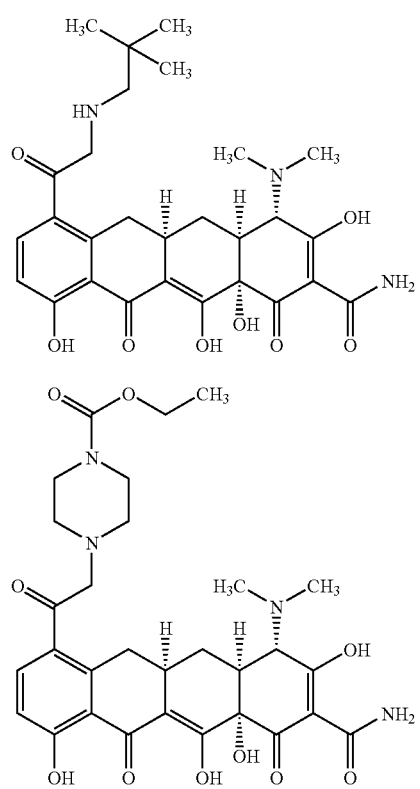
BP
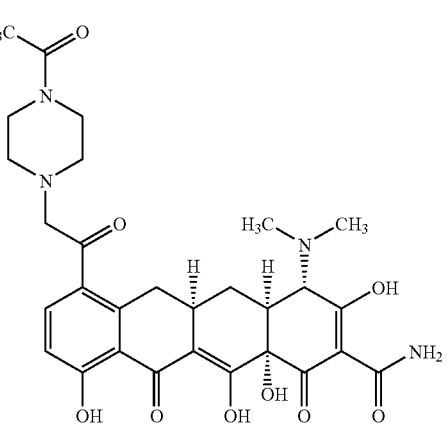
BQ
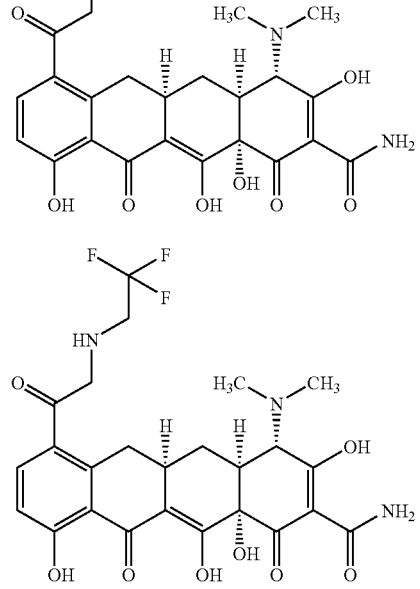
BR
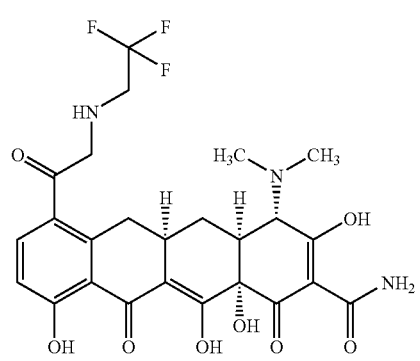
BS
BT
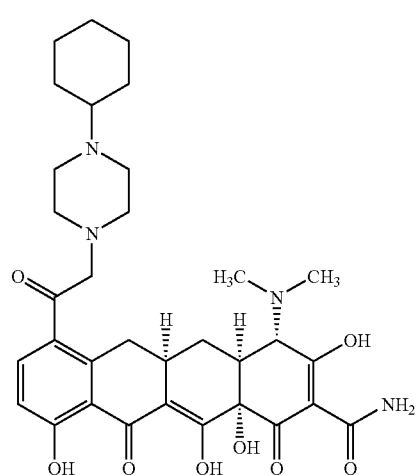
BU -continued
| | |
|---|---|
| BV 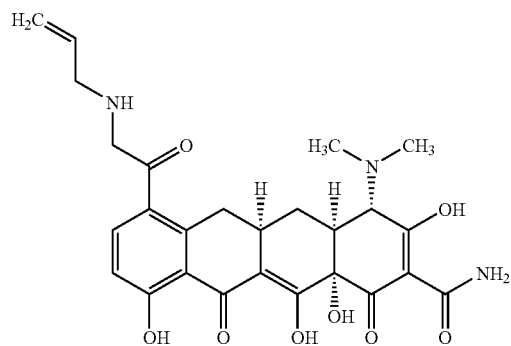 | BW 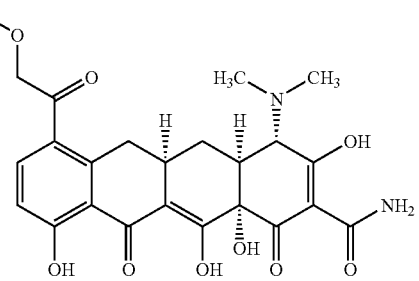 |
| BX 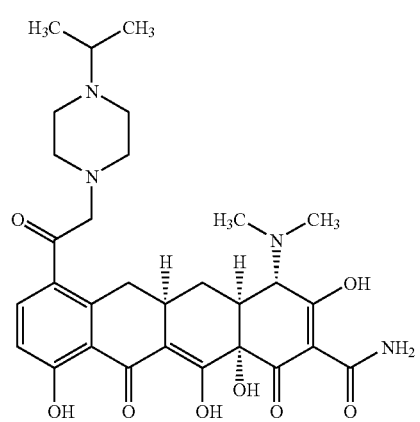 | BY 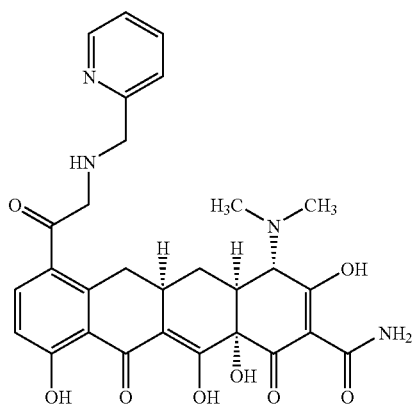 |
| BZ 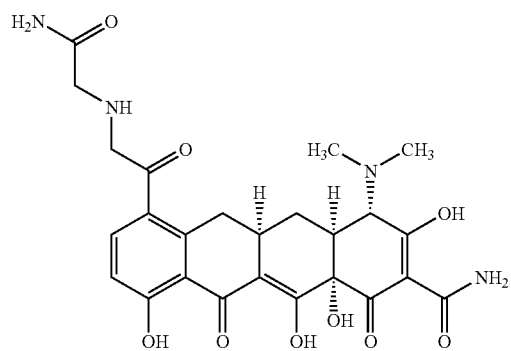 | CA 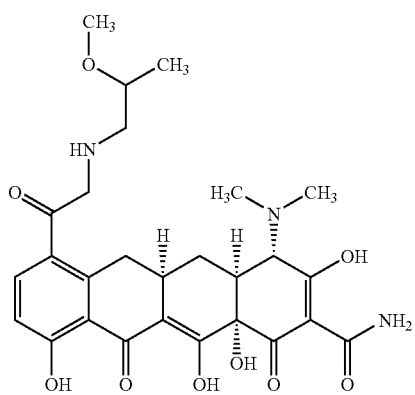 |
| CB 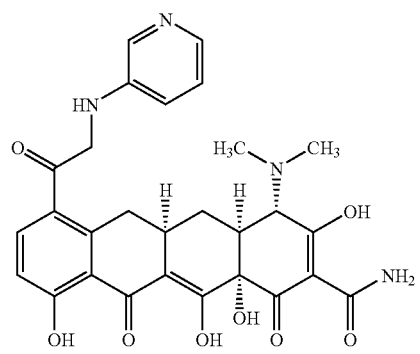 | CC 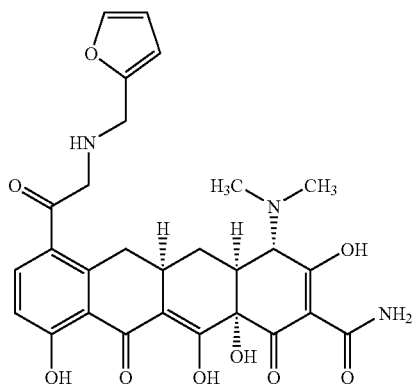 |

-continued
| | |
|---|---|
| CD 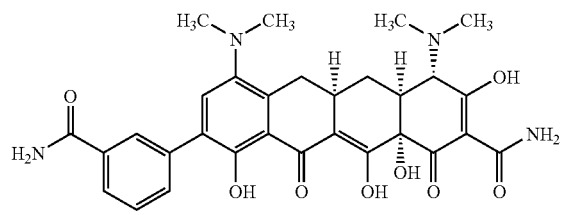 | CE 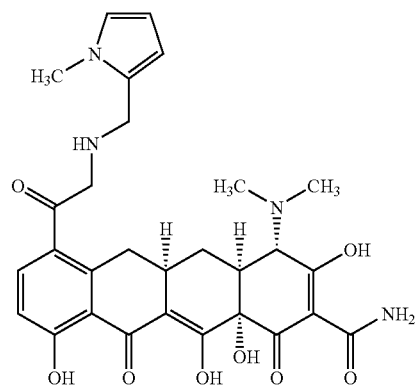 |
| CF 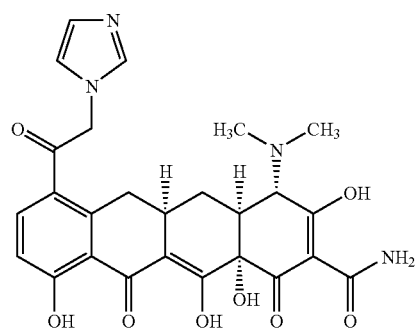 | CG 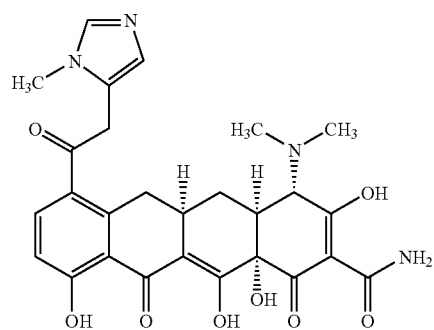 |
| 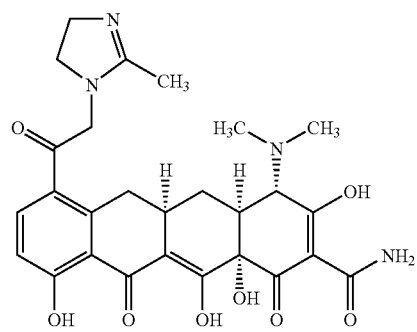 | CH 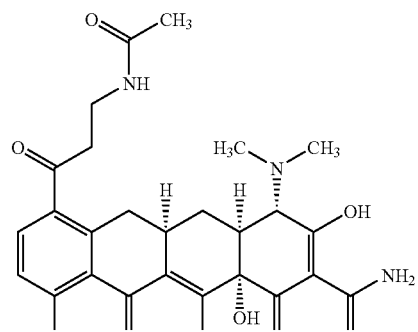 CI |
| CJ 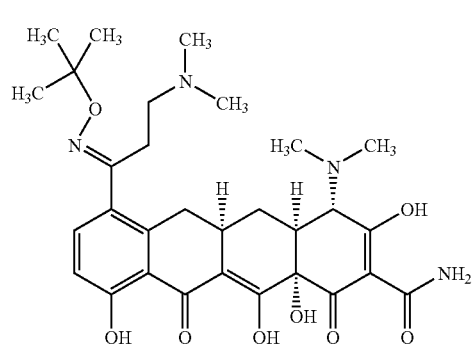 | CK 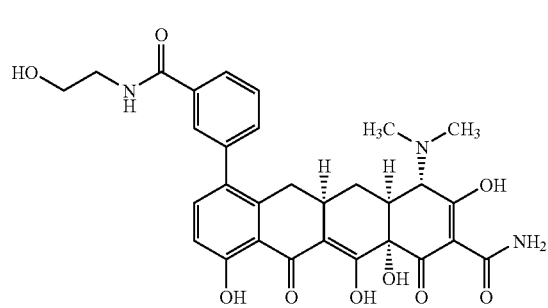 |

-continued
CL
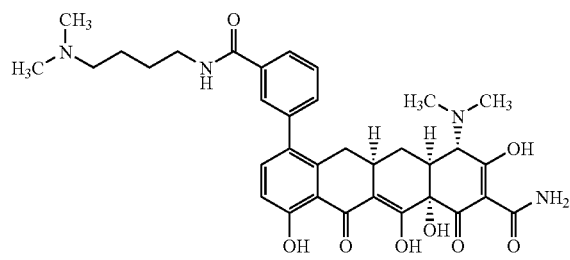
CM
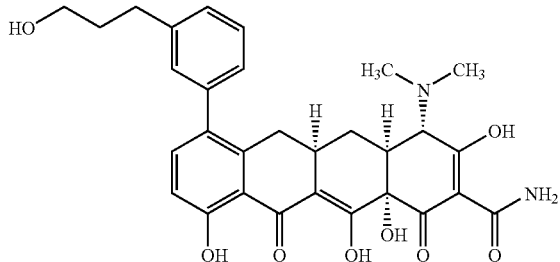
CN
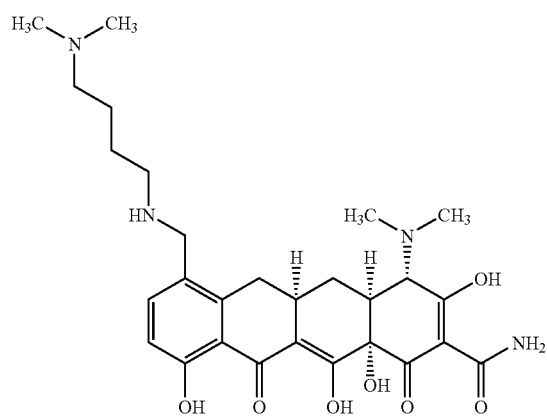
CO
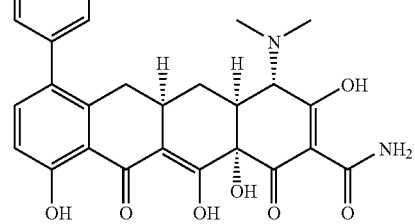
CP
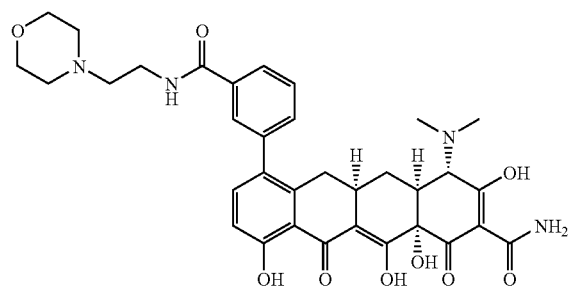
CQ
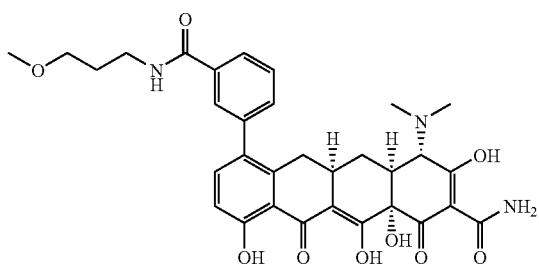
CR
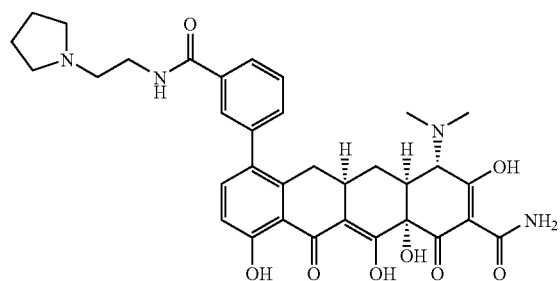
CS
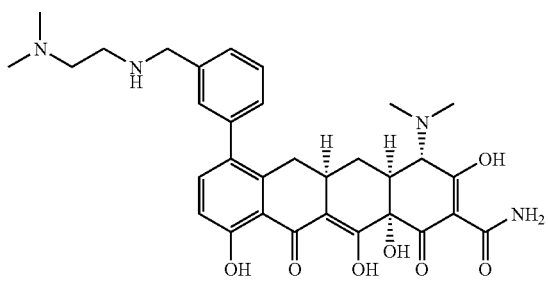
CT
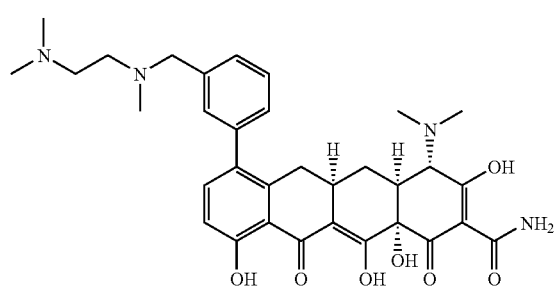
CU
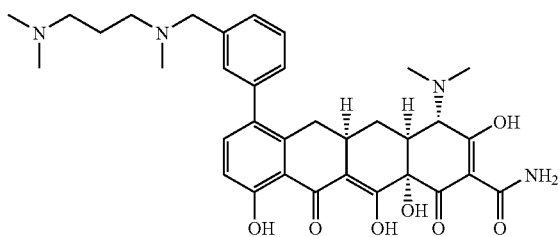

-continued

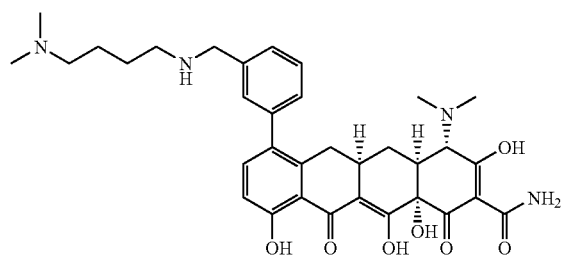
CV

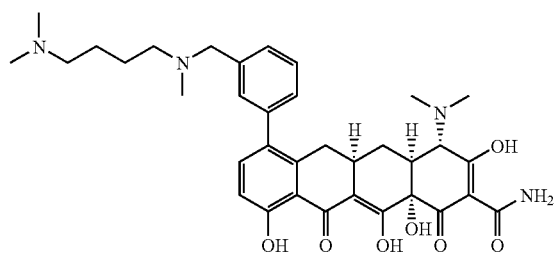
CW

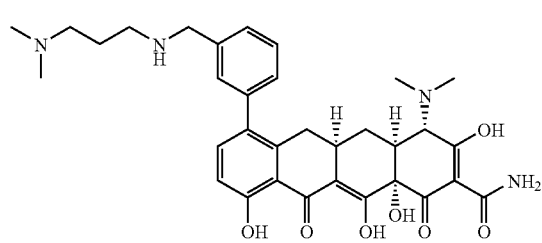
CX

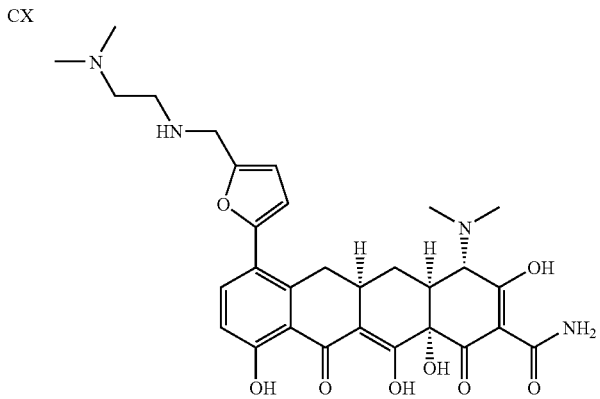
CY

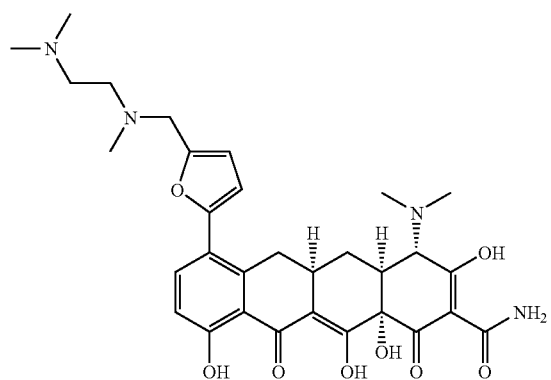
CZ

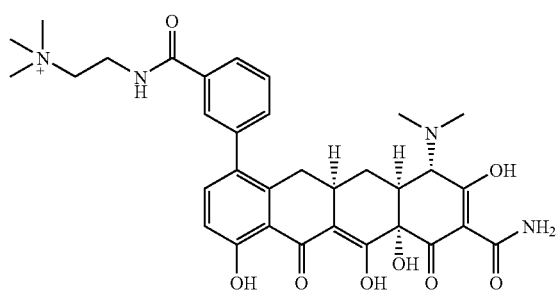
DA and pharmaceutically acceptable salts thereof.

Each of the tetracycline compounds described herein may be used in the methods and pharmaceutical compositions of the invention.

Methods for Synthesizing Tetracycline Compounds of the Invention.

The tetracycline compounds of the invention can be synthesized using the methods described in the following schemes and by using art recognized techniques. All novel tetracycline compounds described herein are included in the invention as compounds.

Scheme 1 outlines the general synthesis of 7-substituted tetracyclines. A 7-iodo sancycline derivative (1) may be reacted in a Stille coupling or a Suzuki coupling by reacting with an organotin derivative or a boronic acid derivative in the presence of a palladium catalyst to form the desired product (2).

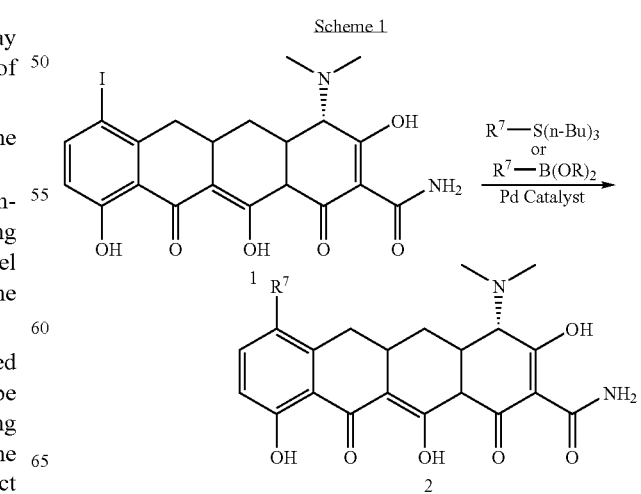
Scheme 1

Scheme 2 depicts a method for synthesizing aromatic substituted 9-substituted tetracycline compounds. A 9-iodo tetracycline derivative (3) is reacted under Suzuki conditions by mixing with a boronic acid in the presence of the appropriate palladium catalyst to give compounds similar to compound 4. Compounds V, X, BA and CD may be synthesized as illustrated as in Scheme 2.

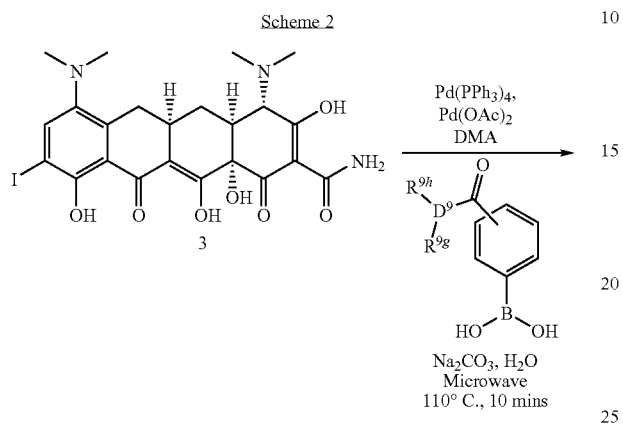

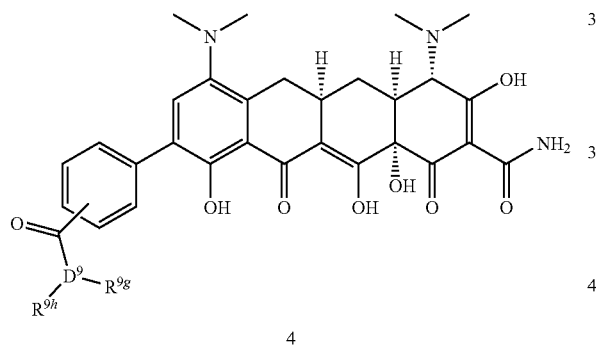

Scheme 3 depicts the synthesis of aminocarbonyl substituted aromatic 7-substituted-4-dedimethylamino tetracycline compounds. Starting from 7-iodo substituted-4-dedimethylamino sancycline (5), a Suzuki coupling reaction is performed with a boronic acid in the presence of a palladium catalyst to provide compound 6. Compound B, Z and AE may be synthesized in this manner.

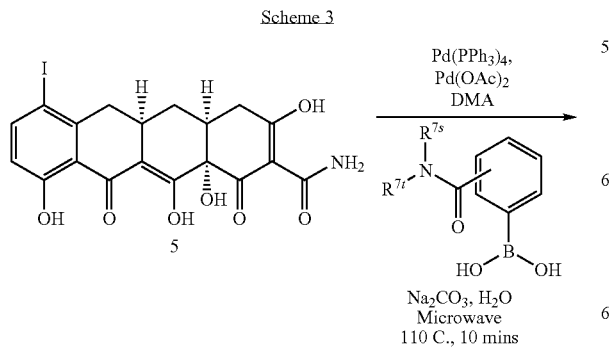

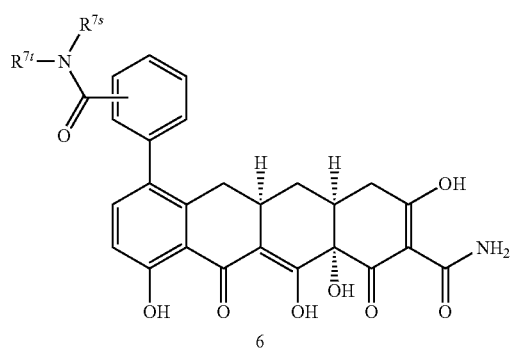

The 7-substituted acyl and oxime derivatives may also be prepared as shown in Scheme 4. An 7-iodo sancycline derivative (1) can be reacted with a substituted alkyne in the presence of palladium to synthesize the alkynyl derivative 7. Compound 7 may be converted to the acyl substituted compound 8 by any technique known in the art (e.g., by acid catalyzed hydrolysis). Compounds AV and CI may be prepared in this manner. The desired oxime product 9 can be obtained by reacting the acyl moiety with a primary hydroxylamine. Compound CJ may be synthesized as shown in Scheme 4.

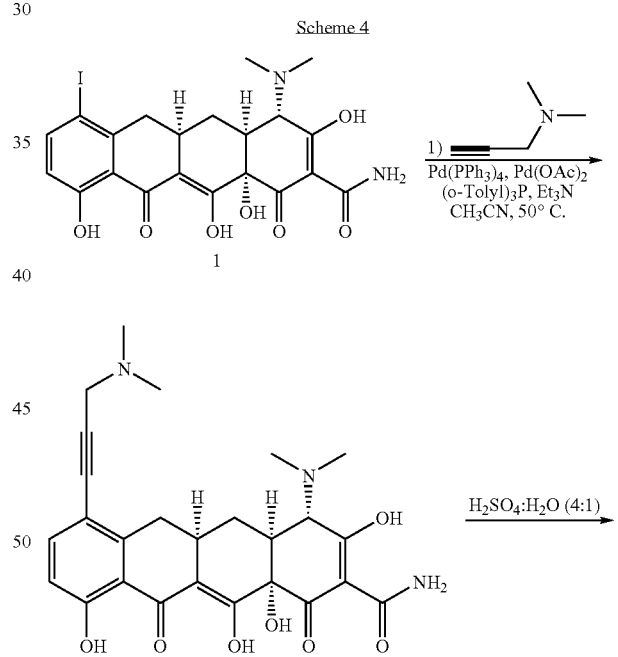

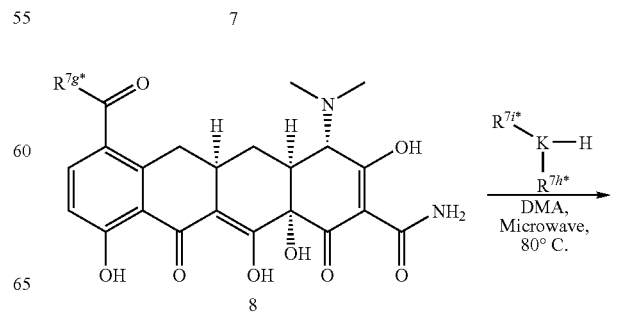

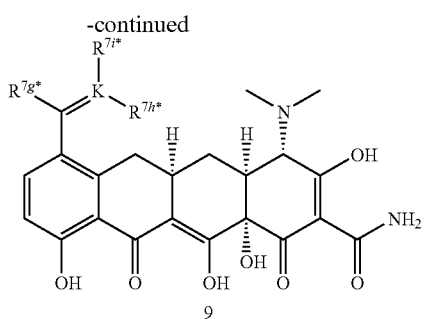

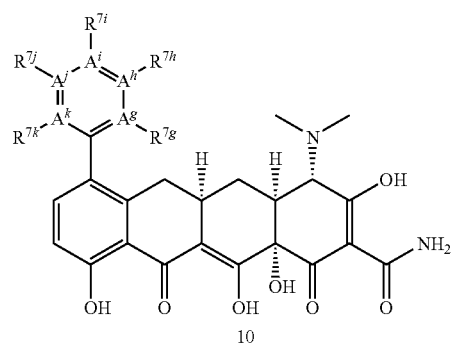

Scheme 5 depicts generally the synthesis of substituted aromatic 7-substituted tetracycline compounds. Beginning with 1 and performing a Suzuki coupling reaction in the presence of a boronic acid and a palladium catalyst, compounds of general formula 10 are formed. Compounds G, H, W, AQ, AR, AS, AT, AU, AW, BE, BG, BJ, BL, BM, BN, CM, BG and CO may be synthesized as shown in Scheme 5.

Scheme 6 also depicts the synthesis of substituted aromatic 7-substituted tetracycline compounds. Again, starting from 7-iodo substituted sancycline (1), a Suzuki coupling reaction is performed with a boronic acid in the presence of a palladium catalyst to provide intermediate 11 in which $R^{7i}$ or $R^{7j}$ are either an amine or a carboxylic acid. If the substituent is a carboxylic acidic moiety, a coupling to a secondary amine in the presence of base and a typical coupling reagent to form 7-substituted tetracyclines similar to 12a. Compounds A, C, D, E, F, I, J, L, M, N, O, P, R, S, T, U, Y, Z, AA, AB, AC, AD, AE, AP, CK, CL and DA may be synthesized as illustrated in this manner. Alternatively, if the substituent is an amino moiety, coupling of the amino moiety to an acid chloride or carboxylic acid in the presence of a base and a typical coupling reagent may be used to form 7-substituted tetracyclines similar to 12b. Compounds K, Q, AO, AF and BC may be synthesized in this manner.

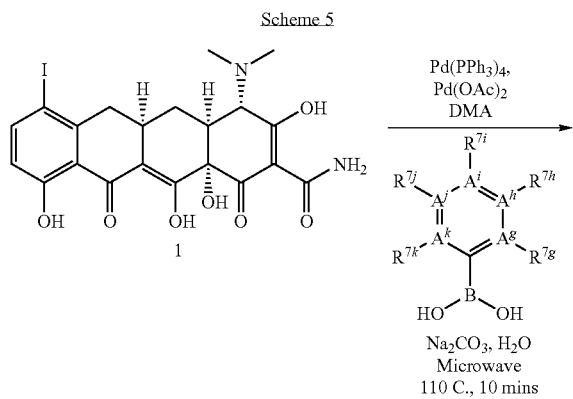

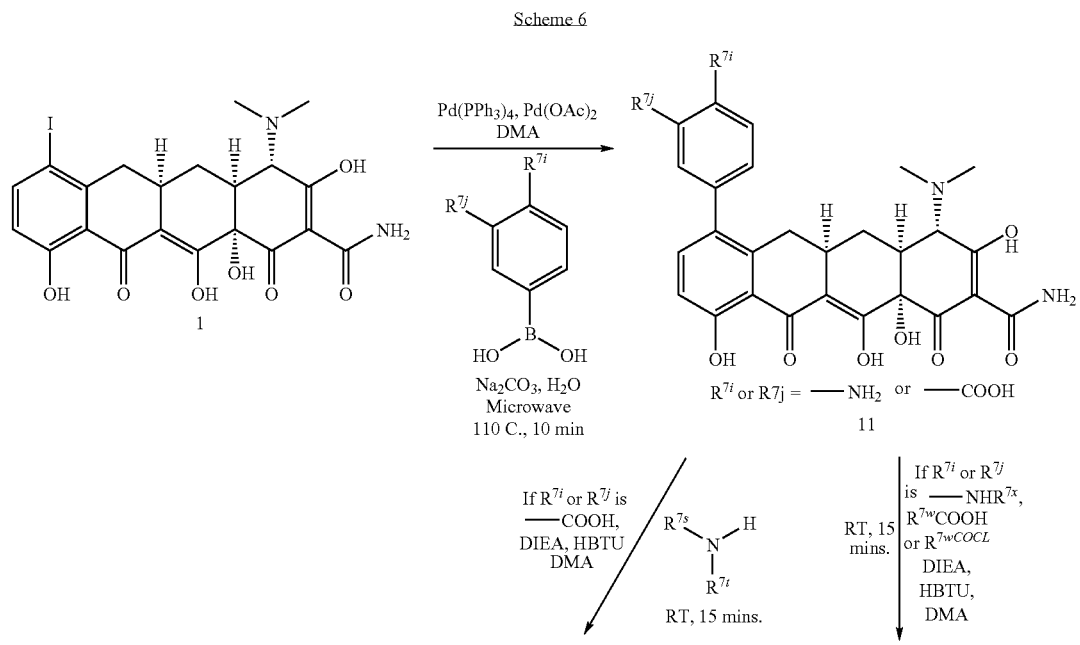

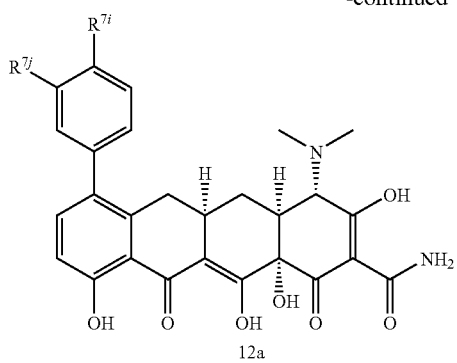

12a

R[7i] or R[7j] may be ——CON[7t]R[7s]

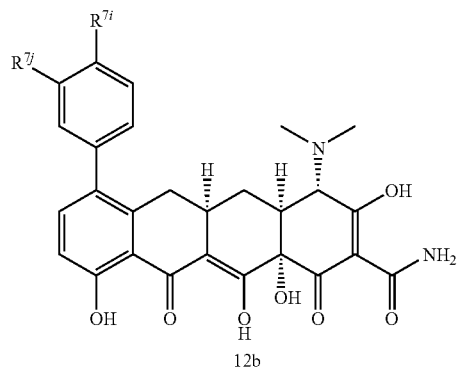

12b

R[7i] or R[7j] may be ——NR[7x]COR[7w]

Synthesis of substituted 7-acyl tetracycline compounds may be accomplished by the general procedure outlined in Scheme 7. Alpha bromination of compound 13 yields the intermediate 14 which can be reacted with an appropriate nucleophile to yield compounds of the formula 15. Compounds AG, AJ, AM, BB, BH, BO, BP, BR, BS, BT, BU, BV, BW, BX, BY, BZ, CA, CB, CC, CE, CF and CH may be synthesized in this manner.

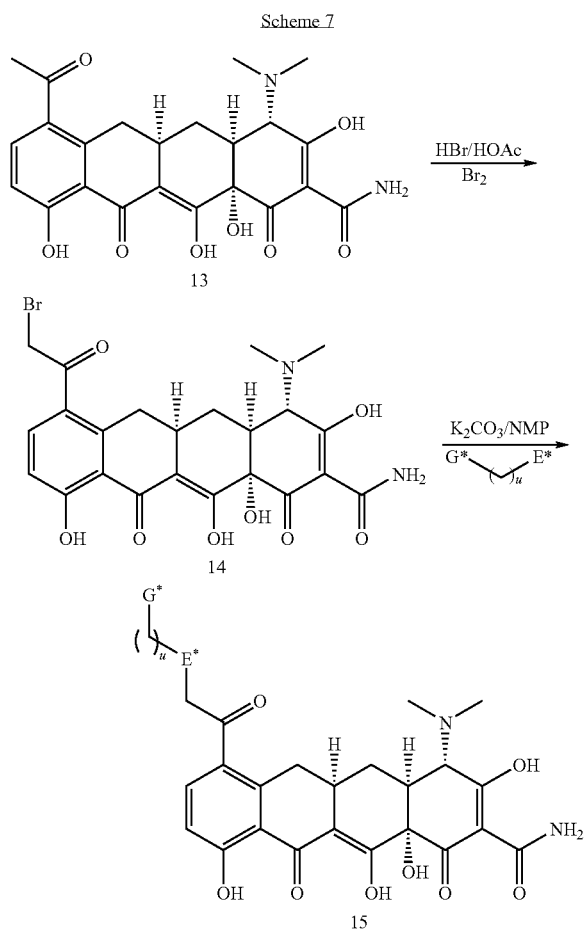

Scheme 7

Substituted 7-carboxamide derivatives of tetracyclines, such as compounds AH and AI, may be prepared using the general synthesis outlined in Scheme 8. Carbonylation of the 7-iodotetracycline compound 1 yields the 7-carboxy tetracycline intermediate 16. Standard coupling reactions with the desired amine yields compounds of the formula 17.

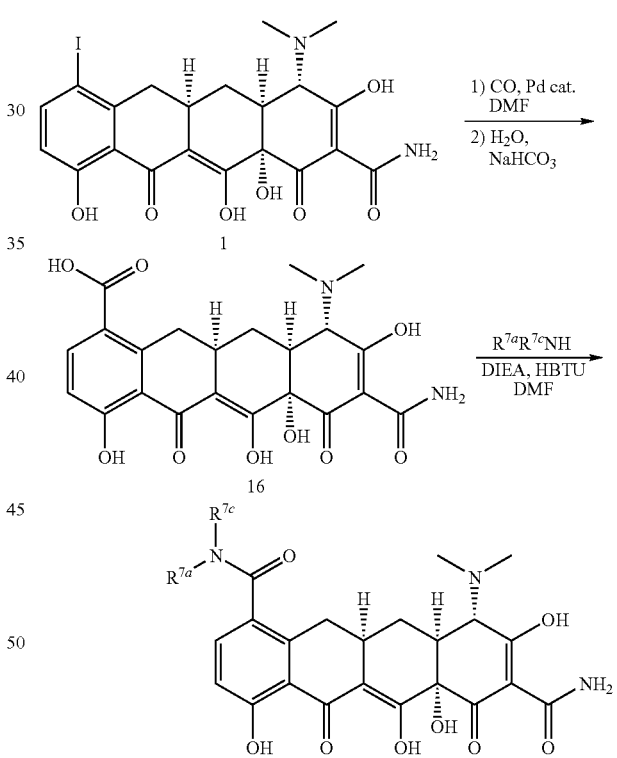

Scheme 8

Scheme 9 illustrates the synthesis of 7-heteroaryl-substituted tetracycline derivatives. Using the general procedure outlined in Scheme 1, compounds of formula 18 may be prepared by performing a Suzuki coupling with a 2-formyl-heteroaryl boronic acid. Subsequent reaction of compounds of formula 18 with an amine or alkoxyamine yields the imine or oxime 19. This is the procedure used to synthesis AZ. Compound 19 may then be reduced to produce compounds of formula 20. Compounds AX, AY, BF, BI, BK, BQ, CY and CZ may be synthesized in this manner.

Scheme 9

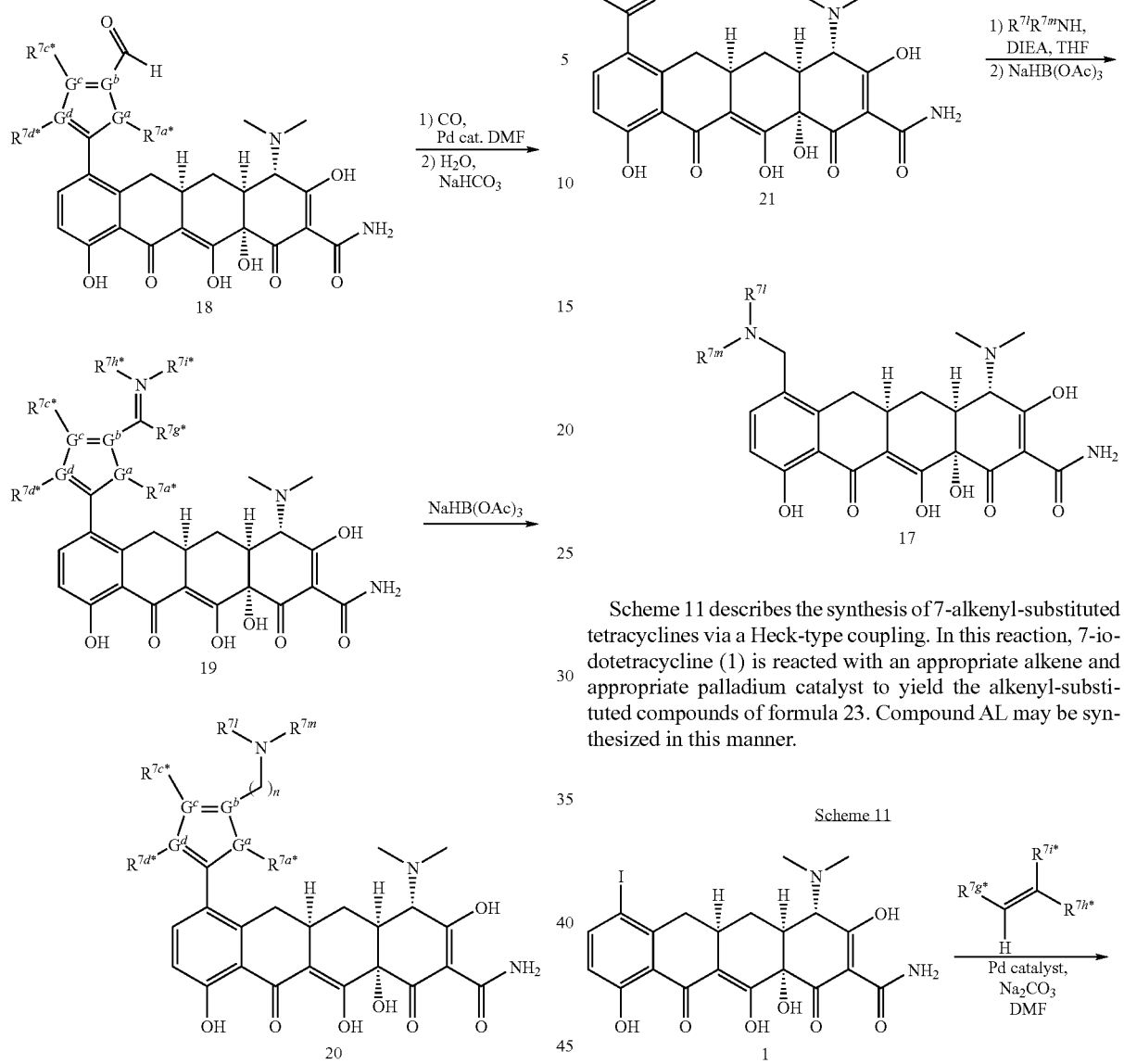

Scheme 10 describes the synthesis of 7-aminomethyl-substituted tetracyclines. Starting from compound I, a carbonyl insertion reaction may be performed to yield the 7-formyl tetracycline 21. A reductive alkylation of compound 21 with an appropriate amine yields compounds of formula 22. Compounds AK and CN may be synthesized in this manner.

Scheme 10

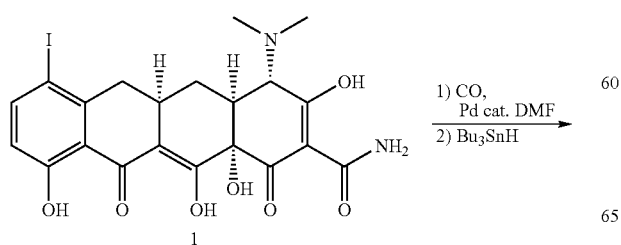

Scheme 11 describes the synthesis of 7-alkenyl-substituted tetracyclines via a Heck-type coupling. In this reaction, 7-iodotetracycline (1) is reacted with an appropriate alkene and appropriate palladium catalyst to yield the alkenyl-substituted compounds of formula 23. Compound AL may be synthesized in this manner.

Scheme 11

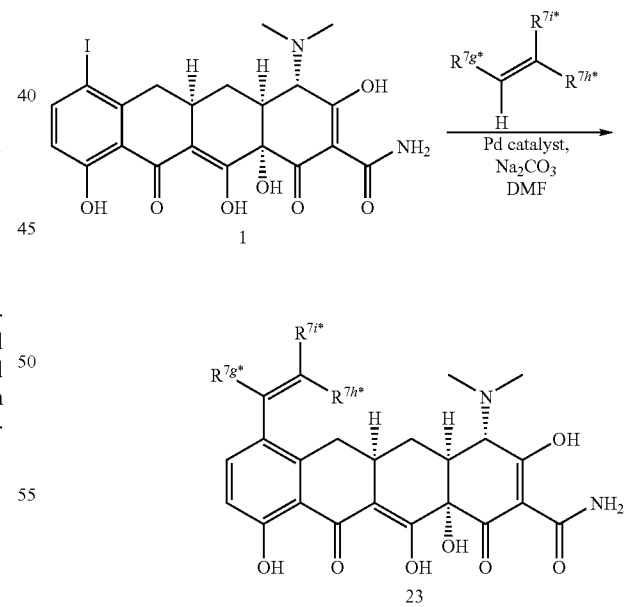

Scheme 12 depicts the synthesis of 7-(3-aminomethylphenyl)-tetracycline derivatives of formula 25. In this reaction, compound 24 (synthesized as described in Scheme 1), undergoes a reductive alkylation with an appropriate amine to yield compound 25. Compounds BJ, BL, BM, CS, CT, CU, CV, CW and CX may be synthesized in this manner.

Scheme 12

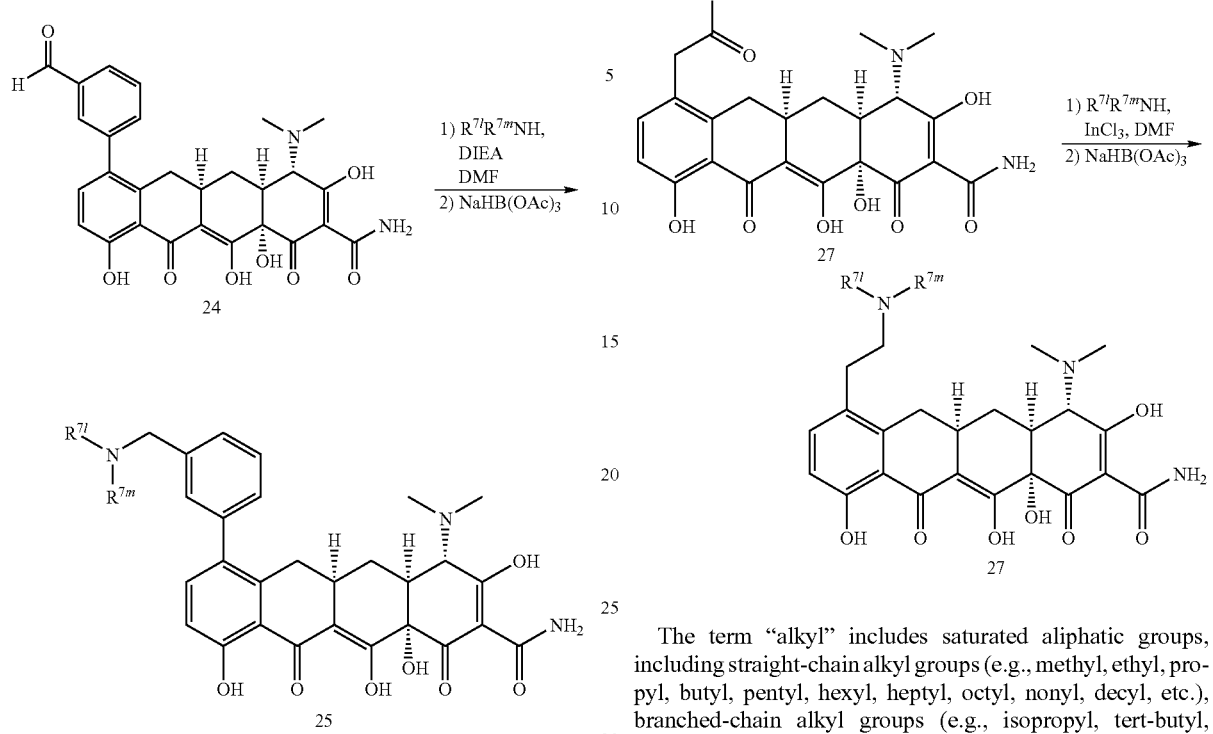

Scheme 13 describes the synthesis of 7-aminoethyl tetracycline derivatives similar to compound 28. 7-Iodotetracycline undergoes a Suzuki-type coupling with the appropriate boronic acid to yield compound 26, which is followed by an acid hydrolysis to yield aldehyde 27, which may further be modified by reductive alkylation to yield aminoethyl tetracyclines of formula 28. Compound BD may be synthesized in this manner.

Scheme 13

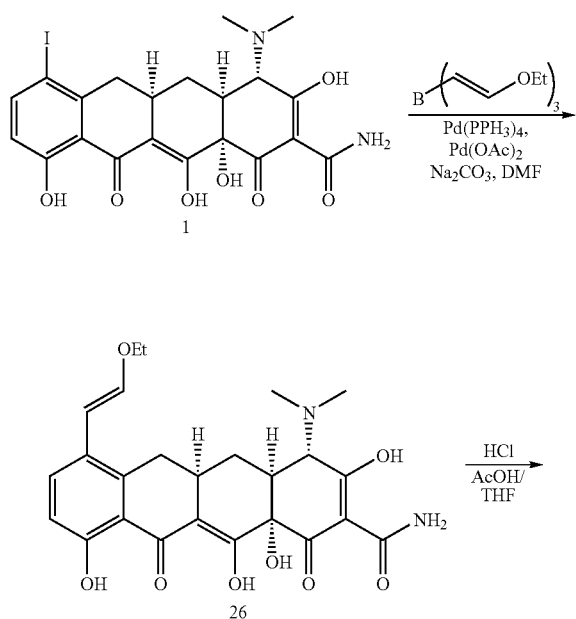

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (e.g., isopropyl, tert-butyl, isobutyl, etc.), cycloalkyl (alicyclic) groups (e.g., cyclopropyl, cyclobutyl, cyclopentyl, cyclohexyl, cycloheptyl, cyclooctyl), alkyl substituted cycloalkyl groups, and cycloalkyl substituted alkyl groups. The term alkyl further includes alkyl groups that include oxygen, nitrogen, sulfur or phosphorous atoms replacing one or more carbons of the hydrocarbon backbone. In certain embodiments, a straight chain or branched chain alkyl has 20 or fewer carbon atoms in its backbone (e.g., $C_1$-$C_{20}$ for straight chain, $C_3$-$C_{20}$ for branched chain), and more preferably 4 or fewer. Cycloalkyls may have from 3-8 carbon atoms in their ring structure, and more preferably have 5 or 6 carbons in the ring structure. The term $C_1$-$C_6$ includes alkyl groups containing 1 to 6 carbon atoms.

The term "heterocyclic" includes cycloalkyl moieties in which one or more carbons of the cycloalkyl scaffold is replace with a heteroatom, for example, oxygen, nitrogen, sulfur or phosphorous. Examples of heterocyclic moieties include piperidine, morpholine, pyrrolidine, piperazine and tetrahydrofuran.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, tetrahydropyridine, quinoline, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 20 or fewer carbon atoms in its backbone (e.g., $C_2$-$C_{20}$ for straight chain, $C_3$-$C_{20}$ for branched chain). Likewise, cycloalkenyl groups may have from 3-8 carbon atoms in their ring structure, and more preferably have 5 or 6 carbons in the ring structure. The term $C_2$-$C_{20}$ includes alkenyl groups containing 2 to 20 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 20 or fewer carbon atoms in its backbone (e.g., $C_2$-$C_{20}$ for straight chain, $C_3$-$C_{20}$ for branched chain). The term $C_2$-$C_6$ includes alkynyl groups containing 2 to 6 carbon atoms.

Moreover, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including, e.g., alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—). The term "substituted acyl" includes acyl groups where one or more of the hydrogen atoms are replaced by for example, alkyl groups, alkenyl, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "carbonylamino" includes moieties wherein a carbonyl moiety (e.g., —C(=O)) is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "amide" or "aminocarbonyl" includes compounds or moieties which contain a nitrogen atom which is bound to the carbon of a carbonyl or a thiocarbonyl group. The term includes "arylaminocarbonyl" groups which include aryl or heteroaryl moieties bound to an amino group which is bound to the carbon of a carbonyl or thiocarbonyl group. The term also includes "alkylaminocarboxy," "alkenylaminocarboxy," "alkynylaminocarboxy," and in which alkyl, alkenyl and alkynyl moieties, respectively, are bound to a nitrogen atom which is in turn bound to the carbon of a carbonyl group.

The term "amine" or "amino" includes compounds where a nitrogen atom is covalently bonded to at least one carbon or heteroatom. The term includes "alkylamino" moieties, wherein the nitrogen is bound to at least one additional alkyl group. The term also includes "dialkylamino" groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "aroyl" includes compounds and moieties with an aryl or heteroaromatic moiety bound to a carbonyl group. Examples of aroyl groups include phenylcarboxy, naphthyl carboxy, etc.

The term "carbonyl" or "carboxy" includes compounds and moieties which contain a carbon connected with a double bond to an oxygen atom and the carbon atom is bonded to two additional moieties. Examples of moieties which contain a carbonyl include aldehydes, ketones, carboxylic acids, amides, esters, anhydrides, etc. Suitable moieties bonded to the carbon of a carbonyl group include, for example, hydrogen, alkyl groups, alkenyl, alkynyl groups, halogens, hydroxyl, alkylcarb onyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "carbonyloxy" includes moieties in which the carbon of a carbonyl group is covalently bound to an oxygen.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "halogen" includes fluorine, bromine, chlorine, iodine, etc. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻X⁺, where X⁺ is a counterion.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "thiocarbonyl" or "thiocarboxy" includes compounds and moieties which contain a carbon connected with a double bond to a sulfur atom.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "sulfonyl" includes moieties which comprise a sulfonyl group. Similarly, the term "sulfinyl" includes moieties which comprise a sulfinyl group.

The term "oximyl" includes moieties which comprise an oxime group.

The term "dimeric moiety" includes moieties which comprise a second tetracycline four ring structure. The dimeric moiety may be attached to the substituted tetracycline through a chain of from 1-30 atoms. The chain may be comprised of atoms covalently linked together through single, double and triple bonds. The tetracycline ring structure of the dimeric moiety may further be substituted or unsubstituted. It may be attached at the 1, 2, 3, 4, 5, 6, 7, 8, 9, 10, 11, 11a, 12, 12a, and/or 13 position.

The term "prodrug moiety" includes moieties which can be metabolized in vivo. Generally, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The structures of some of the substituted tetracycline compounds used in the methods and compositions of the invention include asymmetric carbon atoms. The isomers arising from the chiral atoms (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The method may further comprise administering the tetracycline compound in combination with a second agent, e.g., an agent which may enhance treatment of the spinal muscular atrophy.

The language "in combination with" a second agent includes co-administration of the tetracycline compound, and with the second agent, administration of the tetracycline compound first, followed by the second agent and administration of the second agent first, followed by the tetracycline compound. The second agent may be any agent which is known in the art to treat, prevent, or reduce the symptoms of a spinal muscular atrophy. Furthermore, the second agent may be any agent of benefit to the patient when administered in combination with the administration of an tetracycline compound. Examples of second agents include neuroprotective agents.

Pharmaceutical Compositions for the Treatment of Spinal Muscular Atrophy

The invention also pertains at least in part to pharmaceutical compositions for the treatment of spinal muscular atrophy. The pharmaceutical compositions comprise a tetracycline compound of the invention in combination with a pharmaceutical acceptable carrier. The composition may further comprise a second agent for the treatment of spinal muscular atrophy or its symptoms. Each of the tetracycline compounds described herein may be used in pharmaceutical compositions of the invention.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, spinal, buccal, sublingual, rectal, vaginal, pulmonary and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Sprays also can be delivered by mechanical, electrical, or by other methods known in the art.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial, antiparasitic and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle. The compositions also may be formulated such that its elimination is retarded by methods known in the art.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration or administration via inhalation is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, administration via spinal tap, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. Other methods for administration include via inhalation.

The tetracycline compounds of the invention may also be administered to a subject via stents. The compounds may be administered through the stent or be impregnated in the stent itself.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats spinal muscular atrophy.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Farm. SCI.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The invention also pertains, at least in part, to packaged compositions comprising the tetracycline compounds of the invention and instructions for using said compounds for the treatment of spinal muscular atrophy.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

Example 1

In Vitro Cell-Free Assay for Detection of Inclusion of Exon 7 in SMA2 mRNA

The following example illustrates how tetracycline compound of the invention are active in an in vitro cell-free assay for the inclusion of exon 7 in SMA2 mRNA. SMN1 and SMN2 pre-mRNA were prepared by in vitro transcription using T7 RNA polymerase of minigene templates that include exon 6, a truncated portion of intron 6, exon 7, intron 7 and a portion of exon 8 in the presence of $^{32}$P-UTP. Labeled RNA was purified on a denaturing polyacrylamide gel followed by phenol extraction and ethanol precipitation of the RNA.

In vitro cell-free splicing of SMN1 and SMN2 transcripts was carried out in a 10 µl reaction volume at 30° C. for 3 hours. The reactions contained 10 fmol of labeled pre-mRNA, 30% (3 VI) HeLa cell nuclear extract (in 20 mM HEPES, pH 7.4, 20% (v/v) glycerol, 0.1M KC1, 0.2 mM EDTA), 1.3% (w/v) polyvinyl alcohol, 1.56 mM MgCl$_2$, 32 mM HEPES, pH 7.4, 0.5 mM ATP, 20 mM creatine phosphate and either 2 µl of test compound (in 20 mM HEPES, pH 7.4, 0.1M KC1, 0.2 mM EDTA) or buffer alone. Following incubation, 200 µl of a solution containing 0.3M NaAc and 0.2% SDS was added to the reaction. Proteins were removed by extraction with an equal volume of phenol and RNA was precipitated with 2.5 volumes of ethanol. RNA was resuspended in formamide sample buffer and separated on a 9% urea-denaturing polyacrylamide gel. Quantitation of splicing was based on phosphorimage analysis (Fujix BAS2000 or Fujifilm FLA-5100). In this assay, percentage exon 7 inclusion averages 12% for the unmutated SMN1 mRNA and 4% for the SMN2 mRNA.

Figure 2:
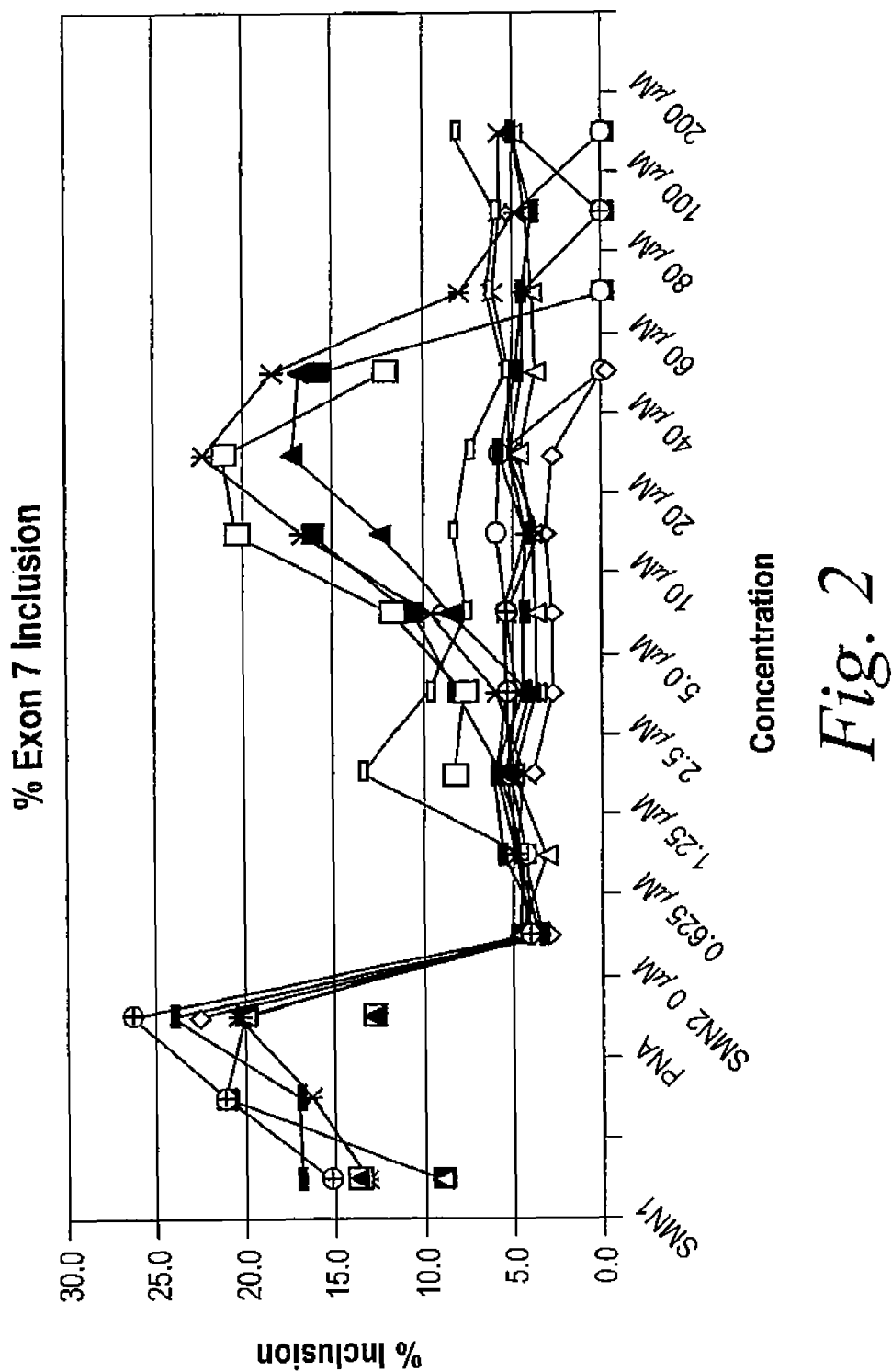
FIG. 2 is a chart illustrating the in vitro assay results for various tetracycline compounds expressed in percent inclusion of exon 7 in SMN2 mRNA.

The results of this assay are seen in FIG. 1, which shows the in vitro cell-free splicing assay results for compound J, expressed in % inclusion of exon 7 in the SMN2 mRNA, and in FIG. 2, which shows the in vitro assay cell-free results for compounds A, C, D, O, AD, AO and AE compared to tetracycline, minocycline and oxytetracycline.

Table 2 shows a summary of the in vitro cell-free splicing assay results for a number of tetracycline compounds. The in vitro activities for exon 7 splicing are expressed as the $E_{max}$ (the maximum percentage exon 7 inclusion observed) and $C_{max}$ (the lowest compound concentration at which the maximum inclusion occurs in µM). For $E_{max}$, percentage inclusion values of less than 10% are indicated by "*", values of 10-20% are indicated by "", and values greater than 20% are indicated by "*". For $C_{max}$ data, concentrations of greater than 40 µM are indicated by "*", concentrations between 40 and 10 µM are represented by "" and concentrations of less than 10 µM are represented by "*".

TABLE 2

| Compound | $C_{max}$ (µM) | $E_{max}$ (%) |
|---|---|---|
| A | ** | ** |
| E | ** | *** |
| I | * | *** |
| J | *** | ** |
| K | * | * |
| L | * | ** |
| M | ** | *** |
| N | ** | ** |
| O | ** | * |
| P | ** | ** |

TABLE 2-continued

| Compound | $C_{max}$ (μM) | $E_{max}$ (%) |
|---|---|---|
| Q | *** | ** |
| S | * | ** |
| T | ** | ** |
| U | ** | ** |
| Y | * | ** |
| AB | ** | *** |
| AF | *** | * |
| AG | ** | * |
| AH | ** | * |
| AI | * | ** |
| AK | ** | * |
| AM | *** | * |
| AW | *** | ** |
| AX | *** | ** |
| AY | *** | *** |
| AZ | *** | ** |
| BE | *** | ** |
| BF | *** | ** |
| BI | *** | ** |
| BJ | *** | ** |
| BL | * | ** |
| BN | *** | *** |
| BQ | *** | ** |
| BS | * | ** |
| BX | * | * |
| CB | ** | ** |
| CC | *** | ** |
| CE | *** | ** |
| CG | * | ** |
| CI | * | ** |
| CK | ** | ** |
| CL | ** | *** |
| CM | *** | ** |
| CN | *** | ** |
| CO | ** | ** |
| CP | ** | *** |
| CQ | * | ** |
| CR | ** | *** |
| CS | *** | ** |
| CT | ** | ** |
| CU | *** | ** |
| CV | *** | ** |
| CW | *** | ** |
| CX | *** | ** |

Example 2

In Vitro Gems Assay

The following example illustrates how tetracycline compound of the invention increase gems in vitro. A glass cover slide was added into each well of 6 well plates and 1×10⁴ cells (3813 SMA patient-derived fibroblast cells or 3814 unaffected family member-derived fibroblast cells) in 2 mL were added. After approximately 6 hours, the medium was changed and the desired compound was added to the appropriate well at indicated concentrations. After 12 hours, the medium was changed and the desired compound was added to the appropriate well again. After 24 hours, one set of slides was fixed and the medium was changed and the desired compound was added to the appropriate well again. After 36 hours, the medium was changed and the desired compound was added to the appropriate well again. Another set of cells were fixed on the slides at 48 hours.

Immunofluorescence staining of the cells was performed by washing the cells 2 times with PBS (phosphate buffered saline) and fixing the cells on slides in 4% paraformaldehyde for 10 minutes on ice. The cells were washed 3 times for 5 minutes with PBS, then were permeabilized on the cover slip with 0.2% TritonX, 0.5% BSA in PBS and incubated for 5 minutes on ice. The cells were subsequently blocked with blocking solution (2% bovine serum albumin, 2% normal goat serum in PBS, 3 times 10 minute incubations) at room temperature. The blocked cells were incubated for 1 hour at room temperature with either anti-SMN antibody (BD Transduction Labs) diluted 1:500 in blocking solution or anti-SMN antibody (2B1-Sigma) diluted 1:1000 in blocking solution. The cells were washed 2 times for 5 minutes each with PBS and were subsequently incubated with Alexa 594 secondary antibody (1:2000 dilution) for 1 hour at room temperature. The cells were again washed 2 times for five minutes with PBS, mounted on slides with Molecular Probes Prolong Antifade kit, dried and analyzed with Axioskop widefield fluourescence microscope.

Figure 3:
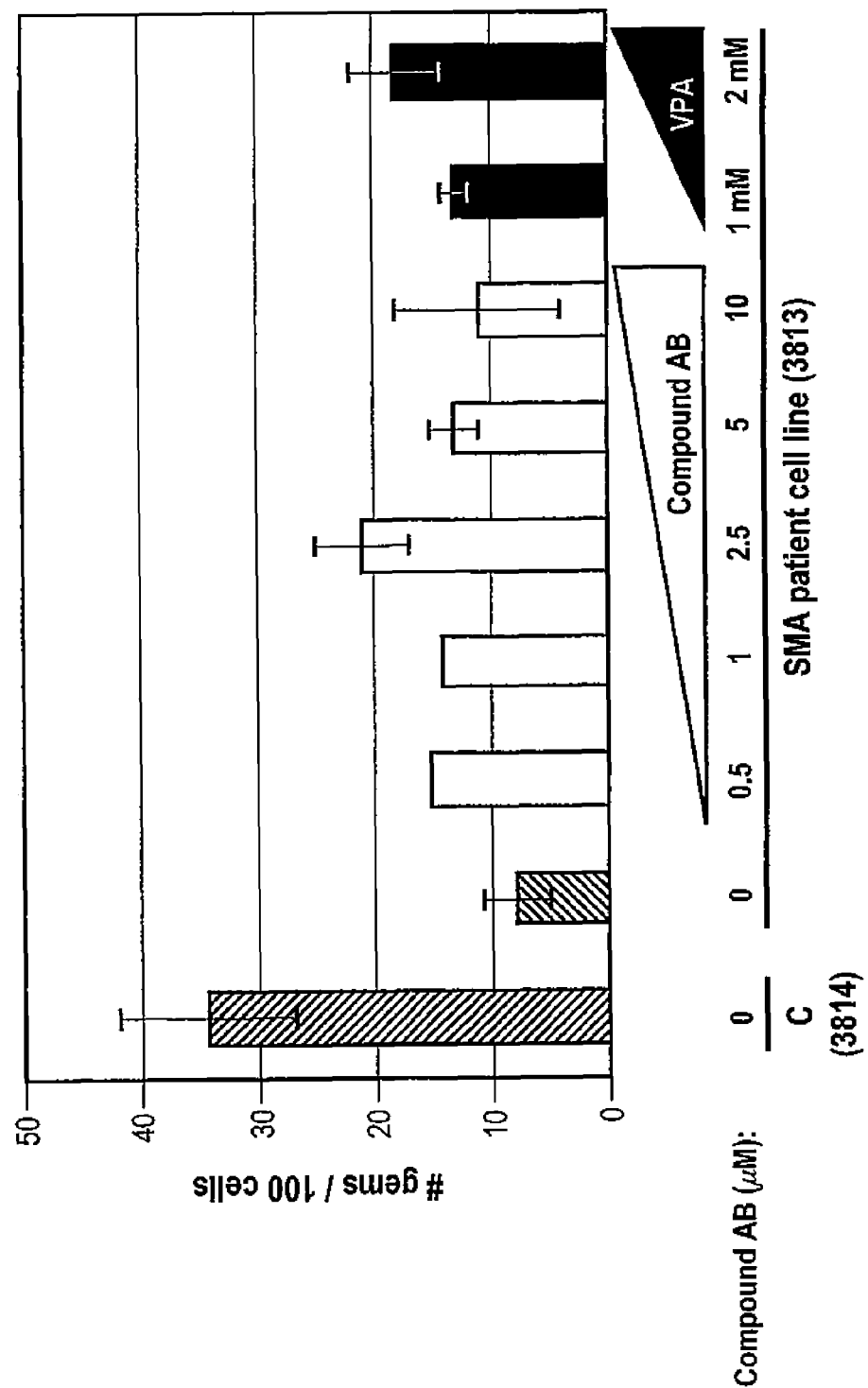
FIG. 3 is a graph illustrating the percent SMN protein levels relative to $\alpha$-tubulin in the cells of a patient with SMA as a function of the concentration of compound AB added in vitro.

In the gems assay, compound AB increased the number of gems in 3813 SMA fibroblast cells at the concentrations tested. FIG. 3 illustrates the increase in the number of gems/100 cells in the SMA patient line treated with compound AB (2.7-fold at 2.5 μM) as compared to valproic acid (1.7-fold at 1 mM), which has been previously shown to increase the SMN protein levels in SMA cell lines.

Example 3

In Vitro Protein Expression Assay

The following example illustrates how tetracycline compound of the invention increases the expression of pfSMN protein in 3813 fibroblasts. Human SMA type I patient fibroblasts 3813 and SMA carrier fibroblasts 3814 were seeded onto 24-well microtiter plates. The tetracycline compound was added to the cells at various concentrations and the cells were incubated for 5 days. Fresh medium and additional tetracycline compound was added to the cell cultures every 10-14 hours. On the last day of the assay, the cells were washed, harvested and protein extracts prepared. Denatured protein samples were electrophoresed (12% SDS-PAGE) and transferred onto a nitrocellulose membrane. Primary anti-SMN, anti-α-tubulin and secondary Alexa-fluor-532-conjugated antibodies were used to immunostain the membranes. Fluorescence intensity was measured and quantitated using a Fuji laser scanner. The SMN protein signal was normalized to that of tubulin to ensure that the antibodies were not limited and the signals were not saturated.

Figure 4:
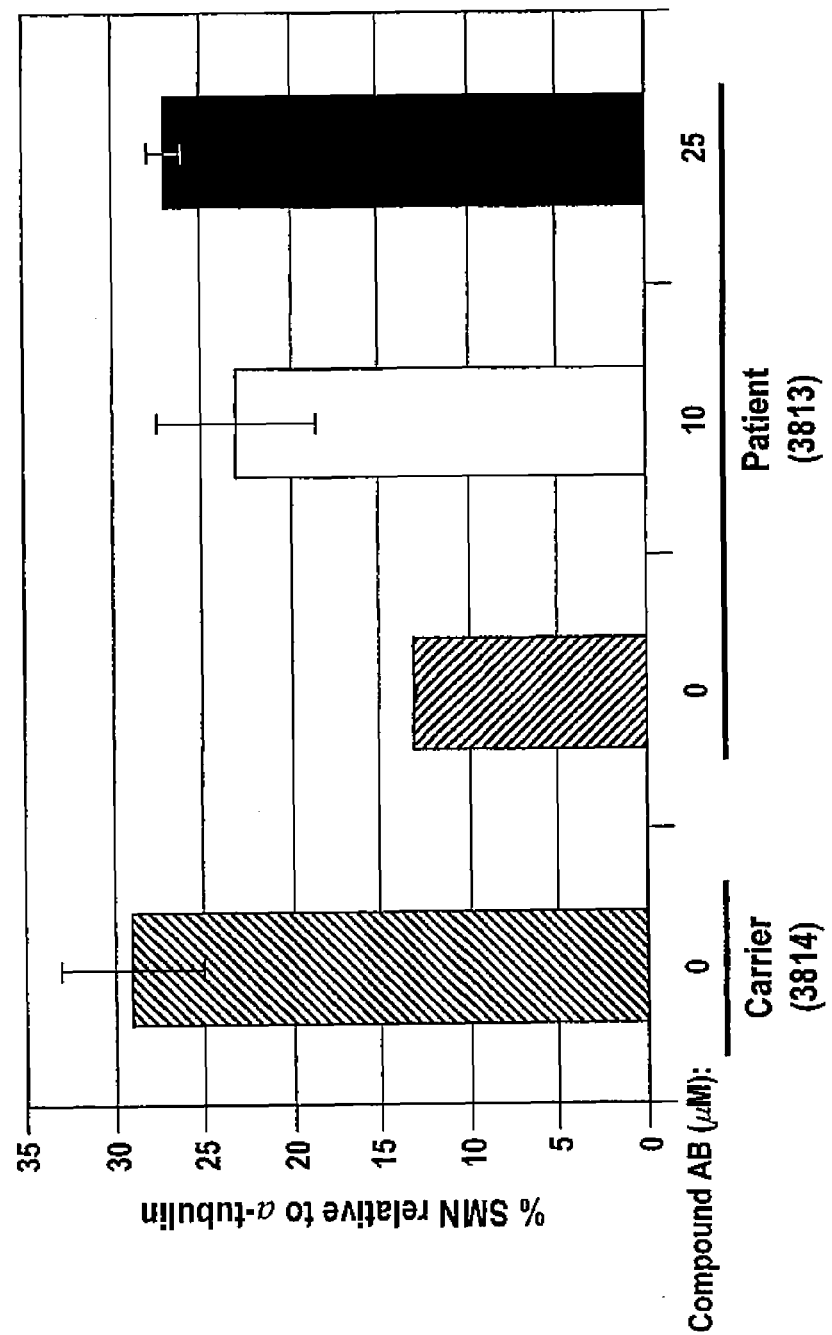
FIG. 4 is a graph illustrating the number of gems/100 cells in an SMA patient cell line treated with compound AB and valproic acid in vitro.

The effect of compound AB on the expression pf SMN protein in 3813 fibroblasts is shown in FIG. 4. At a concentration of 25 μM, the compound increases the expression of SMN protein more than two-fold.

Example 4

In Vivo Mouse Model

The following example illustrates how a tetracycline compound of the invention is active in an in vivo assay for the inclusion of exon 7 in the mRNA in the tissues of SMN2 transgenic mice. Compound AB was administered to mice transgenic for the human SMN2 gene (hSMN2) (see Monani et al. Hum Mol Genet. 9: 2451, incorporated herein in its entirety) intravenously, in the amounts of 10 and 25 mg/kg body weight per day, or intraperitoneally, in the amounts of 25 and 50 mg/kg of body weight per day, for 5 consecutive days. One day after the final dose, the mice were sacrificed, the body organs were harvested, and the mRNA in the cells of the kidney and liver were analyzed for exon 7 inclusion in the hSMN2 transgene by PCR.

PCR was run using a pair of human-specific primers, E4-33 to 55-F (5'-AAGTGAGAACTCCAGGTCTCCTG-3') (SEQ ID NO:1) that anneals in exon 4 and E8-15 to 36-R (5'-GTGGTGTCATTTAGTGCTGCTC-3') (SEQ ID NO:2) that anneals in exon 8. Reactions were run at 94° C. 30 sec, 55° C. 60 sec, 72° C. 2 min for 25 cycles with reactions including α-$^{32}$P-dCTP. RT-PCR products were separated by 6% native PAGE and analyzed by phosphor-image analysis using an Image Reader FLA-5100 (FujiFilm Medical Systems). Exon 7 inclusion was calculated as percentage of the total amount of spliced mRNA by the formula: 100×[exon 7 included mRNA/exon 7 included mRNA+exon 7 excluded mRNA].

Figure 5:
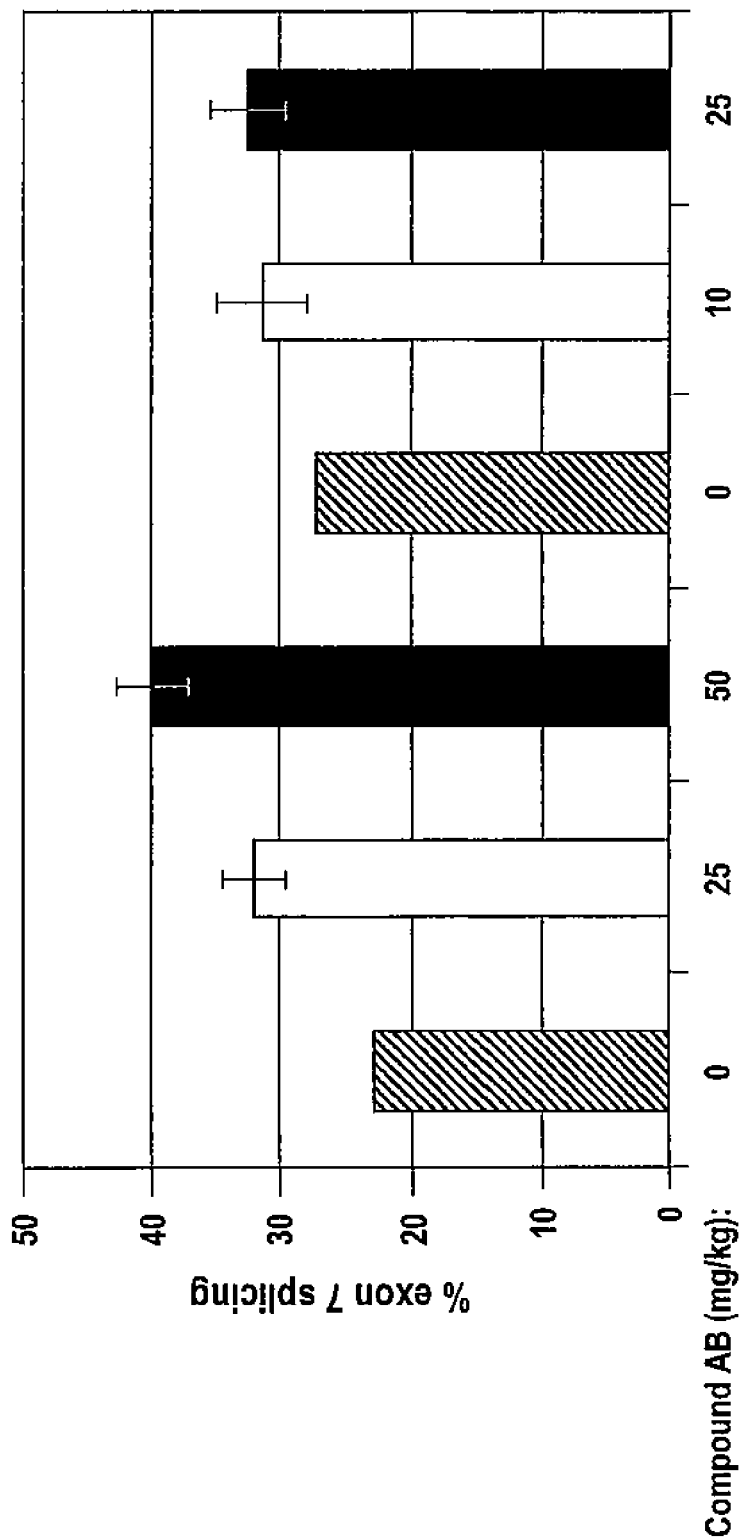
FIG. 5 is a graph illustrating full-length (FL) SMN2 mRNA expression in mouse liver cells as an increase in percentage of exon 7 inclusion as a function of the concentration of AB administered in vivo.
Figure 6:
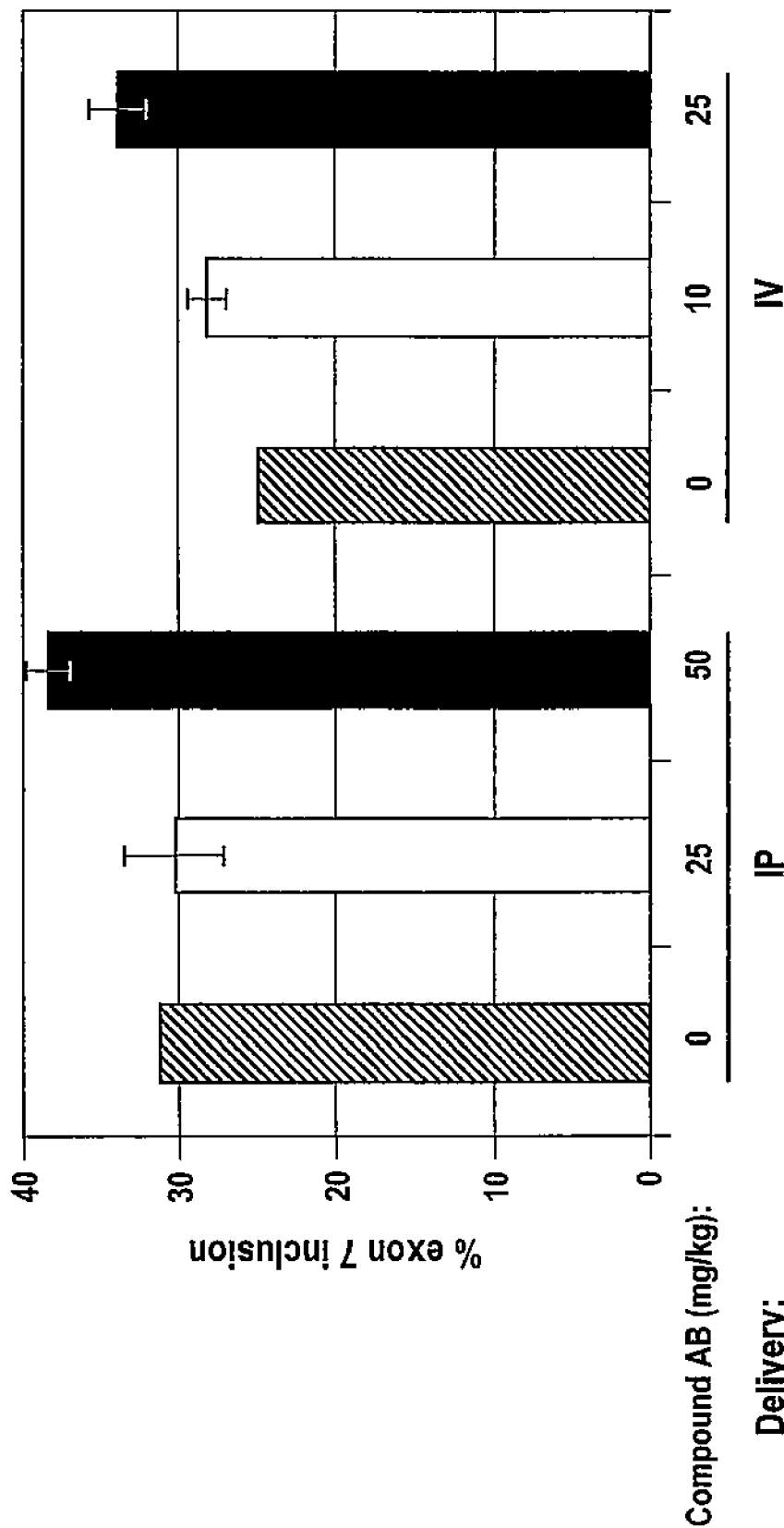
FIG. 6 is a graph illustrating full-length (FL) SMN2 mRNA expression in mouse kidney cells as an increase in percentage of exon 7 inclusion as a function of the concentration of AB administered in vivo.

The results of in vivo administration of compound AB on the hSMN2 mRNA levels in the liver and kidney of transgenic mice are shown in FIGS. 5 and 6, respectively. In general, the cells of the liver and kidney of mice administered compound AB show an increase in the percent of exon 7 splicing when compared to the control mice. The expression of SMN2 mRNA was increased a maximum of about 23% in the kidney tissue and about 74% in the liver tissue compared to non-treated mice.

Example 5

Brain-Penetrating Ability of Tetracycline Compounds

This example demonstrates that selected compounds of the invention have the ability to penetrate the blood-brain barrier. Male CD1 mice were administered various tetracycline compounds (i.v. at a dose of 5 mg/kg). After 15 minutes, 1 hour and 3 hours post-dose, 3 mice were sacrificed, exsanguinated, and brains harvested and snap frozen. Blood was centrifuged and the plasma removed and frozen. Homogenates from plasma and tissue were extracted with 0.1% trifluoroacetic acid in 67% acetonitrile/33% water and compound levels (μg/g tissue) quantitated by HPLC/MS against a standard curve.

Table 3 shows the brain:plasma ratios of selected tetracycline compounds 3 hours after intravenous administration compared to minocycline, a tetracycline previously shown to penetrate the blood-brain barrier.

TABLE 3

| Compound | Ratio of Brain to Plasma Levels (at T = 3 hours, %) |
| --- | --- |
| Minocycline | 127.6 |
| BN | 41.6 |
| BO | 50.7 |

Example 6

Anti-Bacterial Activity

In this example, the gram (+) and gram (−) antibacterial activities of the tetracycline compounds used in the methods of the invention were assessed.

Gram (−) and gram (+) antibacterial minimum inhibitory concentration (MIC) values (μg/mL) were obtained using CLSI methodology for anti-bacterial susceptibility testing. On each day of testing, serial dilutions of compounds were prepared in microdilution plates using a Tecan robotic workstation. Mueller Hinton broth cultures of representative sensitive and resistant gram negative strains were grown or adjusted to match the turbidity of a 0.5 McFarland standard. 1:200 dilutions were made in an appropriate broth (cation supplemented Mueller Hinton broth) to allow a final inoculum of 1×10$^5$ cfu. Plates were incubated at 35° C. in ambient air for 18-24 hours, were read spectrophotometrically and checked manually for evidence of bacterial growth. The lowest dilution of compound that inhibited growth was recorded as the MIC. Lysed horse blood was used to supplement broth for testing *S. pneumoniae*. The MIC's for each compound were assessed against *S. aureus, S. pneumoniae, P. acnes, E. coli* and *B. theta*. The results are shown in Table 4. Good antibacterial activity (e.g., less than about 4 μg/mL) is indicated by "*," modest antibacterial activity (between about 4 and 8 μg/mL) is indicated by "," or weak antibacterial activity (greater than about 8 μg/mL) is indicated by "*." The symbol "−" indicates that no data was obtained.

TABLE 4

| Compound | MIC Gram Positive (SA RN450) μg/mL | MIC Gram Negative (EC D1-209) μg/mL |
| --- | --- | --- |
| A | *** | * |
| C | *** | * |
| D | * | * |
| E | *** | * |
| F | *** | * |
| G | *** | * |
| I | *** | * |
| J | *** | * |
| K | *** | * |
| L | *** | * |
| M | ** | * |
| N | *** | * |
| O | ** | * |
| P | ** | * |
| Q | *** | * |
| R | *** | * |
| S | *** | * |
| T | *** | * |
| U | *** | ** |
| V | * | * |
| W | * | * |
| X | * | * |
| Y | *** | * |
| Z | * | * |
| AA | ** | * |
| AB | *** | * |
| AD | *** | * |
| AE | *** | * |
| AF | *** | *** |
| AG | ** | * |
| AH | * | * |
| AI | *** | * |
| AK | *** | ** |
| AL | *** | * |
| AM | ** | * |
| AO | *** | * |
| AP | *** | * |
| AQ | *** | ** |
| AR | *** | * |
| AS | *** | * |
| AT | *** | *** |
| AU | *** | * |
| AV | *** | * |
| AW | *** | *** |
| AX | *** | ** |
| AY | *** | * |
| AZ | *** | * |
| BA | *** | * |
| BB | *** | * |
| BC | *** | *** |
| BD | *** | * |
| BE | *** | * |
| BF | *** | *** |
| BG | * | * |
| BI | * | * |
| BJ | *** | * |
| BK | *** | * |
| BL | *** | * |

TABLE 4-continued

| Compound | MIC Gram Positive (SA RN450) µg/mL | MIC Gram Negative (EC D1-209) µg/mL |
|---|---|---|
| BM | *** | ** |
| BN | *** | ** |
| BO | *** | * |
| BP | *** | * |
| BQ | *** | * |
| BR | *** | * |
| BS | *** | * |
| BT | *** | * |
| BU | *** | *** |
| BV | *** | * |
| BW | *** | * |
| BX | *** | * |
| BY | *** | * |
| BZ | ** | * |
| CA | *** | * |
| CB | * | * |
| CC | ** | * |
| CD | ** | * |
| CE | *** | * |
| CF | ** | * |
| CG | *** | * |
| CH | ** | * |
| CI | *** | * |
| CJ | *** | * |
| CK | *** | * |
| CL | ** | * |
| CM | *** | * |
| CN | * | * |

Example 7

Phototoxic Potential

In this example, the phototoxic potential of the tetracycline compounds used in the methods of the invention was assessed. In particular, 3T3 fibroblast cells were harvested and plated at a concentration of $1 \times 10^5$ cells/mL and the plates were incubated overnight at 37° C., in 5% $CO_2$ and approximately 95% humidity. On the following day the medium was removed from the plates and replaced with Hanks' Balanced Salt Solution (HBSS). Drug dilutions were made in HBSS and added to the plates. For each compound tested, a duplicate plate was prepared that was not exposed to light as a control for compound toxicity. Plates were then incubated in a dark drawer (for controls), or under UV light (meter reading of 1.6-1.8 mW/cm$^2$) for 50 minutes. Cells were then washed with HBSS, fresh medium was added, and plates were incubated overnight as described above. The following day neutral red was added as an indicator of cell viability. The plates were then incubated for an additional 3 hours. Cells were then washed with HBSS and blotted on absorbent paper to remove excess liquid. A solution of 50% EtOH, 10% glacial acetic acid was added and after 20 minutes incubation, and the plate's absorbance at 535 nm was read using a Wallac Victor 5 spectrophotometer. The phototoxicity reflected the difference between the light-treated and control cultures. The results are given in Table 5. Results for doxycycline and minocycline are shown for comparison. Compounds which showed phototoxicity are indicated by "**" (e.g., less than 5 µg/mL), compounds which showed moderate phototoxicity are indicated by "*" (e.g., greater than about 5 µg/mL and less than about 25 µg/mL), compounds which showed some phototoxicity are indicated by "**" (e.g., greater than about 25 µg/mL and less than about 75 µg/mL) and compounds that showed minimal or no phototoxicity are indicated by "*" (e.g., greater than about 75 µg/mL).

TABLE 5

| Compound | Dark Tox50 (uM) | UV Tox50 (uM) |
|---|---|---|
| A | * | * |
| C | * | * |
| D | * | * |
| E | * | * |
| F | * | * |
| G | * | *** |
| I | * | * |
| J | * | * |
| K | * | * |
| L | * | * |
| M | * | * |
| N | * | * |
| O | * | * |
| P | * | * |
| Q | * | * |
| R | * | * |
| S | * | * |
| T | * | * |
| U | * | * |
| V | * | * |
| W | * | * |
| X | * | * |
| Y | * | * |
| Z | * | * |
| AA | * | * |
| AB | * | * |
| AD | * | * |
| AE | * | * |
| AF | * | * |
| AG | * | * |
| AH | * | * |
| AI | * | * |
| AK | * | * |
| AL | * | * |
| AM | * | * |
| AO | * | * |
| AP | * | * |
| AT | * | * |
| AV | * | * |
| AZ | * | * |
| BB | * | * |
| BC | * | * |
| BD | * | * |
| BE | * | * |
| BF | * | * |
| BG | * | * |
| BI | * | * |
| BJ | * | * |
| BK | * | * |
| BL | * | * |
| BM | * | *** |
| BN | * | * |
| BO | * | * |
| BP | * | * |
| BQ | * | * |
| BR | * | * |
| BS | * | * |
| BT | * | * |
| BU | * | * |
| BV | * | * |
| BW | * | * |
| BX | * | * |
| BY | * | * |
| BZ | * | * |
| CA | * | * |
| CB | * | * |
| CC | * | * |
| CD | * | * |
| CE | * | * |
| CF | * | * |
| CG | * | * |
| CH | * | * |
| CI | * | * |
| CJ | * | * |
| CK | * | * |
| CL | * | * |
| CM | * | * |

TABLE 5-continued

| Compound | Dark Tox50 (uM) | UV Tox50 (uM) |
|---|---|---|
| CN | * | * |
| Doxycycline | * | * |
| Minocycline | * | * |

Example 8

Synthesis of Selected Substituted Tetracycline Compounds

7-[2-(4-methyl-piperidin-1-yl)acetyl]-Sancycline (Compound BH)

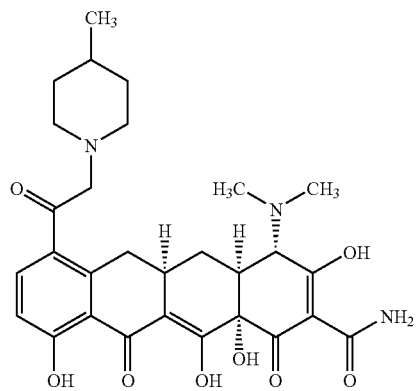

An amount of 7-acetyl sancycline (1 g, 2.19 mmol) was combined with acetic acid (4 mL), water (1 mL) and HBr (33 wt % solution in HOAc) (2 mL, 0.01 mmol) in a 40 mL glass vial. An argon line was attached to the septum and the reaction mixture was stirred until contents dissolved (5 minutes). Bromine (0.15 mL, 1.21 μmol) was added dropwise to reaction solution and an exotherm was detected. The reaction was monitored by HPLC and LC-MS and starting material was consumed within 15 minutes. Mono and bis-substituted bromine products were both detected. The reaction solution was precipitated in 400 mL diethyl ether and a bright yellow solid formed. The ether was decanted and 400 mL fresh ether added, and decanted once again. An amount of acetonitrile (300 mL) was added to the yellow precipitate and the mixture was filtered through filter paper. The filtrate was dried in vacuo to yield a dark yellow solid (1 g). The crude bromoacetyl sancycline was dissolved in DMF (20 mL) in a 100 mL round bottom flask. The argon line was attached to reaction and TEA (1 mL, 7.19 mmol) was added, followed by 4-methylpiperidine (1 mL, 8.1 mmol). The reaction was monitored by HPLC and LC-MS. Methanol (50 mL) was added to quench the reaction, and the solvent was dried in vacuo. The crude material was purified in 3 batches on a 2" C-18 Luna column using a 10-30% organic gradient ($CH_3CN$ with 0.1% TFA and water with 0.1% TFA) over 35 minutes. The purified compound was dried in vacuo and redissolved in methanol (20 mL) saturated with HCl to exchange the salt. The compound was dried overnight over $P_2O_5$ to yield BH (110 mg, 11%) as a yellow powder. MS: (m/z) 553. $^1$H NMR ($CD_3OD$) δ 7.99 (1H, m), 6.93 (1H, m), 4.89 (1H, m), 4.61 (1H, m), 4.07 (1H, s), 3.68 (1H, m), 3.56 (1H, m), 3.30 (1H, m), 3.11 (2H, m), 3.01 (7H, m), 2.47 (1H, m), 2.15 (1H, m), 1.89 (2H, m), 1.55 (4H, m), 0.96 (3H, d, J=9 Hz). Compounds AG, AJ, AM, BB, BO, BP, BR, BS, BT, BU, BV, BW, BX, BY, BZ, CA, CB, CC, CE, CF and CH were prepared in a similar manner.

3-[3-(((6aS,10S,10aS,11aR)-8-Carbamoyl-10-dimethylamino-4,6,6a,9-tetrahydroxy-5,7-dioxo-5,6a,7,10,10a,11,11a,12-octahydro-naphthacen-1-yl)-benzoylamino]-propionic Acid Ethyl Ester (Compound I)

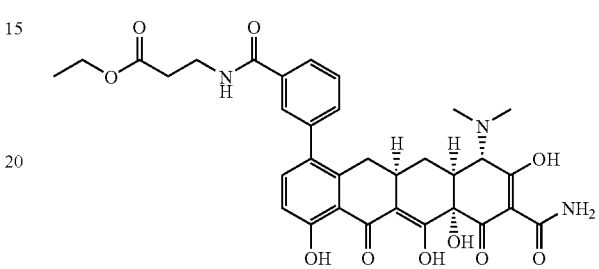

An amount 1.00 g of 7-iodosancycline trifluoroacetic acid salt, 177 mg of palladium (0) tetrakistriphenylphosphine, 35 mg of palladium (II) acetate and 457 mg of 3-(3-ethoxy-3-pxopropylcarbamoyl)phenylboronic acid, 98% were loaded in a dry 20 mL microwave reaction vessel equipped with a magnetic stir bar. Dry dimethylacetamide (DMA, 10 mL) was added and argon was bubbled through the solution for 5 minutes. In a separate vial, sodium acetate (487 mg) was dissolved in distilled water (5 mL) and argon was bubbled through the solution for 5 minutes. The sodium acetate solution was added to the microwave reaction vessel which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (divinylbenzene) column with gradients of a 50/50 methanol/acetonitrile, 0.1% TFA solution into a 0.1% TFA water solution. The fractions were collected and evaporated to a minimum volume. The residue was then purified by preparative HPLC chromatography (C18, linear gradient 27-32% acetonitrile in water with 0.2% formic acid). The fractions were evaporated and the resulting residue was purified again by preparative HPLC chromatography (C18, linear gradient 20-35% acetonitrile in 20 mM aqueous triethanolamine, pH 7.4) in order to separate the 4-epimers. The fractions were collected and the organic solvent was evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 634 (MH+). 1H-NMR (300 MHz, tetramethylsilane (TMS) as internal standard at 0 ppm): (ppm) 7.78 (dm, 1H), 7.70 (m, 1H), 7.51 (t, 1H), 7.45 (d, 2H), 6.92 (d, 1H), 4.13 (q, 2H), 4.00 (s, 1H), 3.63 (t, 2H), 2.97-2.80 (m, 8H), 2.77 (dd, 1H), 2.64 (t, 2H), 2.52 (t, 1H), 2.08-1.95 (m, 1H), 1.53 (q, 1H), 1.23 (t, 3H). Compounds A, B, C, D, F, G, H, J, L, P, W, Y, AA, AB, AC, AD, AE, AF, AO, AQ, AR, AS, AT, AU, AW, AX, AY, AZ AP, BC, BE, BF, BG, BI, BJ, BK, BL, BM, BN, B1, CO, CK and CM were prepared in a similar manner.

(4S,4aS,5aR,12aS)-4-Dimethylamino-7-[(4-dimethyl-lamino-butylamino)-methyl]-3,10,12,12a-tetrahydroxy-1,11-dioxo-1,4,4a,5,5a,6,11,12a-octahydro-naphthacene-2-carboxylic Acid Amide. (Compound CN)

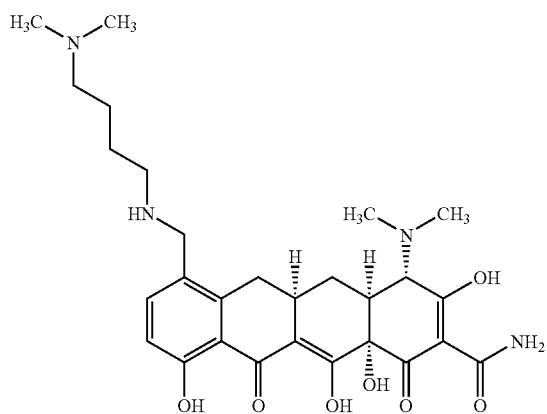

The TFA salt of 7-formyl-sancycline (50 mg, 0.09 mmol) was dissolved in dry tetrahydrofuran (THF, 2 mL) at room temperature in a flask equipped with a magnetic stirring bar. Enough di-isopropylethylamine (DIEA) was added to adjust the pH to about 7. N,N-Dimethyl-4-amino-butylamine (22 mg, 0.18 mmol, 2.0 eq) was added and the reaction mixture was stirred at room temperature for 15 minutes. Sodium triacetoxyborohydride (59 mg, 0.27 mmol, 3.0 eq) was added at room temperature and the reaction is monitored by LC/MS. After 2 hours, the reaction was completed and after filtration of the mixture, the residue was purified by preparative HPLC (C18, linear gradient acetonitrile in water with 0.2% formic acid). The fractions were combined, evaporated and the resulting residue was purified again by preparative HPLC chromatography (C18, linear gradient acetonitrile in 20 mM aqueous triethanolamine, pH 7.4) in order to separate the 4-epimers. The fractions were collected and the organic solvent evaporated. The resulting aqueous solution was loaded on a DVB column, washed with DI water and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. $^1$H-NMR (chemical shifts in ppm with TMS as internal reference at 0 ppm, in deuterated methanol): δ 7.64 (1H, doublet, aromatic), δ 6.92 (1H, doublet, aromatic), δ 4.25 (2H, singlet), δ 4.12 (1H, singlet), δ 3.30-2.80 (19H, multiplet), δ 2.48 (1H, multiplet), δ 2.35 (1H, multiplet), δ 1.85 (4H, multiplet), δ 1.62 (1H, multiplet). Mass Spectroscopy (Electron Spray): M+1=543. Compound AK was prepared in a similar manner.

(4S,4aS,5aR,12aS)-7-[3-(2-Diethylamino-ethylcarbamoyl)-phenyl]-4-dimethylamino-3,10,12,12a-tetrahydroxy-1,11-dioxo-1,4,4a,5,5a,6,11,12a-octahydro-naphthacene-2-carboxylic Acid Amide (Compound E)

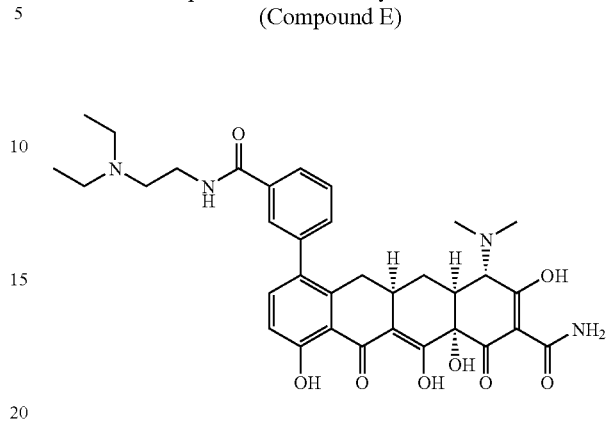

An amount of 2.5 g of 7-iodosancycline trifluoroacetic acid salt, 221 mg of palladium (0) tetrakistriphenylphosphine, 43 mg of palladium (II) acetate and 777 mg of 3-carboxy-phenylboronic acid were loaded in a dry 20 mL microwave reaction vessel equipped with a magnetic stir bar. Dry DMA (13 mL) was added and argon was bubbled through the solution for 5 minutes. In a separate vial, sodium acetate (105.99 g/mol, 1.215 g, 11.46 mmol, 3.0 eq.) was dissolved in distilled water (7 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (divinylbenzene) column with gradients of a 50/50 methanol/acetonitrile, 0.1% TFA solution into a 0.1% TFA water solution. The fractions were collected and evaporated to dryness to yield an orange solid, which was used in the next step without further purification.

An amount of 340 mg of 7-(3-carboxy-phenyl)-sancycline TFA salt and 212 mg of O-benzotriazol-1-yl-N,N,N'N'-tetramethyluronium hexafluoro-phosphate were loaded in a dry 10 mL vial equipped with a magnetic stir bar. Dry DMA (2.5 mL) was added, followed by diisopropylethylamine (180 μL). After 5 minutes of stirring at room temperature, N,N-diethyl-ethylenediamine, 98% (150 μL) was added, the reaction mixture was stirred at room temperature for 15 minutes and the reaction was monitored by LC/MS. The mixture was filtered through celite, evaporated in a rotary evaporator, and the residue was purified by preparative HPLC chromatography (C18, linear gradient 25-35% acetonitrile in water with 0.2% formic acid). The fractions were combined, evaporated, and the resulting residue was purified again by preparative HPLC chromatography (C18, linear gradient 20-35% acetonitrile in 20 mM aqueous triethanolamine, pH 7.4) in order to separate the 4-epimers. The fractions were collected and the organic solvent evaporated. The resulting aqueous solution was loaded on a DVB column, washed with DI water, and then washed with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt.

ESIMS: m/z 633 (MH+). 1H-NMR (300 MHz, tetramethylsilane (TMS) as internal standard at 0 ppm): (ppm) 7.87 (dm, 1H), 7.79 (m, 1H), 7.60-7.47 (m, 2H), 7.44 (d, 1H), 6.93 (d, 1H), 4.02 (s, 1H), 3.76 (t, 2H), 3.45-3.30 (m, 6H), 3.02-2.85 (m, 8H), 2.78 (dd, 1H), 2.54 (t, 1H), 2.10-1.95 (m, 1H), 1.53 (q, 1H), 1.35 (t, 6H). Compounds M, N, O, R, S, T, U, CL, CP, CQ and CR were prepared in a similar manner.

(4S,4aS,5aR,12aS)-4-Dimethylamino-7-(3-{[(3-dimethylamino-propyl)-methyl-amino]-methyl}-phenyl)-3,10,12,12a-tetrahydroxy-1,11-dioxo-1,4,4a,5,5a,6,11,12a-octahydro-naphthacene-2-carboxylic Acid Amide (Compound CU)

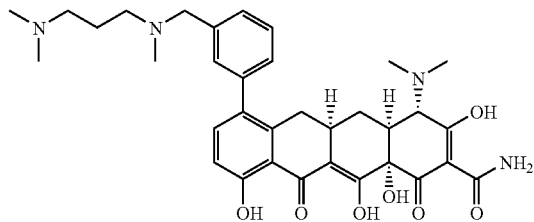

The TFA salt of 7-(3-formyl)-phenyl-sancycline (200 mg, 0.32 mmol) was dissolved in dry dimethylacetamide (DMA, 2 mL) at room temperature in a flask equipped with a magnetic stirring bar. Enough di-isopropylethylamine (DIEA) was added to adjust the pH to about 7. N,N,N'-Trimethyl-3-amino-propylamine (46 mg, 0.40 mmol) was added and the reaction mixture is stirred at room temperature for 15 minutes. Sodium triacetoxyborohydride (83 mg, 0.39 mmol, 1.2 eq) was added at room temperature and the reaction was monitored by LC/MS. After 2 hours, the reaction was complete and after filtration of the mixture, the residue was purified by preparative HPLC (C18, linear gradient 15-35% acetonitrile in water with 0.2% formic acid). The fractions were combined, evaporated, and the resulting residue was purified again by preparative HPLC chromatography (C18, linear gradient 15-35% acetonitrile in 20 mM aqueous triethanolamine, pH 7.4) in order to separate the 4-epimers. The fractions were collected and the organic solvent evaporated. The resulting aqueous solution was loaded on a DVB column, washed with DI water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. 1H-NMR (chemical shifts in ppm with TMS as internal reference at 0 ppm, in deuterated methanol): δ 7.60-7.30 (5H, multiplet, aromatic), δ 7.12 (1H, doublet, aromatic), δ 4.28 (2H, singlet), δ 4.09 (1H, singlet), δ 3.17 (4H, multiplet), δ 3.05-3.75 (18H, multiplet), δ 2.54 (1H, multiplet), δ 2.09 (1H, multiplet), δ 1.83 (2H, multiplet), δ 1.53 (1H, multiplet). Mass Spectroscopy (Electron Spray): M+1=619. Compounds AX, AY, AZ, BF, BI, BK, BQ, CS, CT, CV, CW, CX were prepared in a similar manner.

(4S,4aS,5aR,12aS)-4,7-Bis-dimethylamino-9-[3-(2-dimethylamino-ethylcarbamoyl)-phenyl]-3,10,12,12a-tetrahydroxy-1,11-dioxo-1,4,4a,5,5a,6,11,12a-octahydro-naphthacene-2-carboxylic Acid Amide (Compound V)

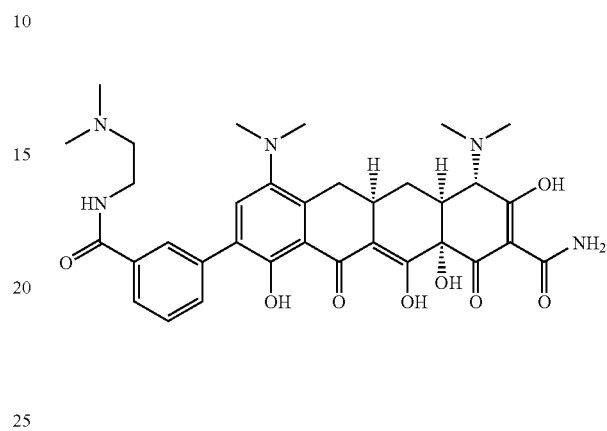

An amount of 500 mg of 9-iodo-minocycline free base, 100 mg of palladium (0) tetrakis triphenylphosphine, 20 mg of palladium (II) acetate and 234 mg of [3-(3-N,N-dimethylaminoetylaminocarbonyl)-phenyl]-boronic acid were loaded in a dry 20 mL microwave reaction vessel equipped with a magnetic stir bar. Dry DMA (4 mL) was added and argon was bubbled through the solution for 5 minutes. In a separate vial, sodium acetate (274 mg) was dissolved in DI water (2 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to a minimum volume. The residue was then purified by HPLC chromatography (C18, linear gradient 10-20% acetonitrile in water with 0.2% formic acid). The fractions were combined, evaporated, and the resulting residue was purified again by preparative HPLC chromatography (C18, linear gradient 10-20% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 648 (MH+). 1H-NMR (300 MHz, tetramethylsilane (TMS) as internal standard at 0 ppm): (ppm) 8.26 (t, 1H), 8.16 (s, 1H), 7.94 (m, 2H), 7.59 (t, 1H), 4.19 (s, 1H), 3.82 (t, 2H), 3.50-3.30 (m, 9H), 3.30-3.10 (m, 2H), 3.10-2.90 (m, 9H), 2.62 (t, 1H), 2.42-2.30 (m, 1H), 1.71 (q, 1H). Compound X, BA and CD were prepared in a similar manner.

115

(4aS,5aR,12aS)-7-[3-(2-Dimethylamino-ethylcarbamoyl)-phenyl]-3,10,12,12a-tetrahydroxy-1,11-dioxo-1,4,4a,5,5a,6,11,12a-octahydro-naphthacene-2-carboxylic Acid Amide (Compound Z)

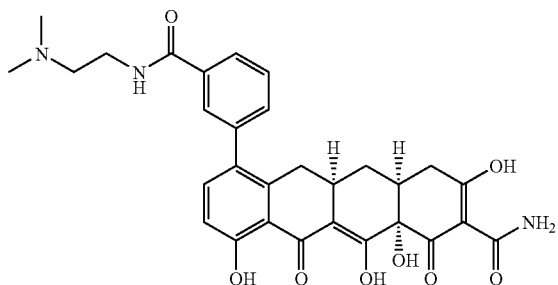

An amount of 1.00 g of 7-iodo-4-dedimethylamino-sancycline free base, 233 mg of palladium (0) tetrakis triphenylphosphine, 45 mg of palladium (II) acetate and 544 mg of [3-(3-N,N-dimethylaminoethylaminocarbonyl)-phenyl]-boronic acid were loaded in a dry 20 mL microwave reaction vessel equipped with a magnetic stir bar. Dry DMA (8 mL) was added and argon was bubbled through the solution for 5 minutes. In a separate vial, sodium acetate (640 mg) was dissolved in distilled water (4 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C. and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to a minimum volume. The residue was then purified by preparative HPLC chromatography (C18, linear gradient 20-35% acetonitrile in water with 0.2% formic acid). The fractions were combined, evaporated, and the resulting residue was purified again by preparative HPLC chromatography (C18, linear gradient 15-35% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 562 (MH+). 1H-NMR (300 MHz, tetramethylsilane (TMS) as internal standard at 0 ppm): (ppm) 7.87 (dm, 1H), 7.78 (s, 1H), 7.60-7.45 (m, 2H), 7.41 (d, 1H), 6.90 (d, 1H), 3.76 (m, 2H), 3.38 (t, 2H), 3.21 (dd, 1H), 2.98 (s, 6H), 2.85-2.62 (m, 2H), 2.57-2.22 (m, 3H), 1.90-1.80 (m, 1H), 1.48 (q, 1H).

116

(4S,4aS,5aR,12aS)-4-Dimethylamino-7-[3-(2-dimethylamino-acetylamino)-phenyl]-3,10,12,12a-tetrahydroxy-1,11-dioxo-1,4,4a,5,5a,6,11,12a-octahydro-naphthacene-2-carboxylic Acid Amide (Compound K)

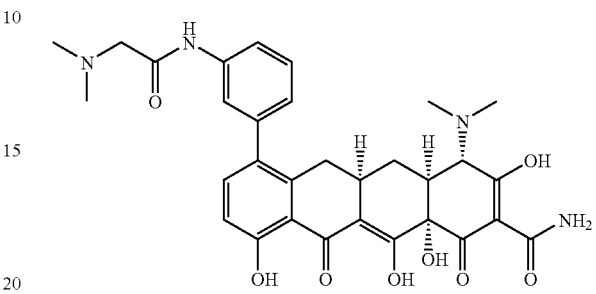

An amount of 2.50 g of 7-iodosancycline trifluoroacetic acid salt, 221 mg palladium (0) tetrakis triphenylphosphine, 42 mg of palladium (II) acetate, and 812 mg of 3-aminophenylboronic acid were loaded in a dry 20 mL microwave reaction vessel equipped with a magnetic stir bar. Dry DMA (13 mL) was added and argon was bubbled through the solution for 5 minutes. In a separate vial, sodium acetate (1.22 g) was dissolved in distilled water (7 mL) and argon was bubbled through the solution for 5 minutes. The sodium acetate solution was added to the microwave reaction vessel, which was sealed with a crimper. The reaction mixture was then subjected to microwave irradiation for 20 minutes at 120° C., and the reaction was monitored by LC/MS. The reaction mixture was then filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to dryness to yield a brown solid which is used in the next step without further purification.

An amount of 250 mg of 7-(3-amino-phenyl)-sancycline TFA salt and 250 µL of diisopropylethylamine were loaded into a dry 5 mL microwave reaction vessel equipped with a magnetic stir bar. After 5 minutes of stirring, dimethylamino acetyl chloride, 85% (667 mg) was added, the reaction vessel was sealed, the reaction mixture was subjected to microwave irradiation for 5 minutes at 100° C. and the reaction was monitored by LC/MS. The mixture was filtered through celite, evaporated in a rotary evaporator, and the residue was purified by preparative HPLC chromatography (C18, linear gradient 10-30% acetonitrile in water with 0.2% formic acid). The fractions were combined, evaporated, and the resulting residue was purified again by preparative HPLC chromatography (C18, linear gradient 15-25% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and P2O5 overnight to yield a yellow solid as an HCl salt. ESIMS: m/z 591 (MH+). 1H-NMR (300 MHz, tetramethylsilane (TMS) as internal standard at 0 ppm): (ppm) 7.56 (m, 2H), 7.45-7.32 (m, 2H), 7.07 (d, 1H), 6.91 (d, 2H), 4.15 (s, 2H), 4.04 (s, 1H), 3.20-2.70 (m, 15H), 2.48 (t, 1H), 2.04 (m, 1H), 1.51, (m, 1H). Compound Q was prepared in a similar manner.

Equivalents

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

The invention claimed is:

1. A method for treating a subject for spinal muscular atrophy, comprising: administering to said subject an effective amount of a tetracycline compound of formula I:

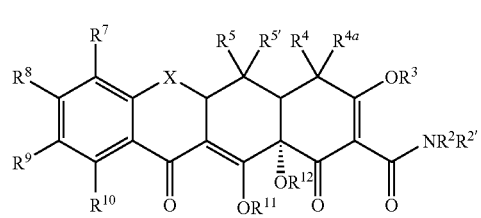

wherein
X is $CR^{6'}R^6$;
$R^2$ and $R^{2'}$ are each hydrogen;
$R^{4'}$ and $R^{4''}$ are each alkyl;
$R^3$, $R^{4a}$, $R^{11}$ and $R^{12}$ are each hydrogen;
$R^4$ is $NR^{4'}R^{4''}$;
$R^5$ and $R^{5'}$ are each hydrogen;
$R^6$ and $R^{6'}$ are each hydrogen;
$R^7$ is acyl, amino, phenyl, pyridinyl, furanyl, pyrrolyl, tetrahydropyridinyl, quinolinyl, or aminoalkyl;
$R^8$ is hydrogen;
$R^9$ is hydrogen or phenyl; and
$R^{10}$ is hydroxyl;
or a pharmaceutically acceptable salt, ester or enantiomer thereof, such that said spinal muscular atrophy in said subject is treated.

2. The method of claim 1, wherein $R^7$ is amino.

3. The method of claim 2, wherein said amino is dialkylamino.

4. The method of claim 3, wherein said dialkylamino is dimethylamino.

5. The method of claim 1, wherein $R^9$ is hydrogen.

6. The method of claim 5, wherein $R^7$ is phenyl or pyridinyl, and further wherein said phenyl or pyridinyl is of formula V:

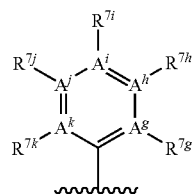

wherein
$A^g$, $A^i$, $A^j$ and $A^k$ are each C and $A^h$ is N or C; and
when $A^h$ is C, then $R^{7g}$, $R^{7h}$, $R^{7i}$, $R^{7j}$ and $R^{7k}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7j}$ and $R^{7i}$ are linked to form a 5- or 6-membered aryl, heterocyclic or aliphatic ring; or
$R^{7h}$ is absent when $A^h$ is N.

7. The method of claim 6, wherein $A^h$ is C.

8. The method of claim 7, wherein $R^{7g}$, $R^{7h}$, $R^{7i}$ and $R^{7k}$ are each hydrogen.

9. The method of claim 6, wherein $R^{7j}$ is carbonyl, and further wherein said carbonyl is of formula VI:

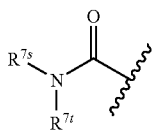
(VI)

wherein
R$^{7s}$ and R$^{7t}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7s}$ and R$^{7t}$ are linked to form a 5- or 6-membered aryl, heterocyclic or aliphatic ring.

10. The method of claim 9, wherein R$^{7t}$ is hydrogen.

11. The method of claim 9, wherein R$^{7s}$ is alkyl, and further wherein said alkyl is of formula VII:

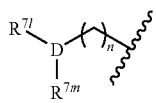
(VII)

wherein
D is O, N, NR$^{7'}$ or CR$^{7'}$;
n is an integer from 0 to 10;
R$^{7'}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
when D is N or CR$^{7'}$, R$^{71}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{71}$ and R$^{7m}$ are linked to form a 5- or 6-membered aryl, heterocyclic or aliphatic ring; or
when D is O, R$^{71}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic and R$^{7m}$ is absent.

12. The method of claim 11, wherein D is N.
13. The method of claim 11, wherein n is 2.
14. The method of claim 11, wherein R$^{71}$ and R$^{7m}$ are each alkyl.
15. The method of claim 14, wherein said alkyl is methyl.
16. The method of claim 9, wherein R$^{7s}$ and R$^{7t}$ are each hydrogen.
17. The method of claim 9, wherein R$^{7s}$ and R$^{7t}$ are each alkyl.
18. The method of claim 17, wherein said alkyl is methyl.
19. The method of claim 9, wherein R$^{7s}$ and R$^{7t}$ are linked to form a 6-membered heterocyclic ring.
20. The method of claim 11, wherein D is N or O.
21. The method of claim 11, wherein n is 1, 2, 3 or 4.
22. The method of claim 11, wherein R$^{71}$ is aryl.
23. The method of claim 21, wherein R$^{71}$ and R$^{7m}$ are each alkyl.
24. The method of claim 21, wherein R$^{71}$ and R$^{7m}$ are each hydrogen.
25. The method of claim 21, wherein R$^{7m}$ is alkyl or acyl.
26. The method of claim 21, wherein R$^{71}$ and R$^{7m}$ are linked to form a 5- or 6-membered heterocyclic ring.
27. The method of claim 9, wherein R$^{7s}$ is alkyl and further wherein said alkyl is alkoxycarbonyl substituted alkyl, heterocyclic substituted alkyl, or hydroxyl substituted alkyl.

28. The method of claim 6, wherein R$^{7i}$ and R$^{7j}$ are linked to form a 6-membered aryl ring.
29. The method of claim 28, wherein said aryl ring is a benzene ring.
30. The method of claim 6, wherein R$^{7j}$ is acyl.
31. The method of claim 6, wherein R$^{7j}$ is carbonyl.
32. The method of claim 31, wherein said carbonyl is alkoxy substituted carbonyl.
33. The method of claim 6, wherein A$^{h}$ is N.
34. The method of claim 33, wherein R$^{7g}$, R$^{7j}$ and R$^{7k}$ are each hydrogen.
35. The method of claim 5, wherein R$^{7}$ is tetrahydropyridinyl.
36. The method of claim 35, wherein R$^{7}$ is

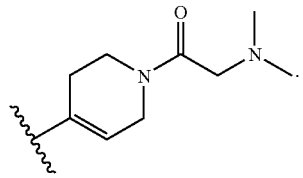

37. The method of claim 5, wherein R$^{7}$ is quinolinyl.
38. The method of claim 5, wherein R$^{7}$ is furanyl or pyrrolyl, and further wherein said furanyl or pyrrolyl is of formula X:

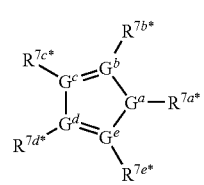
(X)

wherein
G$^{a}$ is N or O;
G$^{b}$, G$^{c}$, G$^{d}$ and G$^{e}$ are each CR$^{7f*}$,
R$^{7f*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;
R$^{7a*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic when G$^{a}$ is N or R$^{7a*}$ is absent when G$^{a}$ is O;
R$^{7b*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;
R$^{7c*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic;
R$^{7d*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7d*}$ is covalently bonded to the 7-position of the tetracycline compound; and
R$^{7e*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7e*}$ is covalently bonded to the 7-position of the tetracycline compound;
provided that one of R$^{7d*}$ or R$^{7e*}$ are covalently bonded to the 7-position of the tetracycline compound.

39. A method for treating a subject for spinal muscular atrophy, comprising administering to said subject an effective amount of a tetracycline compound selected from:

121 122
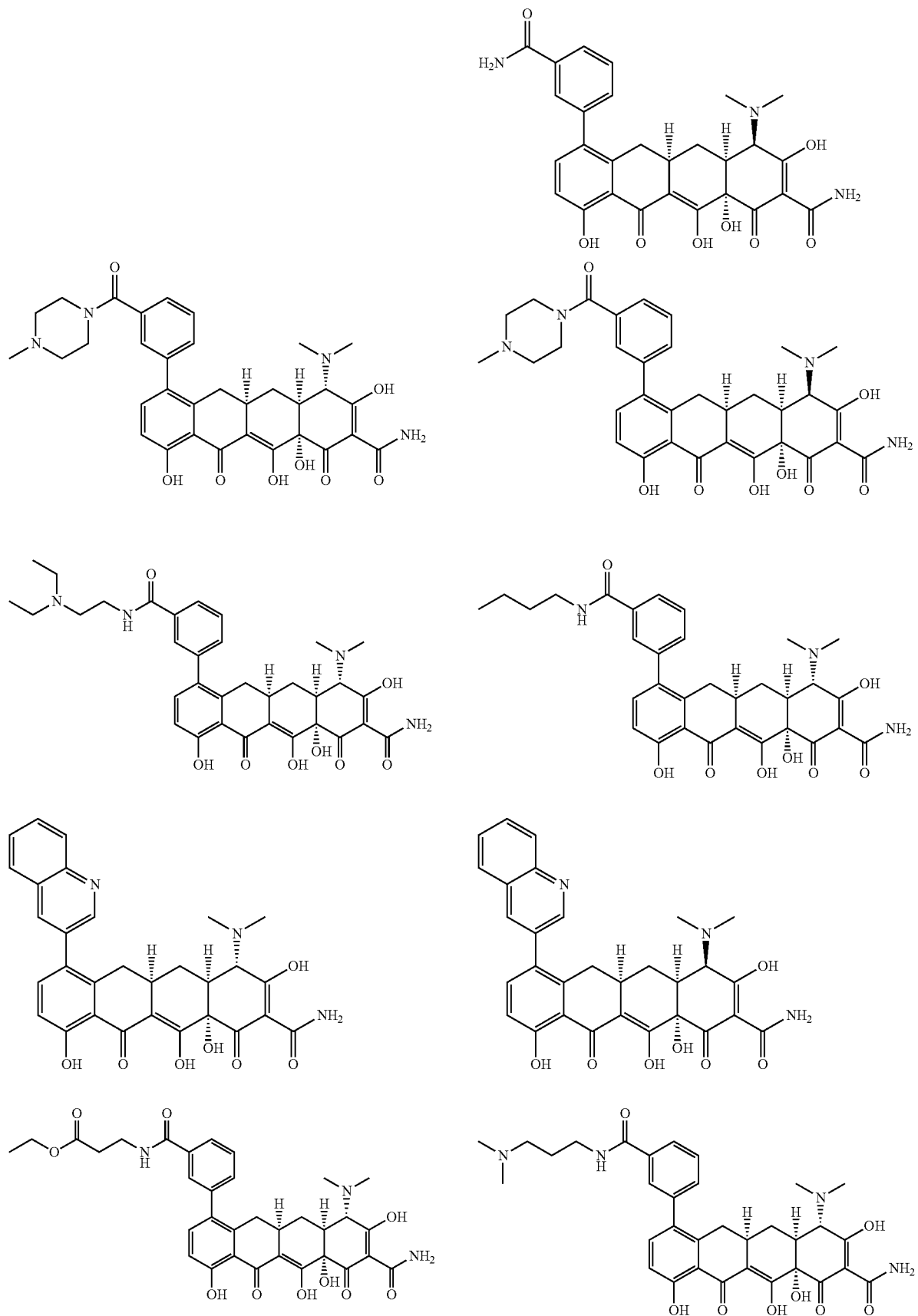

123 124
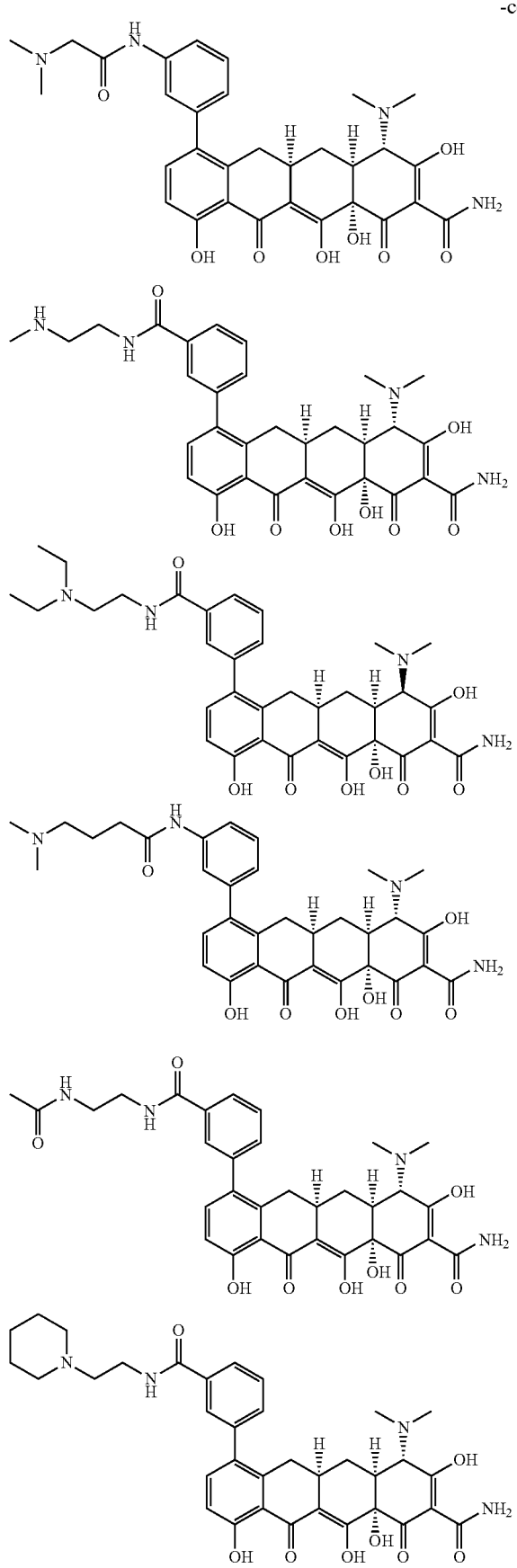
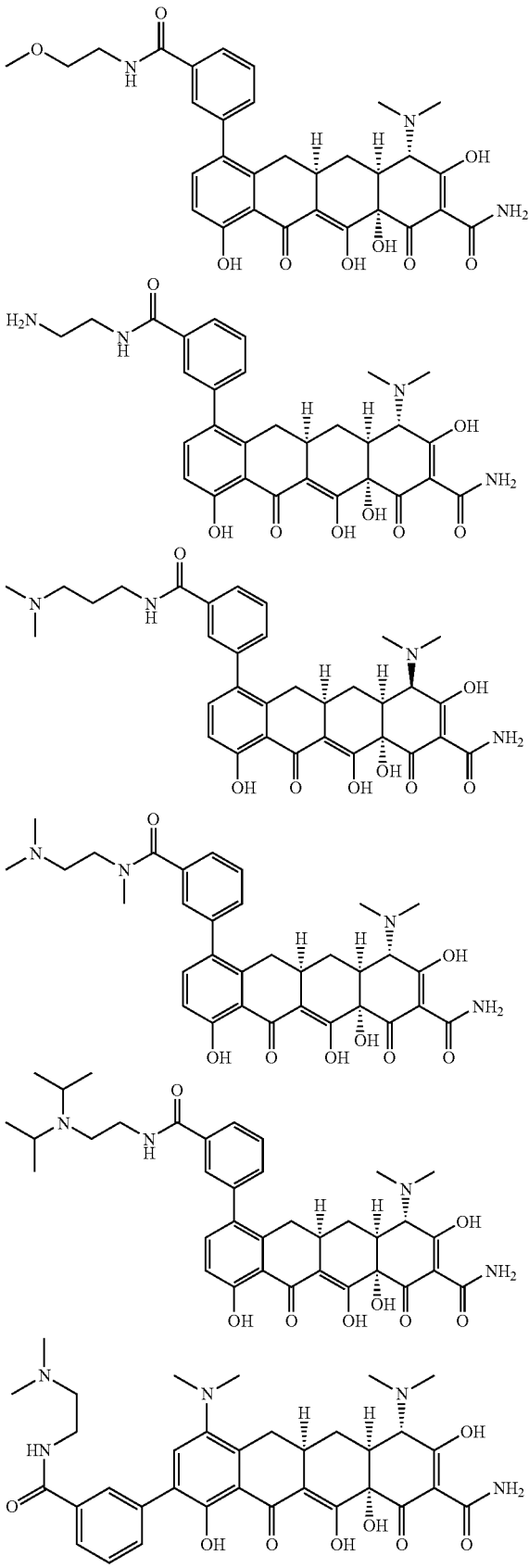

125 126
-continued
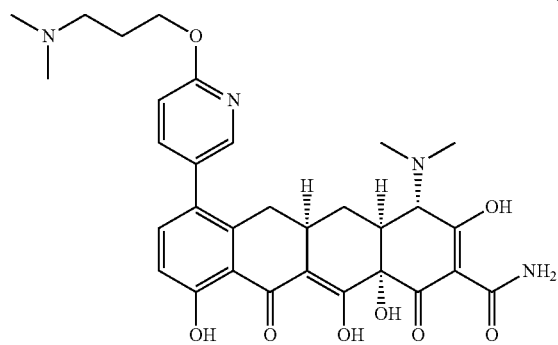
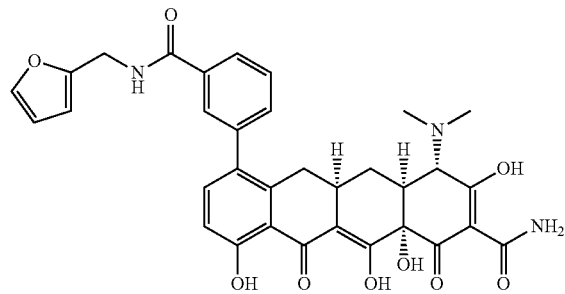
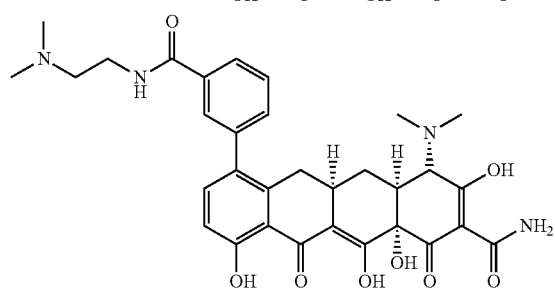
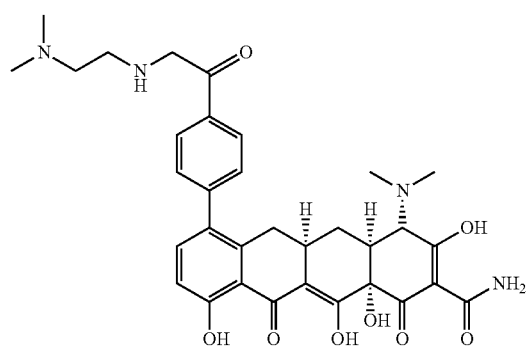
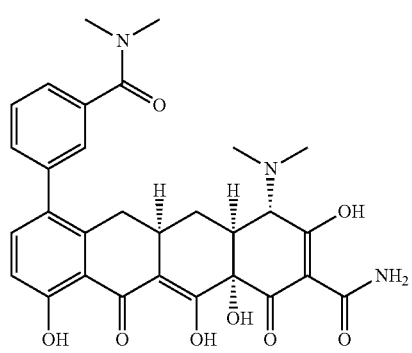
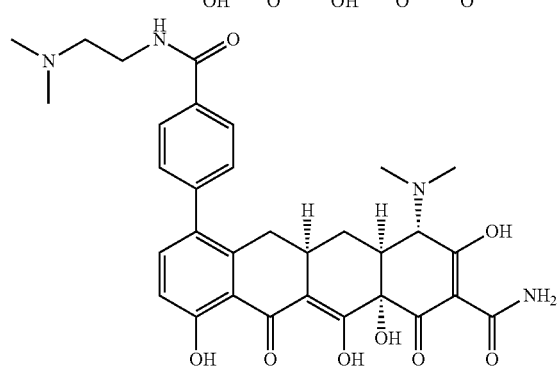
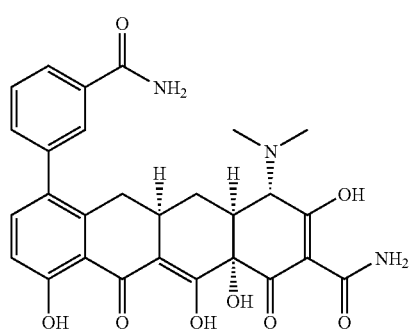
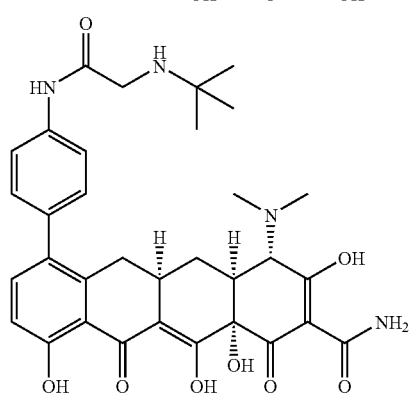

-continued
127
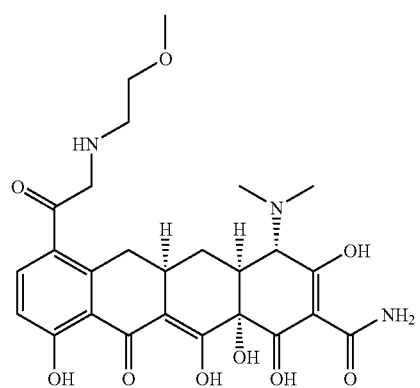
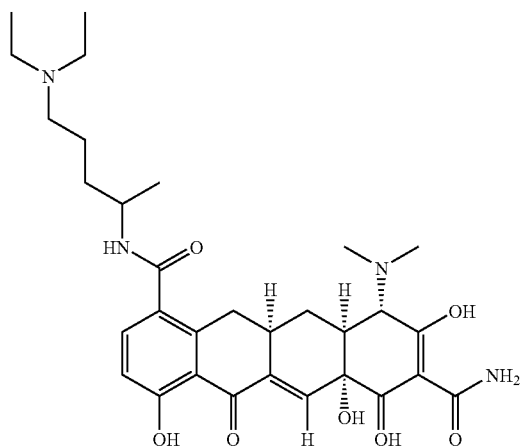
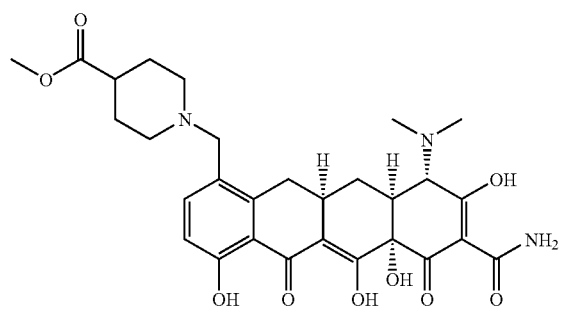
128
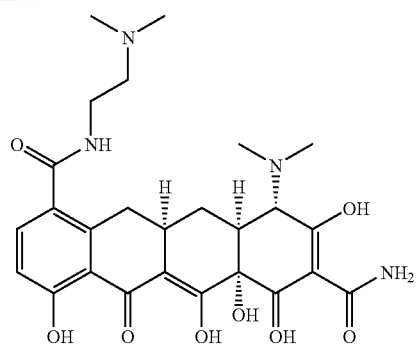
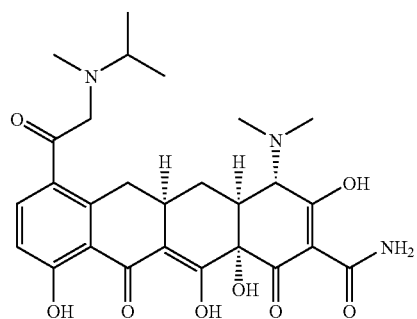
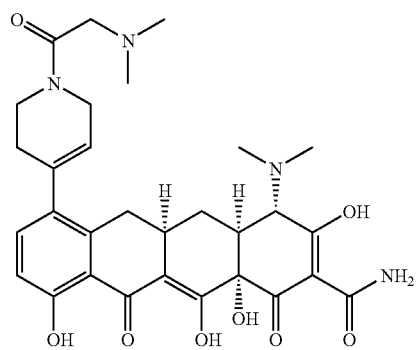
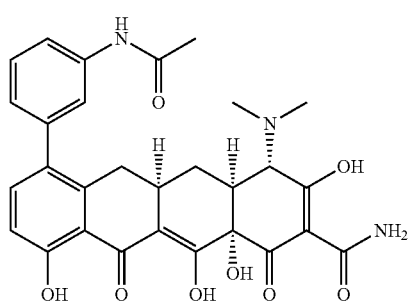

129 130
-continued
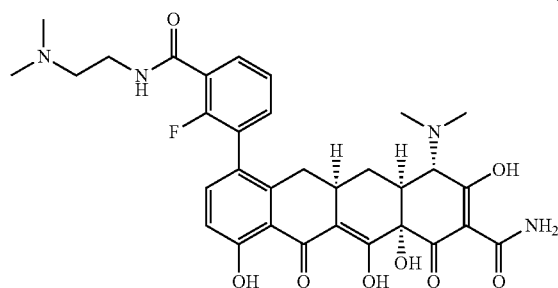
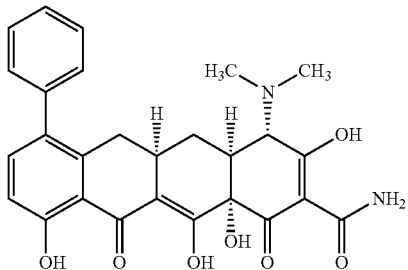
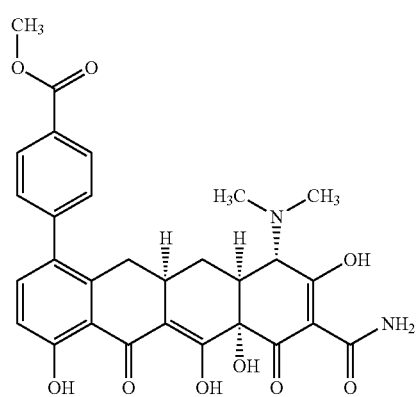
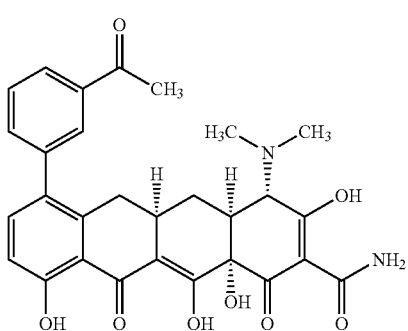
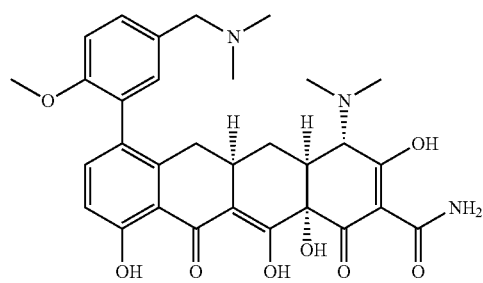
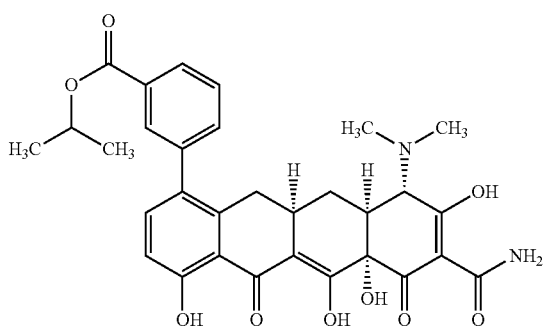
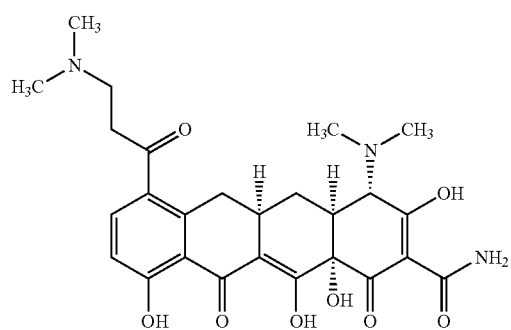
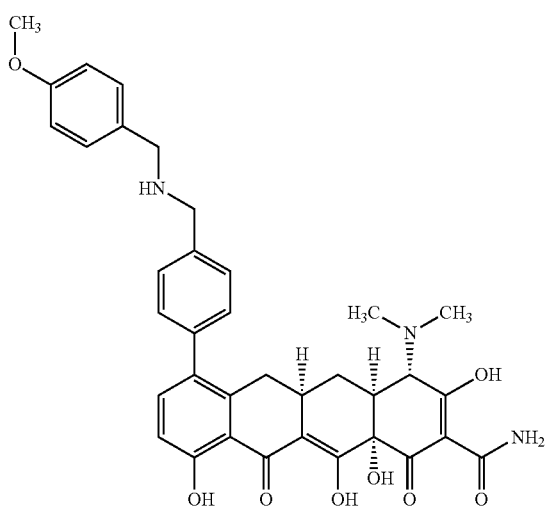

-continued
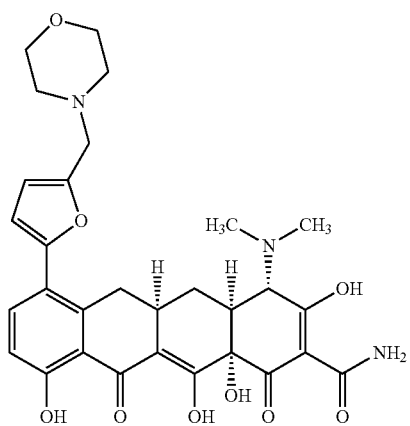
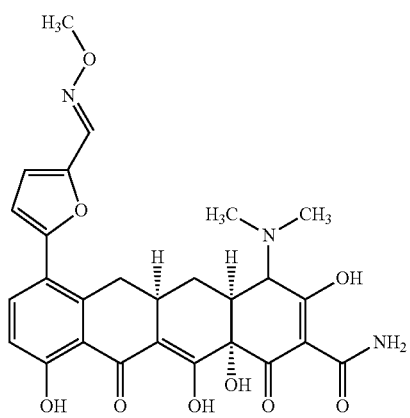
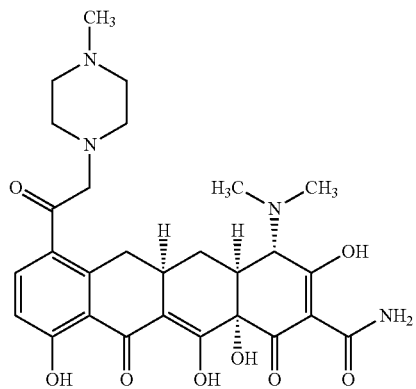
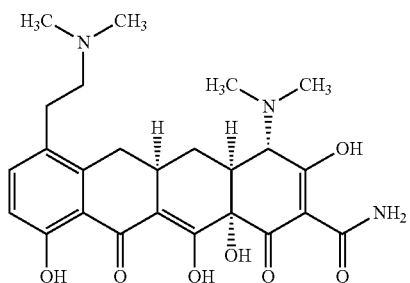
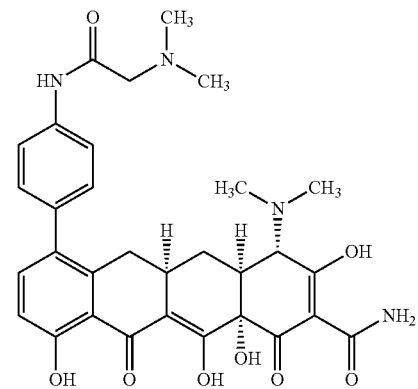
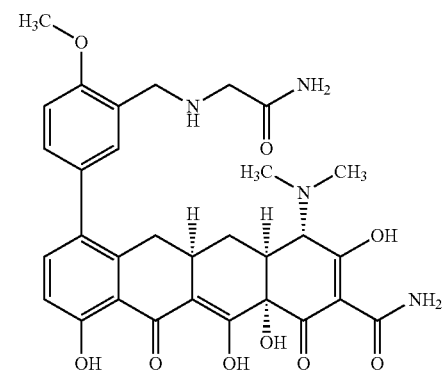

133
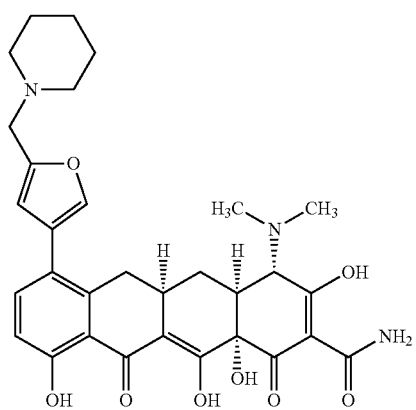
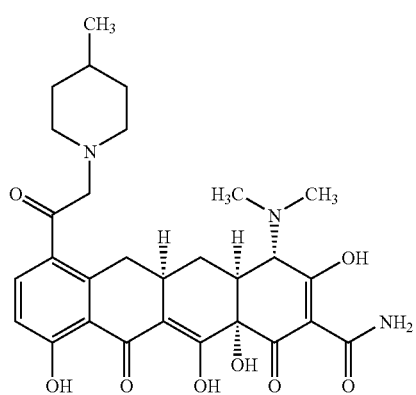
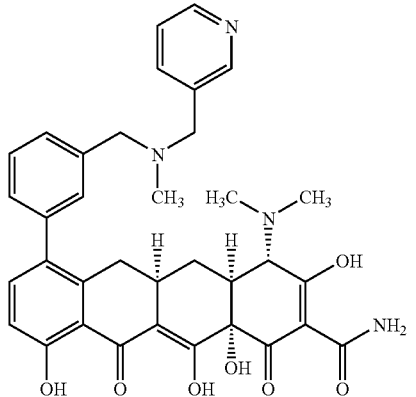
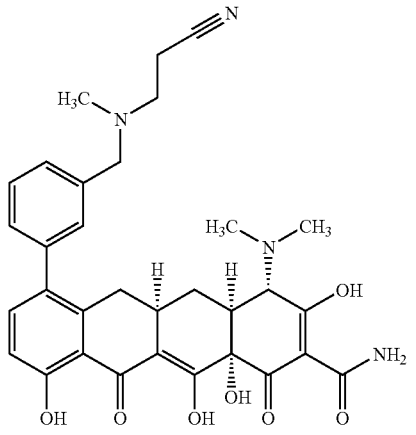
134
-continued
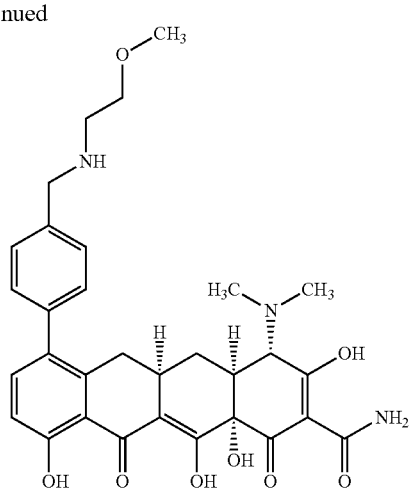
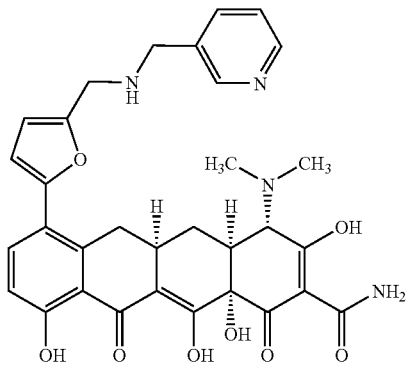
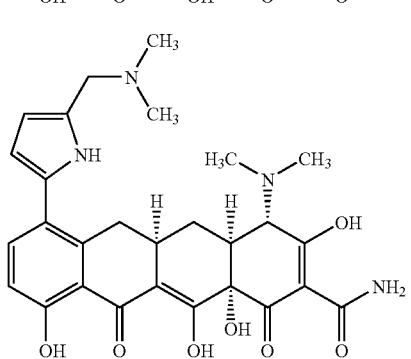
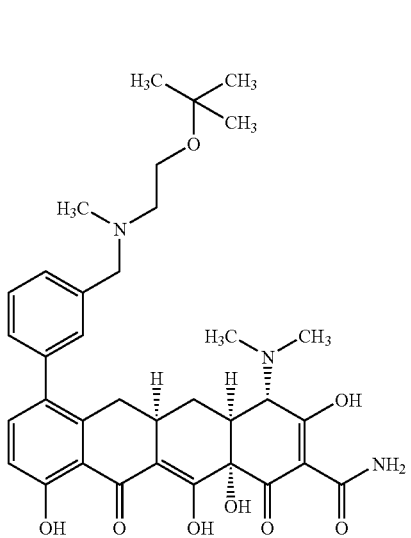

135
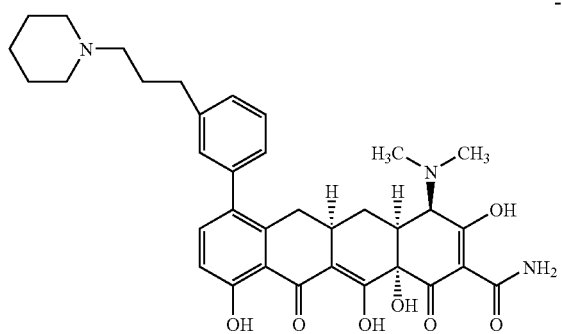
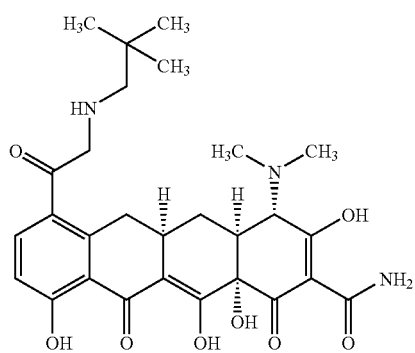
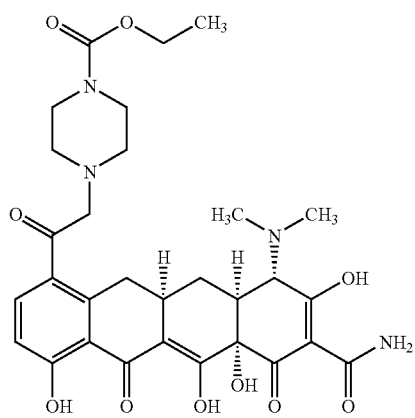
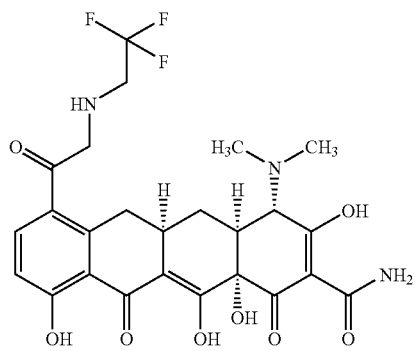
-continued
136
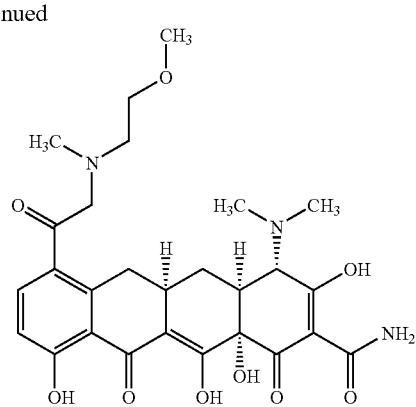
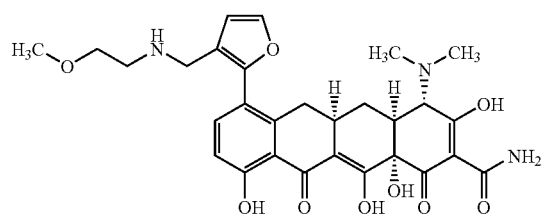
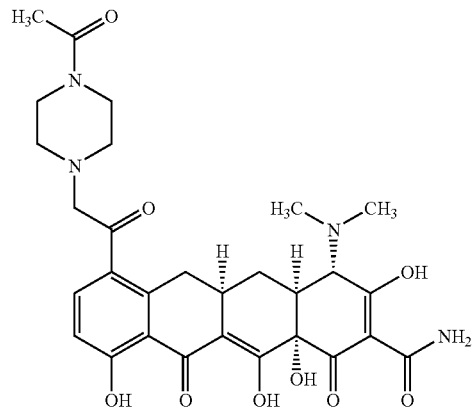
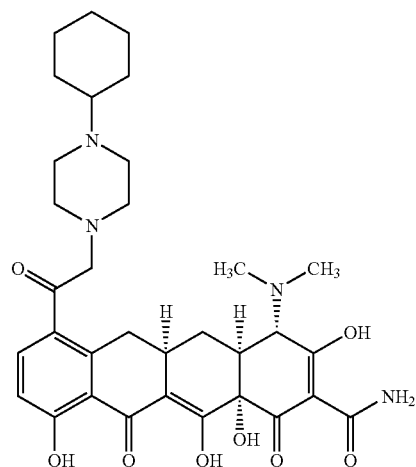

137
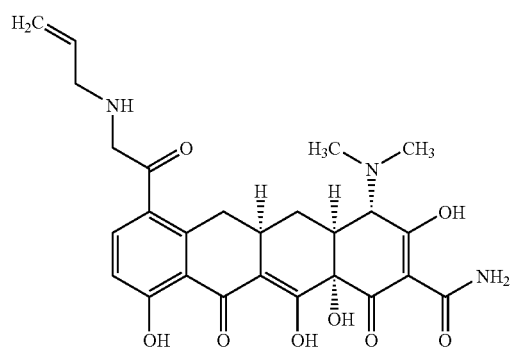
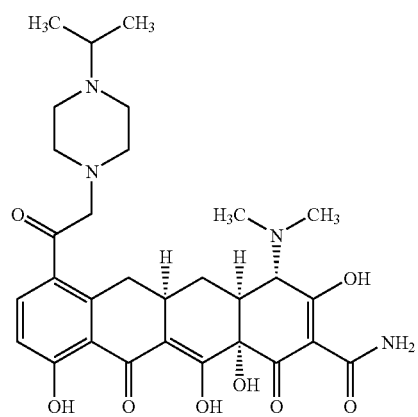
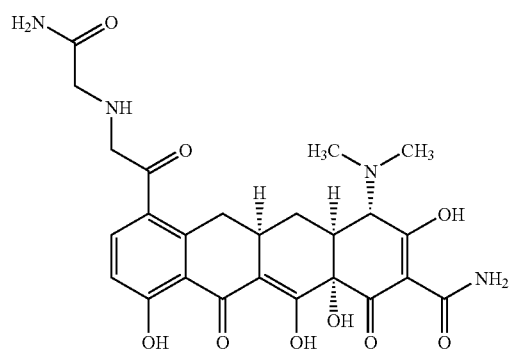
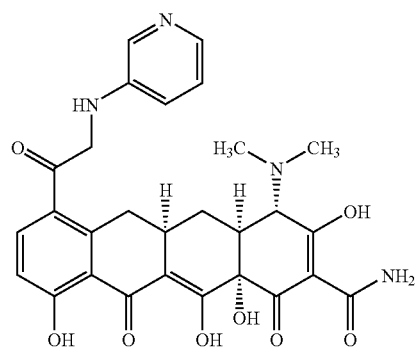
138
-continued
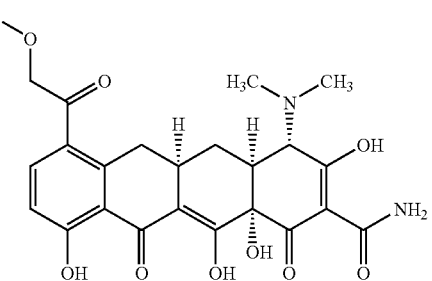
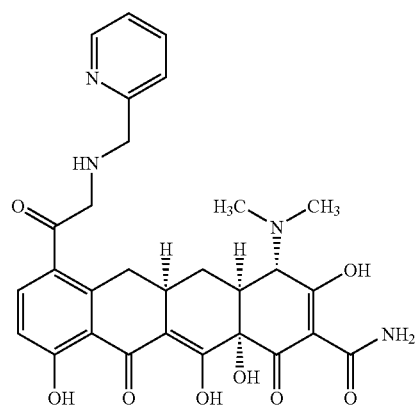
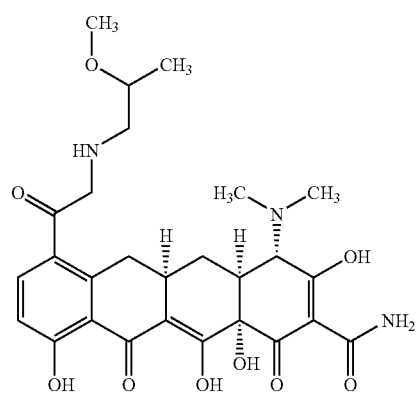
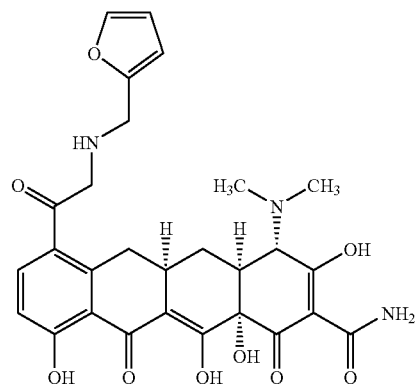

-continued
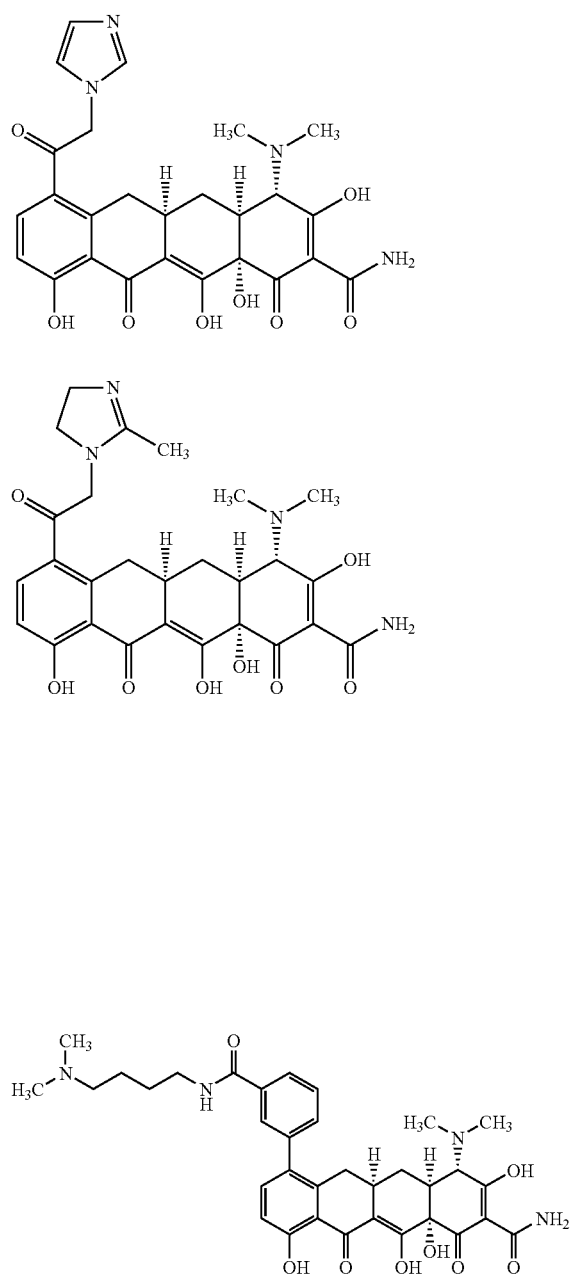
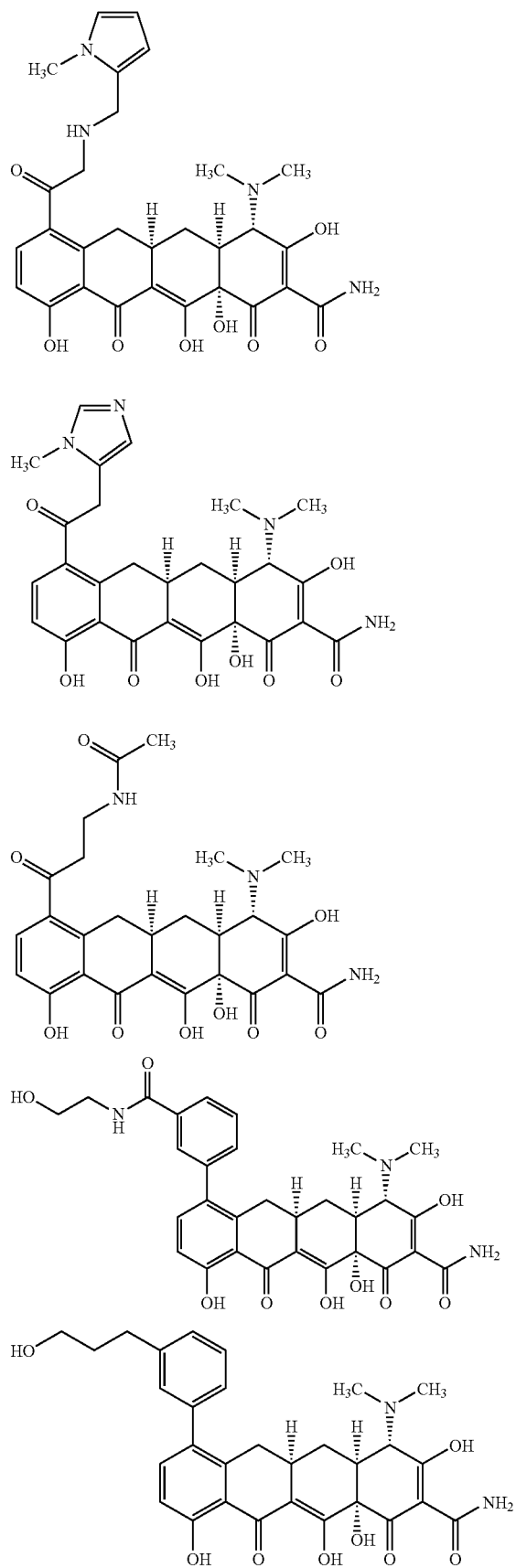

141
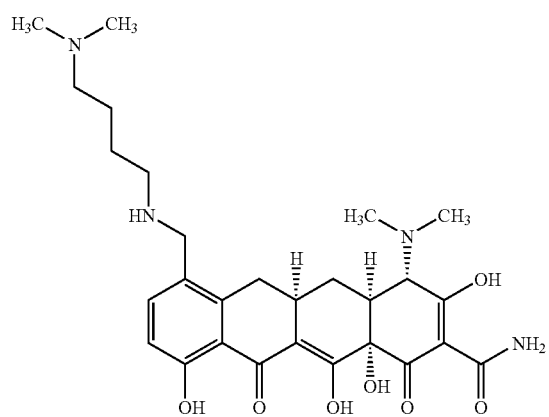
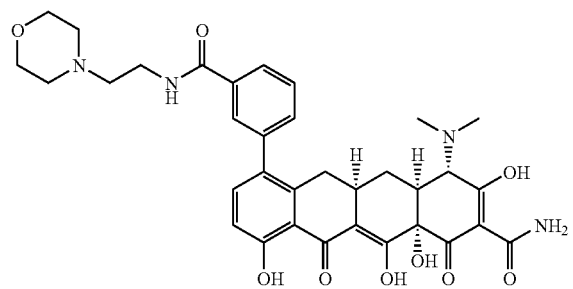
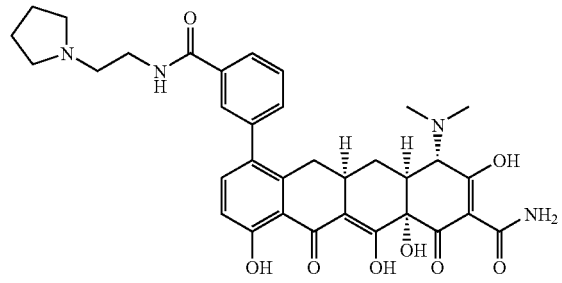
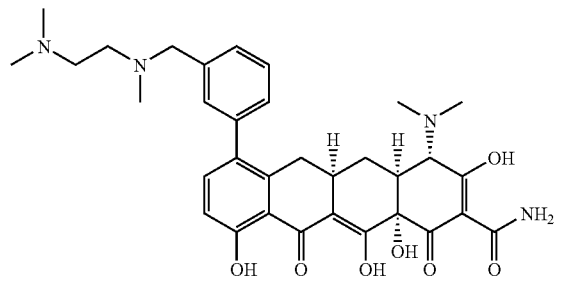
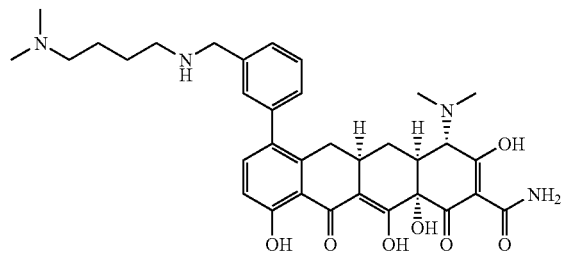
142
-continued
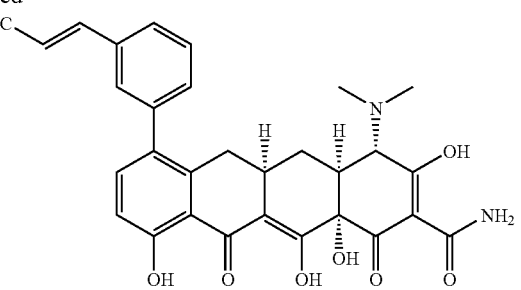
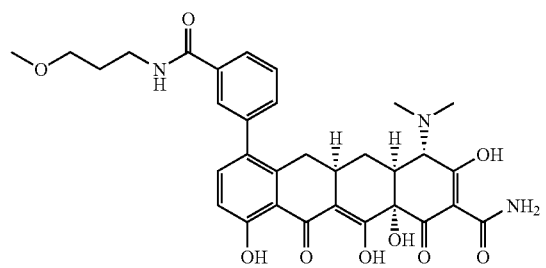
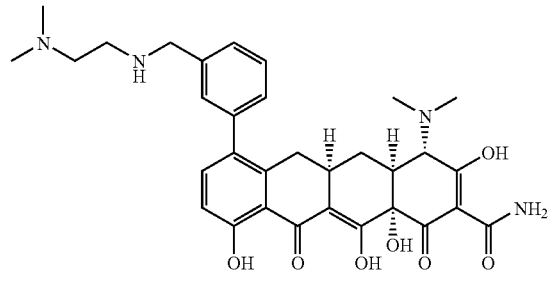
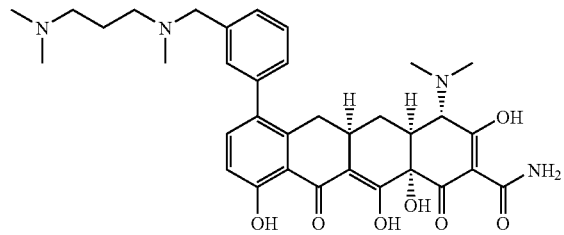
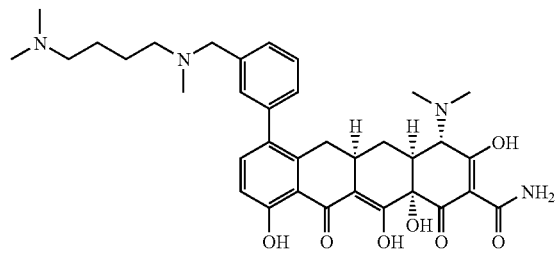

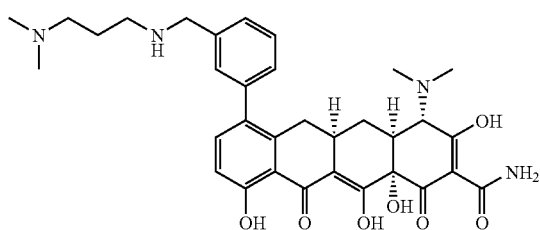

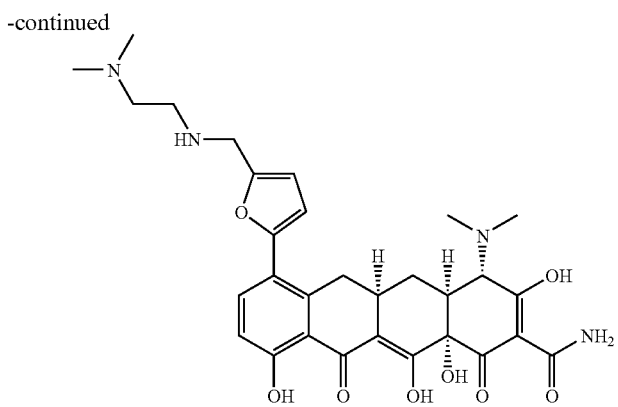

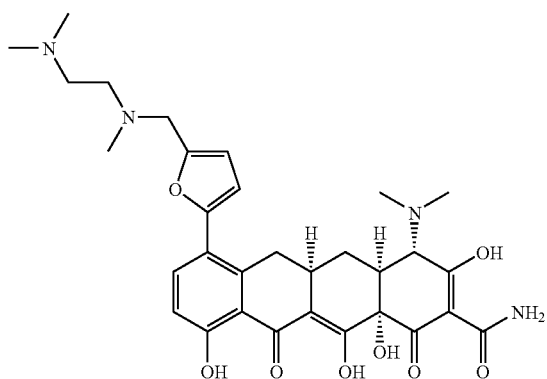

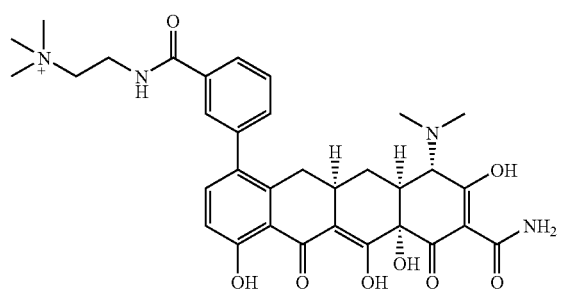

and pharmaceutically acceptable salts, esters and enantiomers thereof, such that said spinal muscular atrophy in said subject is treated.

40. The method of claim 1, wherein said tetracycline compound is of formula XII:

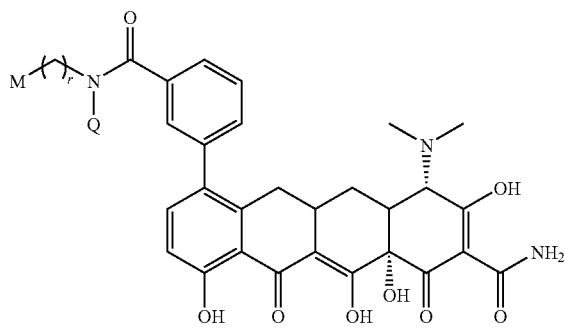

(XII)

wherein
r is an integer from 1 to 10;
M is $OR^{7o*}$ or $NR^{7p*}R^{7q*}$;
Q is hydrogen or alkyl;
$R^{7o*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7p*}$ and $R^{7q*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7p*}$ and $R^{7q*}$ are linked to form a 5- or 6-membered aryl, heterocyclic or aliphatic ring.

41. The method of claim 1, wherein said tetracycline compound is of formula XIV:

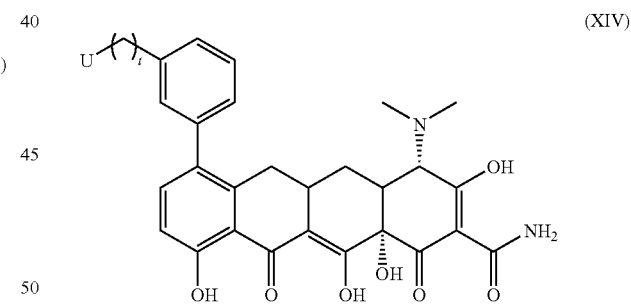

(XIV)

wherein
t is an integer from 1 to 10;
U is $OR^{7u*}$ or $NR^{7v*}R^{7w*}$;
$R^{7u*}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7v*}$ and $R^{7w*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7v*}$ and $R^{7w*}$ are linked to form a 5- or 6-membered aryl, heterocyclic or aliphatic ring.

42. The method of claim 1, wherein said tetracycline compound is of formula XV:

(XV)

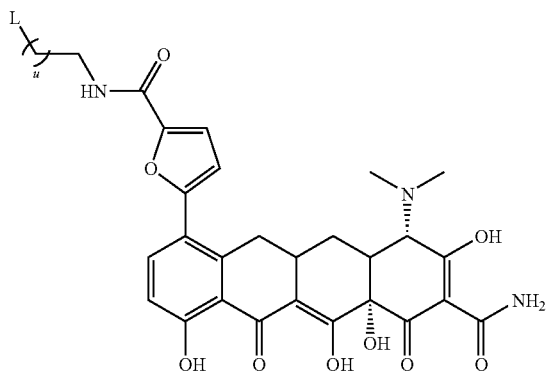

wherein
u is an integer from 1 to 10;
L is $OR^{7x*}$ or $NR^{7y*}R^{7z*}$;
$R^{7x*}$ is hydrogen, alkyl, alkenyl, alkynyl, acyl, hydroxyl, alloxy, halogen, thioether, sulfinyl, sulfonyl, amino, cyano, nitro, carbonyl, aryl or heterocyclic; and
$R^{7y*}$ and $R^{7z*}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7y*}$ and $R^{7z*}$ are linked to form a 5- or 6-membered aryl, heterocyclic or aliphatic ring.

43. The method of claim 1, wherein said tetracycline compound is of formula XVI:

(XVI)

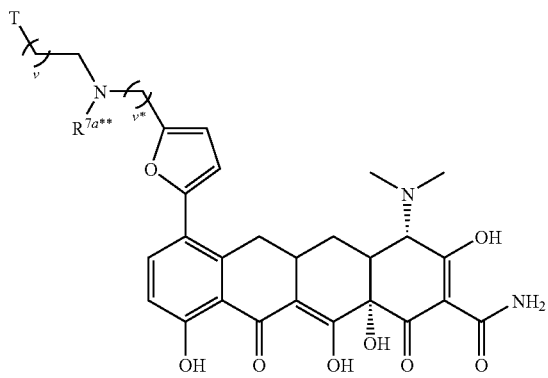

wherein
v and v* are each independently an integer from 1 to 10;
$R^{7a**}$ is hydrogen or alkyl;
T is $OR^{7b}$ or $NR^{7c}R^{7d**}$;
$R^{7b**}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7c}$ and $R^{7d}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7c}$ and $R^{7d}$ are linked to form a 5- or 6-membered aryl, heterocyclic or aliphatic ring.

44. The method of claim 1, wherein said tetracycline compound is of formula XVII:

(XVII)

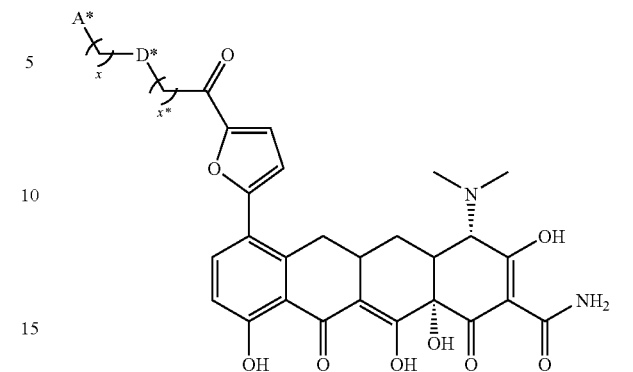

wherein
x and x* are each independently an integer from 1 to 10;
A* is $OR^{7e}$ or $NR^{7f}R^{7g**}$
D* is NH, NCH$_3$, O, or CH$_2$;
$R^{7e**}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7f}$ and $R^{7g}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7f}$ and $R^{7g}$ are linked to form a 5- or 6-membered aryl, heterocyclic or aliphatic ring.

45. The method of claim 1, wherein said tetracycline is of formula XVIII:

(XVIII)

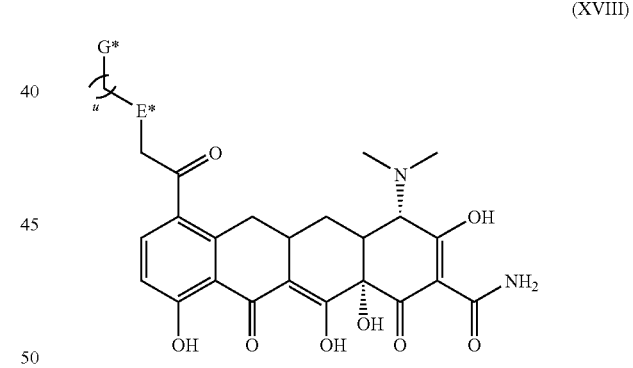

wherein
u is an integer from 1 to 10;
G* is $OR^{7h}$ or $NR^{7i}R^{7j**}$;
E* is NH, NCH$_3$, O, or CH$_2$;
$R^{7h**}$ is hydrogen, alkyl, alkenyl, alkynyl, acyl, hydroxyl, alkoxy, halogen, thioether, sulfinyl, sulfonyl, amino, cyano, nitro, carbonyl, aryl or heterocyclic; and
$R^{7i}$ and $R^{7j}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or $R^{7i}$ and $R^{7j}$ are linked to form a 5- or 6-membered aryl, heterocyclic or aliphatic ring.

46. The method of claim 1, wherein said tetracycline compound is of formula XIX:

(XIX)

wherein
  y is an integer from 1 to 10;
  K* is NR$^{71}$R$^{7m}$;
  J* is NH or NCH$_3$;
  and
  R$^{71}$ and R$^{7m}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{71}$ and R$^{7m}$ are linked to form a 5- or 6-membered aryl, heterocyclic or aliphatic ring.

47. The method of claim 1, wherein said compound is of formula XX:

(XX)

wherein W" is O; and
  R$^{7a''}$ and R$^{7c''}$ are each independently hydrogen, alkyl, alkenyl, alkynyl, acyl, hydroxyl, alkoxy, halogen, thioether, sulfinyl, sulfonyl, amino, cyano, nitro, carbonyl, aryl or heterocyclic or R$^{7a''}$ and R$^{7c''}$ are linked together to form a 5- or 6-membered aryl, heterocyclic or aliphatic ring; or a pharmaceutically acceptable salt thereof.

48. The method of claim 1, wherein said subject is a human.

49. The method of claim 1, further comprising administering said tetracycline compound in combination with a second agent.

50. The method of claim 1, further comprising administering said tetracycline compound in combination with a pharmaceutically acceptable carrier.

51. The method of claim 1, wherein said tetracycline compound increases exon 7 inclusion.

52. The method of claim 1, wherein said tetracycline compound increases intron 6 splicing.

53. The method of claim 1, wherein said tetracycline compound increases cellular SMN protein levels.

54. The method of claim 1, wherein said tetracycline compound increases gems in cells of said subject.

55. The method of claim 1, wherein said tetracycline compound increases FL SMN2 mRNA expression in said subject's liver and/or kidney.

56. The method of claim 1, wherein said compound is:

or a pharmaceutically acceptable salt, ester or enantiomer thereof.

57. The method of claim 1, wherein said compound is:

or a pharmaceutically acceptable salt, ester or enantiomer thereof.

58. The method of claim 1, wherein said compound is:

or a pharmaceutically acceptable salt, ester or enantiomer thereof.

59. The method of claim 1, wherein said compound is:

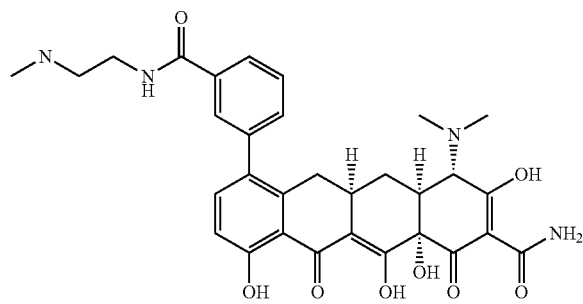

or a pharmaceutically acceptable salt, ester or enantiomer thereof.

60. The method of claim 1, wherein said compound is:

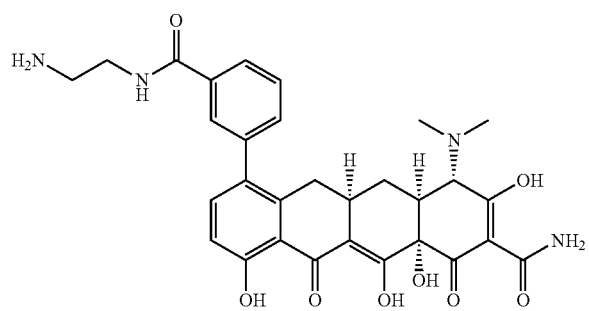

or a pharmaceutically acceptable salt, ester or enantiomer thereof.

61. The method of claim 1, wherein said compound is:

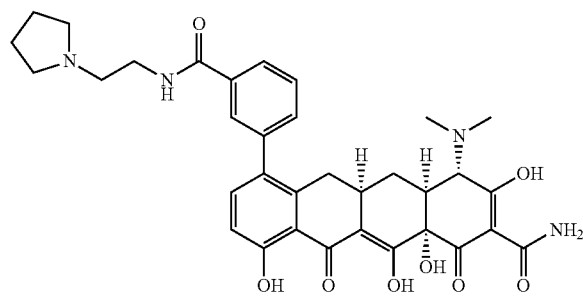

or a pharmaceutically acceptable salt, ester or enantiomer thereof.

62. The method of claim 1, wherein said compound is:

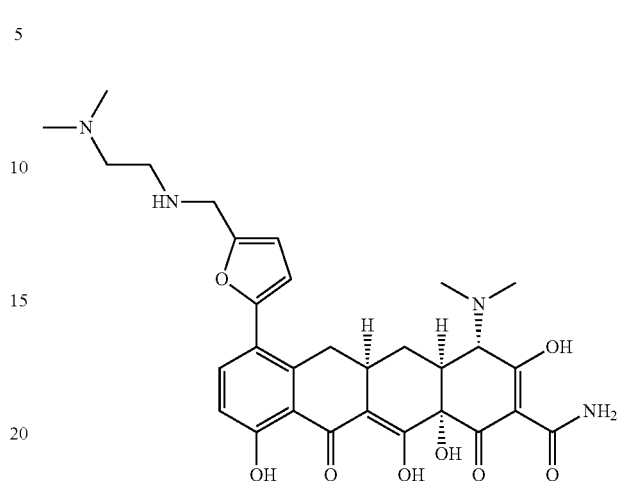

or a pharmaceutically acceptable salt, ester or enantiomer thereof.

63. The method of claim 1, wherein said compound is:

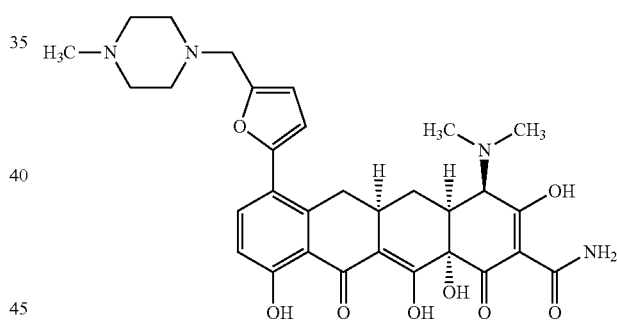

or a pharmaceutically acceptable salt, ester or enantiomer thereof.

* * * * *